(12) United States Patent
Armour et al.

(10) Patent No.: US 6,867,192 B1
(45) Date of Patent: Mar. 15, 2005

(54) COMPOUNDS USEFUL IN THE TREATMENT OF INFLAMMATORY DISEASES

(76) Inventors: Duncan Robert Armour, Discovery Chemistry IPC 924, Pfizer Limited Ramsgate Road, Sandwich, Kent CT13 9NJ (GB); David Brown, Roche Products Limited, Broadwater Road, Welwyn Garden City, Hertfordshire AL7 3AY (GB); Miles Stuart Congreve, GlaxoSmithKline, Five Moore Drive, P.O. Box 13398, Research Triangle Park, NC (US) 27709; Paul Martin Gore, GlaxoSmithKline, Five Moore Drive, P.O. Box 13398, Research Triangle Park, NC (US) 27709; Darren Victor Steven Green, GlaxoSmithKline, Five Moore Drive, P.O. Box 13398, Research Triangle Park, NC (US) 27709; Stuart Holman, GlaxoSmithKline, Five Moore Drive, P.O. Box 13398, Research Triangle Park, NC (US) 27709; Torquil Iain Maclean Jack, GlaxoSmithKline, Five Moore Drive, P.O. Box 13398, Research Triangle Park, NC (US) 27709; Steven Philip Keeling, GlaxoSmithKline, Five Moore Drive, P.O. Box 13398, Research Triangle Park, NC (US) 27709; Andrew McMurtrie Mason, GlaxoSmithKline, Five Moore Drive, P.O. Box 13398, Research Triangle Park, NC (US) 27709; Karen Morriss, GlaxoSmithKline, Five Moore Drive, P.O. Box 13398, Research Triangle Park, NC (US) 27709; Nigel Grahame Ramsden, GlaxoSmithKline, Five Moore Drive, P.O. Box 13398, Research Triangle Park, NC (US) 27709; Peter Ward, GlaxoSmithKline, Five Moore Drive, P.O. Box 13398, Research Triangle Park, NC (US) 27709

( * ) Notice: Subject to any disclaimer, the term of this patent is extended or adjusted under 35 U.S.C. 154(b) by 0 days.

(21) Appl. No.: 09/868,395
(22) PCT Filed: Dec. 16, 1999
(86) PCT No.: PCT/EP99/10000
§ 371 (c)(1), (2), (4) Date: Sep. 6, 2001
(87) PCT Pub. No.: WO00/37444
PCT Pub. Date: Jun. 29, 2000

(30) Foreign Application Priority Data

Dec. 18, 1998 (GB) .............................................. 9828074

(51) Int. Cl.$^7$ ................................................ C07K 5/06
(52) U.S. Cl. ......................... 514/19; 530/331; 514/18
(58) Field of Search ...................... 514/18, 19; 530/331

(56) References Cited

U.S. PATENT DOCUMENTS 4,105,602 A    8/1978   Colescott et al. ........... 524/577

FOREIGN PATENT DOCUMENTS

| GB | 1201121 A | 8/1970 |
|----|-----------|--------|
| WO | WO9703094 A | 1/1997 |
| WO | WO9853814 A | 12/1998 |
| WO | WO9853817 A | 12/1998 |
| WO | WO9853818 A | 12/1998 |
| WO | WO9854207 A | 12/1998 |

OTHER PUBLICATIONS

Danahay H (British journal of pharmacology 120 (2) 289–97, 1997).*
Sanjar (Am Rev Respir Dis 145, A40, 1992).*

* cited by examiner

*Primary Examiner*—Jon Weber
*Assistant Examiner*—David Lukton
(74) *Attorney, Agent, or Firm*—J. Michael Strickland

(57) ABSTRACT

There are provided according to the invention, novel compounds of formula (I)

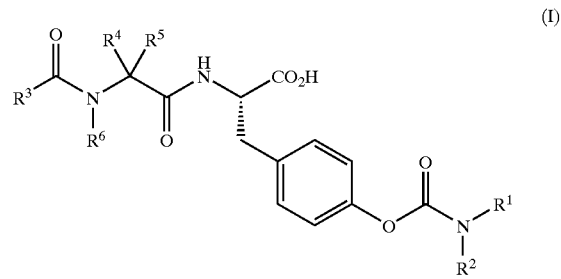

wherein $R^1$, $R^2$, $R^3$, $R^4$, $R^5$ and $R^6$ are as defined in the specification, processes for preparing them, formulations containing them and their use in therapy for the treatment of inflammatory diseases.

20 Claims, No Drawings

COMPOUNDS USEFUL IN THE TREATMENT OF INFLAMMATORY DISEASES

This application is filed pursuant to 35 U.S.C. §371 as a United Sates National Phase Application of International Application No. PCT/EP99/10000 filed 16 Dec. 1999, which claims priority from GB9828074.6 filed 18 Dec. 1998 in the United Kingdom.

This invention relates to novel chemical compounds, processes for their preparation, pharmaceutical formulations containing them and their use in therapy.

Inflammation is a primary response to tissue injury or microbial invasion and is characterised by leukocyte adhesion to the endothelium, diapedesis and activation within the tissue. Leukocyte activation can result in the generation of toxic oxygen species (such as superoxide anion), and the release of granule products (such as peroxidases and proteases). Circulating leukocytes include neutrophils, eosinophils, basophils, monocytes and lymphocytes. Different forms of inflammation involve different types of infiltrating leukocytes, the particular profile being regulated by the profile of adhesion molecule, cytokine and chemotactic factor expression within the tissue.

The primary function of leukocytes is to defend the host from invading organisms, such as bacteria and parasites. Once a tissue is injured or infected, a series of events occurs which causes the local recruitment of leukocytes from the circulation into the affected tissue. Leukocyte recruitment is controlled to allow for the orderly destruction and phagocytosis of foreign or dead cells, followed by tissue repair and resolution of the inflammatory infiltrate. However in chronic inflammatory states, recruitment is often inappropriate, resolution is not adequately controlled and the inflammatory reaction causes tissue destruction.

Integrins are cell surface heterodimeric proteins comprising α and β chains, involved in the inflammatory process. The α4-integrins, which include α4β1 (also known as very late antigen-4 (VLA-4) or CD49d/CD29) and α4β7, are expressed mainly on leukocytes other than neutrophils (eg. eosinophils, T- and B-lymphocytes, basophils and mast cells). The adhesion molecule ligands for α4-integrins include (i) the vascular cell adhesion molecule (VCAM-1; CD106), (ii) a sequence within the alternatively spliced connecting segment-1 (CS-1) in fibronectin (an extracellular matrix protein), and (iii) a site on the mucosal addressin cell adhesion molecule (MAdCAM). Under normal conditions, VCAM-1 is minimally expressed in the vasculature, however, upregulation of VCAM-1 on endothelial cells occurs near sites of inflammation. VCAM-1 has also been identified on a range of non-vascular cells including dendritic cells, bone marrow stromal cells, synoviocytes, astrocytes and some cortical neurons. MAdCAM expression is predominantly associated with gut tissue being expressed in the high endothelial veins of gut associated lymphoid tissue, peripheral lymph nodes and Peyers Patches.

Both α4β1 (VLA-4) and α4β7 can interact with VCAM-1, CS-1 in fibronectin and MAdCAM. The α4-integrin/VCAM-1 interaction enables adhesion and subsequent transmigration of leukocytes through the wall of post-pillary venules to sites of tissue inflammation. Such an interaction is similarly capable of providing a co-stimulatory signal for T-cell activation, whilst the α4-integrin/fibronectin interaction is believed to have a stimulatory role in the degranulation of mast cells, basophils and eosinophils. Therefore, α4-integrin antagonists are capable of intervention at two levels to effect attenuation of the inflammatory processes which are essential in the pathophysiology of many chronic diseases. These include (i) inhibition of the recruitment of leukocytes to sites of tissue inflammation and (ii) inhibition of the activation of leukocytes and the release of inflammatory mediators.

Cell adhesion and signalling, mediated by α4-integrins, are essential in numerous physiological and pathophysiological processes. The therapeutic potential of α4-integrin blocking agents has been investigated previously by testing specific α4-integrin blocking monoclonal antibodies (anti-α4-mAbs) in experimental in vitro and in vivo models of disease (Lobb and Hemler, 1994). Anti-α4-mAbs have shown beneficial effects in animal models of allergic lung inflammation relevant to asthma, including guinea-pig, rat, rabbit and sheep models. Additionally, anti-α4-mAbs have also been shown to be efficacious in (i) rat and mouse models of experimental allergic encephalomyelitis (considered to be a model of the T-cell dependent autoimmune disease, multiple sclerosis), (ii) mouse models of contact hypersensitivity, (iii) colitis in the Cotton-top tamarin, relevant to inflammatory bowel disease (Podolsky et al, 1993), and (iv) insulin dependent diabetes mellitus in the non-obese diabetic mouse (Baron et al, 1994). Fibronectin-derived peptides which are thought to block α4-integrin function have shown efficacy in mouse contact hypersensitivity (Ferguson et al, 1991) and in rat adjuvant arthritis (Wahl et al, 1994).

International patent application numbers WO 98/53814, WO 98/53817 and WO 98/53818 (Merck) describe the use of heterocyclic amide compounds, biarylalkanoic acids and sulphonamide compounds, respectively, as VLA-4 and/or α4/β7 antagonists. WO 98/54207 (Celltech) describes the use of tyrosine derivatives to inhibit the binding of α4 integrins to their ligands for the treatment and prophylaxis of immune or anti-inflammatory disorders. WO97/03094 (Biogen) describes a selection of semi-peptidic compounds which are capable of inhibiting the binding of ligands to the VLA-4 receptor.

We have now found a novel group of α4-integrin antagonist compounds which antagonise both α4β1 and α4β7 integrins, with the potential to block leukocyte adhesion and activation, consequently effecting anti-inflammatory properties. These compounds are therefore of potential therapeutic benefit, especially in providing protection from leukocyte-induced tissue damage in diseases where leukocytes are implicated at the site of inflammation. Antagonists of both α4β1 and α4β7 integrins may have advantages over selective antagonists of α4β1 or α4β7 because both integrins are believed to have a role in inflammation.

Thus, according to one aspect of the invention, we provide compounds of formula I:

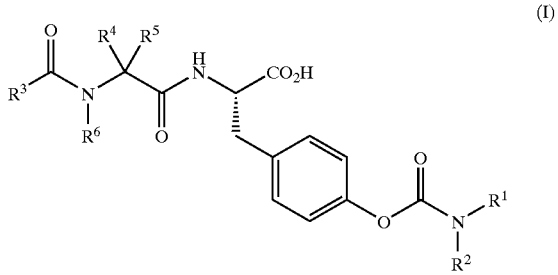

wherein $R^1$ and $R^2$ independently represent
(i) —$C_{1-6}$ alkyl, —$C_{3-8}$ cycloalkyl or —$C_{1-3}$ alkyl$C_{3-8}$ cycloalkyl,
or such a group in which alkyl or cycloalkyl is substituted by one or more halogen, —CN, nitro, hydroxy or —$OC_{1-6}$ alkyl groups;

(ii) —$(CH_2)_eAr^1$ or —$(CH_2)_eOAr^1$;
or $NR^1R^2$ together represent pyrrolidinyl, piperidinyl, piperazinyl, thiomorpholinyl, morpholinyl or azepinyl, or such a group fused to a benzene ring, optionally substituted by one or more —$(CO)_n(CH_2)_rAr^1$, —$(CO)_nC_{1-6}$ alkylAr$^1$Ar$^2$, —$(CO)_nC_{1-6}$alkyl, —$(CH_2)_tOH$, —$(CH_2)_rO(CH_2)_pOH$, —$(CH_2)_tOC_{1-6}$ alkyl, —$O(CH_2)_tAr^1$, —$(CH_2)_rSO_2Ar^1$, piperidin-1-yl, —$(CH_2)_tCONR^8R^9$, —$NR^{10}(CO)_n(CH_2)_tAr^1$, —$NR^{10}(CO)_nC_{1-3}$alkylC$_{3-6}$ cycloalkyl, —$NR^{10}(CO)_nC_{1-6}$ alkyldiC$_{3-6}$ cycloalkyl, —$CONR^{10}(CH_2)_tAr^1$, halogen, —$NHSO_2C_{1-6}$alkyl, —$SO_2NR^{10}R^{11}$, —$SO_2C_{1-6}$ alkyl or —$SO_2Ar^2$ groups;

$R^3$ represents —$C_{1-6}$alkylNHC(=NH)NH$_2$, —$C_{2-6}$alkenylNHC(=NH)NH$_2$, —$C_{2-6}$alkynylNHC(=NH)NH$_2$, —$C_{1-6}$alkylNR$^{14}R^{18}$, —$(CH_2)_hCONR^{14}R^{18}$, —$(CH_2)_hCOC_{1-6}$alkyl, —$(CH_2)_dCHNR^{18}CONR^{20}R^{21}$, —$(CH_2)_mNR^{18}CONR^{14}R^{18}$, —$(CH_2)_dNR^{18}Ar^3$, —$(CH_2)_d CONR^{18}Ar^3$, —$(CH_2)_hCOOR^{18}$, —$(CH_2)_cAr^3$, —$O(CH_2)_cAr^3$, —$(CH_2)_dCO(CH_2)_sAr^3$ or —$(CH_2)_dOAr^3$;

or $R^3$ represents —$(CH_2)_c$-2,4-imidazolidinedione, —$(CH_2)_c$(piperidin-4-yl), —$(CH_2)_c$(piperidin-3-yl), —$(CH_2)_c$(piperidin-2-yl), —$(CH_2)_c$(morpholin-3-yl) or —$(CH_2)_c$(morpholin-2-yl) optionally substituted on nitrogen by —$(CO)_fC_{1-6}$alkyl, —$(CO)_f(CH_2)_cAr^2$ or —C(=NH)NH$_2$;

or $R^3$ represents —$(CH_2)_z$dibenzofuran optionally substituted by —$C_{1-6}$alkyl or halogen;

or $R^3$ represents —$(CH_2)_c$thioxanthen-9-one;

$R^4$ represents hydrogen, —$C_{1-6}$ alkyl, —$C_{1-3}$ alkylC$_{3-6}$ cycloalkyl, —$(CH_2)_qAr^2$, —$C_{1-4}$alkyl-X—$R^7$, —$C_{1-4}$alkyl SO$_2$C$_{1-4}$ alkyl, —$C_{1-6}$alkylNR$^{12}R^{13}$ or —$C_{1-6}$alkylNR$^{12}$COC$_{1-6}$ alkyl;

$R^5$ represents hydrogen, or $R^4R^5$ together with the carbon to which they are attached form a $C_{5-7}$ cycloalkyl ring;

$R^6$ represents hydrogen or —$C_{1-6}$alkyl, or $R^6$ and $R^4$ together with the N and C atoms to which they are respectively attached form a pyrrolidine ring;

$R^7$ represents hydrogen, —$(CH_2)_wNR^{12}R^{13}$, —$(CH_2)_uAr^2$ or —$(CH_2)_wNR^{12}COC_{1-6}$ alkyl;

$R^8$, $R^9$, $R^{16}$ and $R^{17}$ independently represent hydrogen, —$C_{1-6}$alkyl, —$C_{3-6}$cycloalkyl, —$C_{1-3}$ alkylC$_{3-6}$ cycloalkyl, —$C_{2-6}$alkenyl or $NR^8R^9$ or $NR^{16}R^{17}$ together represents morpholinyl, pyrrolidinyl, piperidinyl, piperazinyl or piperazinyl N-substituted by —$C_{1-6}$ alkyl, —COphenyl or —SO$_2$methyl;

$R^{10}$, $R^{11}$, $R^{12}$, $R^{13}$, $R^{15}$, $R^{18}$, $R^{20}$ and $R^{21}$ independently represent hydrogen or —$C_{1-6}$alkyl;

$R^{14}$, $R^{19}$ and $R^{22}$ independently represent hydrogen, —$C_{1-6}$ alkyl, —$C_{3-6}$ cycloalkyl or —$(CH_2)_xAr^4$ or $NR^{14}R^{18}$ or $NR^{15}R^{22}$ together represents morpholinyl, pyrrolidinyl, piperidinyl, piperazinyl or N—$C_{1-6}$alkylpiperazinyl;

$Ar^1$ represents phenyl or a 5 or 6 membered heterocyclic aromatic ring containing 1 to 3 heteroatoms selected from O, N and S optionally substituted by one or more halogen, $C_{1-6}$alkyl, hydroxy, —$OC_{1-6}$alkyl, CF$_3$, nitro, —Ar$^2$ or —OAr$^2$ groups;

$Ar^2$ represents phenyl optionally substituted by one or more halogen, —$C_{1-6}$alkyl, hydroxy, —$OC_{1-6}$alkyl, —CF$_3$ or nitro groups;

$Ar^3$ represents phenyl, a 5 or 6 membered heterocyclic aromatic ring containing 1 to 3 heteroatoms selected from O, N and S, or such a group fused to a benzene ring, optionally substituted by one or more —$CO(CH_2)_gAr^4$, —$(CH_2)_vAr^4$, —$(CH_2)_bCOAr^4$, —$(CO)_aC_{1-6}$ alkyl, —$(CO)_aC_{2-6}$ alkenyl, —$(CO)_aC_{2-6}$ alkynyl, —$(CO)_aC_{3-8}$ cycloalkyl, —$(CO)_aC_{1-6}$haloalkyl, halogen, —COCH$_2$CN, —$(CH_2)_bNR^{16}R^{17}$, —$(CH_2)_bNHC(=NH)NH_2$, —CYNR$^{16}$(CO)$_aR^{17}$, —$(CH_2)_bNR^{15}COR^{19}$, —$(CH_2)_bCONR^{15}R^{22}$, —$(CH_2)_bNR^{15}CONR^{15}R^{22}$, —$(CH_2)_bCONR^{15}(CH_2)_jNR^{15R22}$, —$(CH_2)_bSO_2NR^{15}R^{22}$, —$(CH_2)_bSO_2NR^{15}COAr^2$, —$(CH_2)_bNR^{15}SO_2R^{19}$, —SO$_2R^{19}$, —SOR$^{19}$, —$(CH_2)_zOH$, —COOR$^{15}$, —CHO, —OC$_{1-10}$alkyl, —$O(CH_2)_jNR^{15}R^{22}$, —$O(CH_2)_jNHC(=NH)NH_2$, —$O(CH_2)_bCONR^{16}R^{17}$, —$O(CH_2)_kCOOR^{15}$, —$O(CH_2)_jOAr^2$, —$O(CH_2)_bAr^2$, 3-phenyl-2-pyrazolin-5-one or 4,5-dihydro-3(2H)-pyridazinone groups;

$Ar^4$ represents phenyl or a 5 or 6 membered heterocyclic aromatic ring containing 1 to 3 heteroatoms selected from O, N and S optionally substituted by one or more halogen, —$C_{1-6}$alkyl, hydroxy, —$OC_{1-6}$alkyl, —CF$_3$, nitro or —CONH$_2$ groups;

X and Y independently represent O or S;
a, f, k, s and n independently represent 0 or 1;
b, c, r, x, y and z independently represent an integer 0 to 2;
d, g and u independently represent 1 or 2;
e, h, q and w independently represent an integer 1 to 3;
j and p independently represent an integer 2 to 4;
m independently represents an integer 0 to 4;
t independently represents an integer 0 to 3;
and salts and solvates thereof.

Examples of 5 or 6 membered heterocyclic aromatic rings that $Ar^1$, $Ar^3$ and $Ar^4$ may represent include pyrimidine, pyridine, furan, imidazole, thiophene, pyrrole, thiazole, oxazole, isoxazole, 1,3,4-thiadiazole, 1,2,3-thiadiazole, 1,2,4-thiadiazole, 1,2,4-oxadiazole and pyrazole.

Specific examples of 5 or 6 membered heterocyclic aromatic rings that $Ar^1$ may represent include pyrimidine, pyridine, furan, 1,2,4-thiadiazole and pyrrole.

Specific examples of 5 or 6 membered heterocyclic aromatic rings that $Ar^3$ may represent include thiazole and pyridine. Phenyl fused to a benzene ring represents naphthyl. An example of a 5 or 6 membered heterocyclic aromatic ring fused to a benzene ring that $Ar^3$ may represent includes benzofuran.

Specific examples of 5 or 6 membered heterocyclic aromatic rings that $Ar^4$ may represent include 1,3,4-thiadiazole, 1,2,3-thiadiazole, 1,2,4-oxadiazole and pyrazole.

We prefer $R^1$ and $R^2$ to be defined such that $NR^1R^2$ together represent piperidinyl, piperazinyl, thiomorpholinyl, morpholinyl or 1,2,3,4-tetrahydroisoquinoline optionally substituted by a —$C(CO)_n(CH_2)_rAr^1$, —$(CO)_nC_{1-6}$alkyl, —$(CH_2)_tCONR^8R^9$, —$NR^{10}(CO)_n(CH_2)_rAr^1$, —$NR^{10}(CO)_n$ $C_{1-3}$ alkylC$_{3-6}$ cycloalkyl, —$NR^{10}(CO)_nC_{1-6}$ alkyldiC$_{3-6}$ cycloalkyl, —$(CH_2)_rOC_{1-6}$ alkyl, —$(CH_2)_rO(CH_2)_pOH$, piperidin-1-yl, —$(CH_2)_rOH$ or —$CONR^{10}(CH_2)_rAr^1$ group.

We particularly prefer $R^1$ and $R^2$ to be defined such that $NR^1R^2$ together represents morpholinyl or piperazinyl optionally N-substituted by —$(CO)_nC_{1-6}$ alkyl (especially —$COCH_3$), piperazinyl N-substituted by —$(CO)_n(CH_2)_rAr^1$ (especially —COphenyl and —(CO)$_2$-furanyl), piperidinyl substituted by $NR^{10}(CO)_n(CH_2)Ar^1$ (especially —NHCOCH$_2$phenyl) or piperidinyl substituted by —$(CH_2)_t$ CONR$^8R^9$ (especially —CONH$_2$).

We prefer $R^3$ to represent —$(CH_2)_c$-2,4-imidazolidinedione-3-yl, —$(CH_2)_c$-thioxanthen-9-one-3-yl, —$(CH_2)_cAr^3$, —$O(CH_2)_cAr^3$, —$(CH_2)_dOAr^3$ or —$(CH_2)_z$ dibenzofuran, particularly —$OCH_2Ar^3$, —CH$_2$OAr$^3$ or dibenzofuran, especially —$CH_2OAr^3$ or dibenzofuran.

When $R^3$ represents —$(CH_2)_z$dibenzofuran (particularly dibenzofuran), we prefer it to represent —$(CH_2)_z$-2-dibenzofuran (particularly 2-dibenzofuran).

When $R^3$ represents —$(CH_2)_c$-2,4-imidazolidinedione, we prefer it to represent —$(CH_2)_c$-(2,4-imidazolidinedione-3-yl) (particularly —$CH_2$-2,4-imidazoiidinedione-3-yl).

When $R^3$ represents —$(CH_2)_c$-thioxanthen-9-one, we prefer it to represent —$(CH_2)_c$-(thioxanthen-9-one-3-yl) (particularly —$CH_2$-thioxanthen-9-one-3-yl).

We most especially prefer $R^3$ to represent —$CH_2OAr^3$.

We prefer $R^4$ to represent —$C_{1-6}$ alkyl, $R^5$ to represent hydrogen or for $R^4R^5$, together with the carbon to which they are attached, to form a cyclohexyl ring, and for $R^6$ to represent hydrogen or methyl (particularly hydrogen).

We particularly prefer $R^4$ to represent —$C_{1-6}$ alkyl, and for $R^5$ and $R^6$ to represent hydrogen.

We especially prefer $R^4$ to represent —$CH_2CHMe_2$ and for $R^5$ and $R^6$ to represent hydrogen.

We particularly prefer $R^4$ and $R^5$ to have the stereochemical orientation shown in formula (Ia):

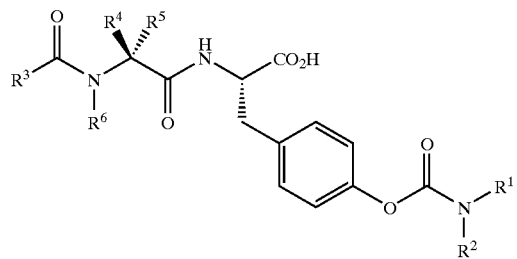

(Ia)

We prefer $R^7$ to represent —$(CH_2)_uAr^2$ or —$(CH_2)_w$NR$^{12}$COC$_{1-6}$ alkyl.

We especially prefer $R^8$ and $R^9$ each to represent hydrogen or for $NR^8R^9$ together to represent piperidinyl or pyrrolidinyl, particularly piperidinyl.

We prefer $R^{10}$ to represent hydrogen or methyl, particularly hydrogen.

We prefer $R^{11}$ to represent hydrogen or methyl, particularly hydrogen.

We prefer $R^{12}$ to represent hydrogen or methyl, particularly hydrogen.

We prefer $R^{13}$ to represent hydrogen or methyl, particularly hydrogen.

We prefer $R^{14}$ to represent hydrogen or methyl, particularly hydrogen.

We prefer $R^{15}$ to represent hydrogen or —$C_{1-6}$ alkyl, particularly hydrogen.

We prefer $R^{16}$ to represent hydrogen, —$C_{1-4}$ alkyl or —$C_{2-4}$ alkenyl, particularly hydrogen or propenyl.

We prefer $R^{17}$ to represent hydrogen, —$C_{1-4}$ alkyl or —$C_{2-4}$ alkenyl, particularly hydrogen, methyl or propenyl.

We prefer $R^{18}$ to represent hydrogen or methyl, particularly hydrogen.

We prefer $R^{19}$ to represent hydrogen or —$C_{1-6}$ alkyl, particularly —$C_{1-6}$ alkyl, especially methyl.

We prefer $R^{20}$ to represent hydrogen or methyl, particularly hydrogen.

We prefer $R^{21}$ to represent hydrogen or methyl, particularly hydrogen.

We prefer $R^{22}$ to represent hydrogen, —$C_{1-4}$ alkyl or —$(CH_2)_xAr^4$ or for $NR^{15}R^{22}$ together to represent piperidinyl, pyrrolidinyl or morpholinyl.

We especially prefer $R^{15}$ and $R^{22}$ to be defined such that $NR^{15}R^{22}$ together represents piperidinyl.

We prefer $Ar^1$ to represent furan, pyrimidine or phenyl optionally substituted by halogen (eg. chlorine or fluorine) or —$OC_{1-6}$ alkyl.

We prefer $Ar^2$ to represent unsubstituted phenyl.

We prefer $Ar^3$ to represent phenyl, naphthyl or benzofuran optionally substituted by one or more —$(CH_2)_yCOAr^4$, —$COOR^{15}$, —$(CH_2)_bSO_2NR^{15}R^{22}$, —$(CH_2)_bNR^{15}SO_2R^{19}$, —$SO_2R^{19}$, $(CO)_aC_{2-6}$ alkenyl, —$(CO)_aC_{1-6}$ alkyl, —$(CO)_aC_{3-8}$cycloalkyl, halogen, —$(CH_2)_bCONR^{15}R^{22}$, 3-phenyl-2-pyrazolin-5-one-2-yl or 4,5-dihydro-3(2H)-pyridazinone-6-yl groups. We particularly prefer $Ar^3$ to represent phenyl or naphthyl optionally substituted by —$(CO)_aC_{1-6}$ alkyl, —$(CO)_aC_{3-8}$ cycloalkyl, halogen, —$(CH_2)_yCOAr^4$ or —$(CH_2)_bCONR^{15}R^{22}$.

We most particularly prefer $Ar^3$ to represent phenyl substituted by n-propyl, tertiary butyl, cyclohexyl, iodine, —COphenyl or COpiperidin-1-yl or naphthyl substituted by COpiperidin-1-yl.

We prefer $Ar^4$ to represent phenyl or furan optionally substituted by halogen, especially unsubstituted phenyl or furan.

We prefer e to represent 1 or 2.

We prefer n to represent 0 or 1.

We prefer r to represent 0 or 1, particularly 1.

We prefer p to represent 2.

We prefer t to represent 0, 1 or 3, particularly 0 or 1, especially 0.

We prefer h to represent 1 or 2, particularly 2.

We prefer d to represent 1.

We prefer m to represent 0 or 1, particularly 1.

We prefer c to represent 0 or 1, particularly 1.

We prefer f to represent 1.

We prefer q to represent 1 or 2, particularly 1.

We prefer u to represent 1.

We prefer w to represent 1 or 2, particularly 1.

We prefer x to represent 0 or 1, particularly 1.

We prefer a to represent 0.

We prefer y to represent 0 or 1, particularly 0.

We prefer b to represent 0 or 1, particularly 0.

We prefer j to represent 2 or 3, particularly 2.

We prefer z to represent 0 or 1, particularly 0.

We prefer k to represent 1.

We prefer s to represent 0.

We prefer g to represent 1.

We prefer X to represent oxygen.

We prefer Y to represent oxygen.

The most preferred compounds of formula (I) are:

(2S)-2-[((2S)-2-{[2-(2-Iodophenoxy)acetyl]amino}-4-methyl pentanoyl)amino]-3-{4-[(4-morpholinylcarbonyl)oxy]phenyl}propanoic acid;

(2S)-2-{[(2S)-2-({2-[2-(Tert-butyl)phenoxy]acetyl}amino)-4-methyl pentanoyl]amino}-3-{4-[(4-morpholinylcarbonyl)oxy]phenyl}propanoic acid;

(2S)-3-(4-{[(4-Acetyl-1-piperazinyl)carbonyl]oxy}phenyl)-2-{[(2S)-2-({2-[2-(tert-butyl)phenoxy]acetyl}amino)-4-methylpentanoyl]amino}propanoic acid;

(2S)-2-[((2S)-2-{[2-(2-Cyclohexylphenoxy)acetyl]amino}-4-methyl pentanoyl)amino]-3-{4-[(4-morpholinylcarbonyl)oxy]phenyl}propanoic acid;

(2S)-2-[((2S)-4-Methyl-2-{[2-(2-methylphenoxy)acetyl]amino}pentanoyl)amino]-3-{4-[(4-morpholinylcarbonyl)oxy]phenyl}propanoic acid;

(2S)-2-{[(2S)-2-({2-[2-(Tert-butyl)phenoxy]acetyl}amino)-4-methyl pentanoyl]amino}-3-{4-[({4-[(2-phenylacetyl)amino]-1-piperidinyl}carbonyl)oxy]phenyl}propanoic acid;

(2S)-3-(4-{[(4-Acetyl-1-piperazinyl)carbonyl]oxy}phenyl)-2-[((2S)-4-methyl-2-{[2-(2-methylphenoxy)acetyl]amino}pentanoyl)amino]propanoic acid;

(2S)-3-(4-{[(4-Benzoyl-1-piperazinyl)carbonyl]oxy}phenyl)-2-{[(2S)-2-({2-[2-(tert-butyl)phenoxy]acetyl}amino)-4-methylpentanoyl]amino}propanoic acid;

(2S)-3-(4-{[(4-Acetyl-1-piperazinyl)carbonyl]oxy}phenyl)-2-({(2S)-2-[(dibenzo[b,d]furan-4-ylcarbonyl)amino]-4-methylpentanoyl}amino)propanoic acid;

(2S)-2-{[(2S)-2-({2-[2-(Tert-butyl)phenoxy]acetyl}amino)-4-methyl pentanoyl]amino}-3-[4-({[4-(2-furoyl)-1-piperazinyl]carbonyl}oxy)phenyl]propanoic acid;

(2S)-2-({(2S)-2-[(Dibenzo[b,d]furan-4-ylcarbonyl)amino]-4-methyl pentanoyl}amino)-3-[4-({[4-(2-furoyl)-1-piperazinyl]carbonyl}oxy)phenyl]propanoic acid;

(2S)-3-(4-{[(4-Benzoyl-1-piperazinyl)carbonyl oxy}phenyl)-2-[((2S)-4-methyl-2-{[2-(2-methylphenoxy)acetyl]amino}pentanoyl)amino]propanoic acid;

(2S)-3-[4-({[4-(Aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid;

(2S)-3-(4-{[(4-Benzoyl-1-piperazinyl)carbonyl]oxy}phenyl)-2-({(2S)-2-[(dibenzo[b,d]furan-4-ylcarbonyl)amino]-4-methylpentanoyl}amino)propanoic acid;

(2S)-3-[4-({[4-(Aminocarbonyl)-1-piperidinyl]carbonyl}oxy)phenyl]-2-({(2S)-2-[(dibenzo[b,d]furan-4-ylcarbonyl)amino]-4-methylpentanoyl}amino)propanoic acid;

and salts and solvates thereof.

The following compounds are also particularly preferred (2S)-3-[4-({[4-(Aminocarbonyl)-1-piperidinyl]carbonyl}oxy)phenyl]-2-[((2S)-2-{[2-(2-benzoylphenoxy)acetyl]amino}-4-methylpentanoyl)amino]propanoic acid;

(2S)-2-{[(2S)-2-({2-[4-(Aminocarbonyl)phenoxy]acetyl}amino)-4-methylpentanoyl]amino}-3-[4-({[4-(aminocarbonyl)-1-piperidinyl]carbonyl}oxy)phenyl]propanoic acid;

(2S)-3-[4-({[4-(Aminocarbonyl)-1-piperidinyl]carbonyl}oxy)phenyl]-2-{[(2S)-2-({2-[2-(tert-butyl)phenoxy]acetyl}amino)-4-methylpentanoyl]amino}propanoic acid;

and salts and solvates thereof.

The above preferred compounds are characterised by low oral bioavailability which is an advantageous property for an inhaled medicine in order to minimise potential side effects.

Suitable salts of the compounds of formula (I) include physiologically acceptable salts such as alkali metal salts, for example calcium, sodium and potassium salts and salts with (trishydroxymethyl)aminomethane. Other salts of the compounds of formula (I) include salts which may not be physiologically acceptable but may be useful in the preparation of compounds of formula (I) and physiologically acceptable salts thereof. If appropriate, acid addition salts may be derived from inorganic or organic acids, for example hydrochlorides, hydrobromides, sulphates, phosphates, acetates, benzoates, citrates, succinates, lactates, tartrates, fumarates, maleates, 1-hydroxynathanoate, methanesulphonate. Examples of solvates include hydrates.

When sidechains of compounds of formula (I) contain chiral centres, the invention extends to mixtures of enantiomers (including racemic mixtures) and diastereoisomers as well as to individual enantiomers. Generally it is preferred to use a compound of formula (I) in the form of a purified single enantiomer.

The compounds of formula (I) and salts and solvates thereof may be prepared by the methodology described hereinafter, constituting a further aspect of this invention.

A process according to the invention for preparing a compound of formula (I) comprises:

(a) hydrolysis of a carboxylic acid ester of formula (II)

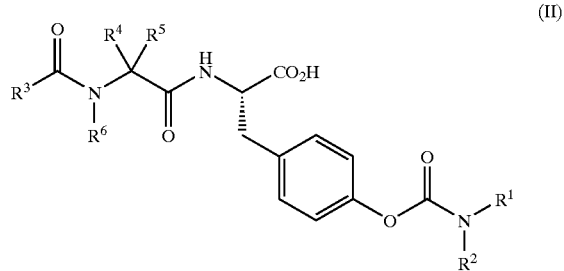

(II)

wherein $R^1$, $R^2$, $R^3$, $R^4$, $R^5$ and $R^6$ are as defined above and R is a group capable of forming a carboxylic acid ester, or (b) deprotecting a compound of formula (I) which is protected.

In process (a) an example of a suitable R group is a $C_{1-6}$ alkyl group such as methyl or t-butyl. Hydrolysis may either occur via an acidic process e.g. involving trifluoroacetic acid and water or via an alkaline route e.g. utilising sodium hydroxide and methanol.

In an alternative solid phase reaction, R may represent a solid support functionalised with available hydroxy groups. Examples of solid supports include resins such as polystyrene resins wherein phenyl rings are provided with hydroxy groups via linkers. An example of a hydroxy functionalised linker is —CH$_2$O(4-hydroxymethyl-phenyl) (Wang Resin) or an N-Fmoc amino acid acyl ester of 3-methoxy-4-oxymethyl-phenoxymethylated 1% divinylbenzene cross-linked polystyrene (Sasrin resin).

In process (b) examples of protecting groups and the means for their removal can be found in T. W. Greene 'Protective Groups in Organic Synthesis' (J. Wiley and Sons, 1991). Suitable amine protecting groups include sulphonyl (e.g. tosyl), acyl (e.g. benzyloxycarbonyl or t-butoxycarbonyl) and arylalkyl (e.g. benzyl), which may be removed by hydrolysis or hydrogenolysis as appropriate.

Compounds of formula (II) may be prepared following Scheme 1;

Scheme 1

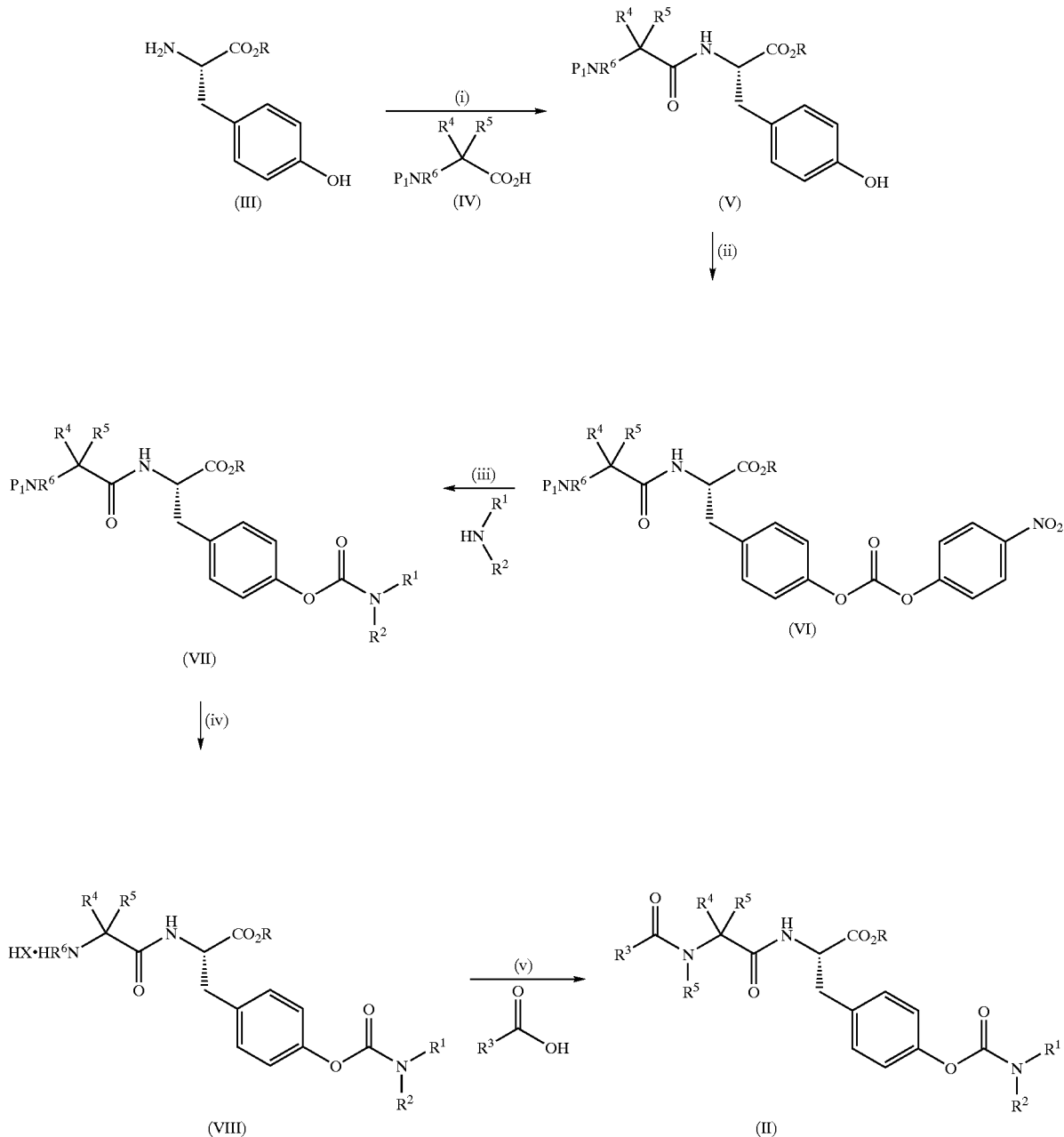

Step (i) In this Scheme we prefer R to represent methyl.

Compounds of formula (III) and (IV) may be reacted under conventional conditions for preparation of an amide. Desirably a coupling agent eg. WSCDI with or without HOBT in an inert solvent such as MeCN or DMF is used. $P_1$ is an amine protecting group such as one described previously under process (b). In this Scheme we prefer $P_1$ to represent Boc.

Step (ii) The conversion of formula (V) to (VI) is suitably carried out with p-nitrophenylchloroformate under conventional conditions eg. in the presence of an organic base, eg. pyridine and an inert organic solvent such as DCM.

Step (iii) This reaction may be performed by combination of the reagents in a suitable solvent, such as DCM in the presence of an organic base such as DIPEA.

Step (iv) This deprotection step may be performed under conventional conditions. When $P_1$ represents Boc, it may be removed by treatment with acid e.g. a hydrohalic acid (HX) such as HCl.

Step (v) A condensation reaction of formula (VIII) with the compound of formula $R^3CO_2H$ may be performed under conditions similar to those described above for step (I).

An alternative process for preparation of compounds of formula (II) is given in Scheme 2 below:

Scheme 2

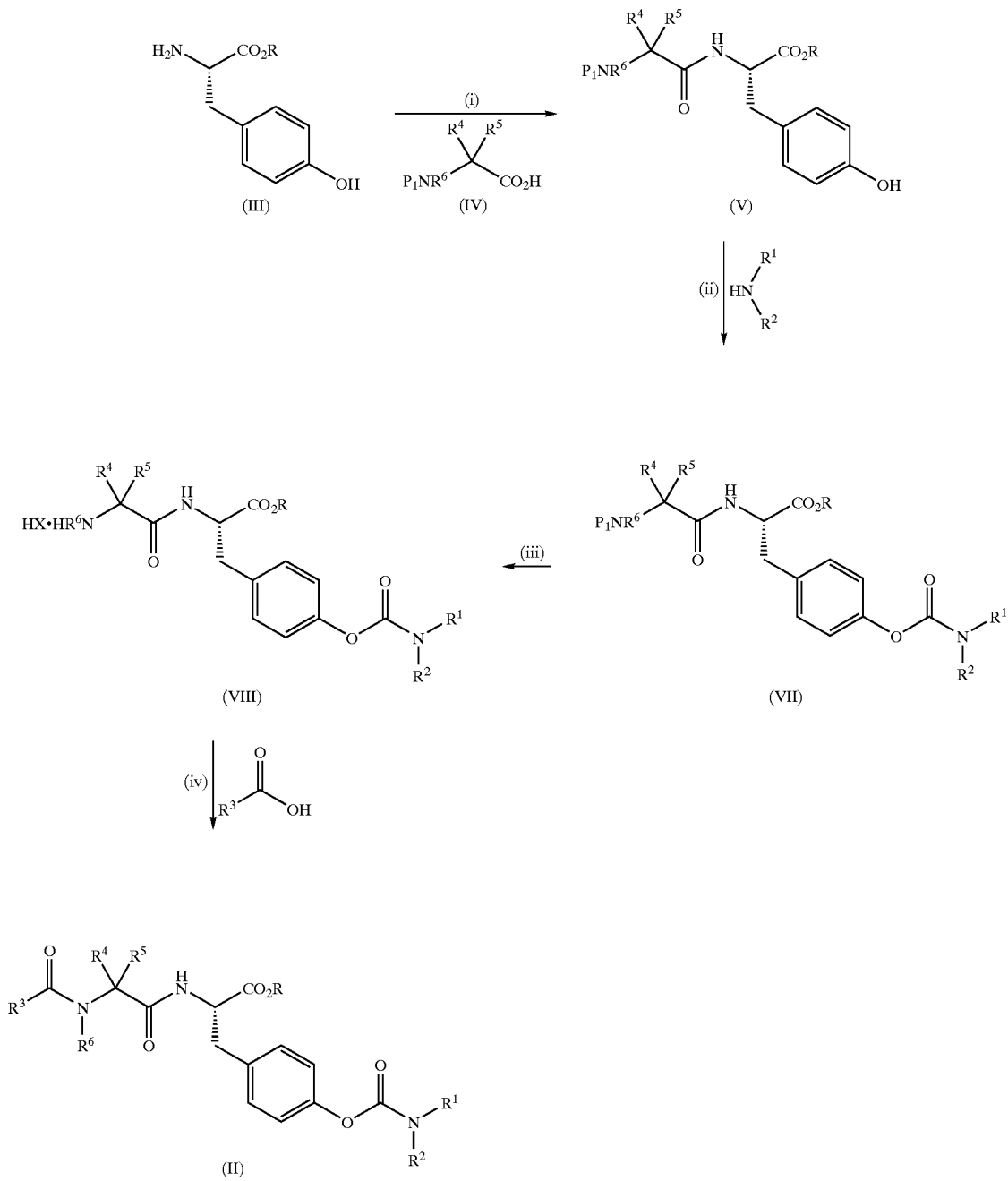

Step (i) In this Scheme we prefer R to represent t-Bu. The reaction conditions for this step are analogous to those for Scheme 1 step (i).

In compounds of formula (IV) in this Scheme we prefer $P^1$ to represent Cbz.

Step (ii) This process comprises a two stage reaction, consisting of (a) treatment with a carboxyl donor such as $(Cl_3CO)_2CO$ typically in the presence of an organic base such as DIPEA and a suitable solvent, such as THF or DCM followed by (b) conversion to the carbamate by treatment with $R^1R^2NH$ in a process analogous to that described previously in Scheme 1 step (iii).

Step (iii) This deprotection reaction can be performed under conventional conditions. When $P_1$ represents Cbz, deprotection may be achieved by hydrogenolysis e.g. by treatment with ammonium formate in the presence of Pd/C in a solvent such as ethanol. The reaction may be worked up with acid, such as a hydrohalic acid to give the product as a hydrohalic acid salt (e.g. the HCl salt).

Step (iv) This process is analogous to Scheme 1, step (v).

An alternative process for preparation of compounds of formula (II) is given in Scheme 3 below:

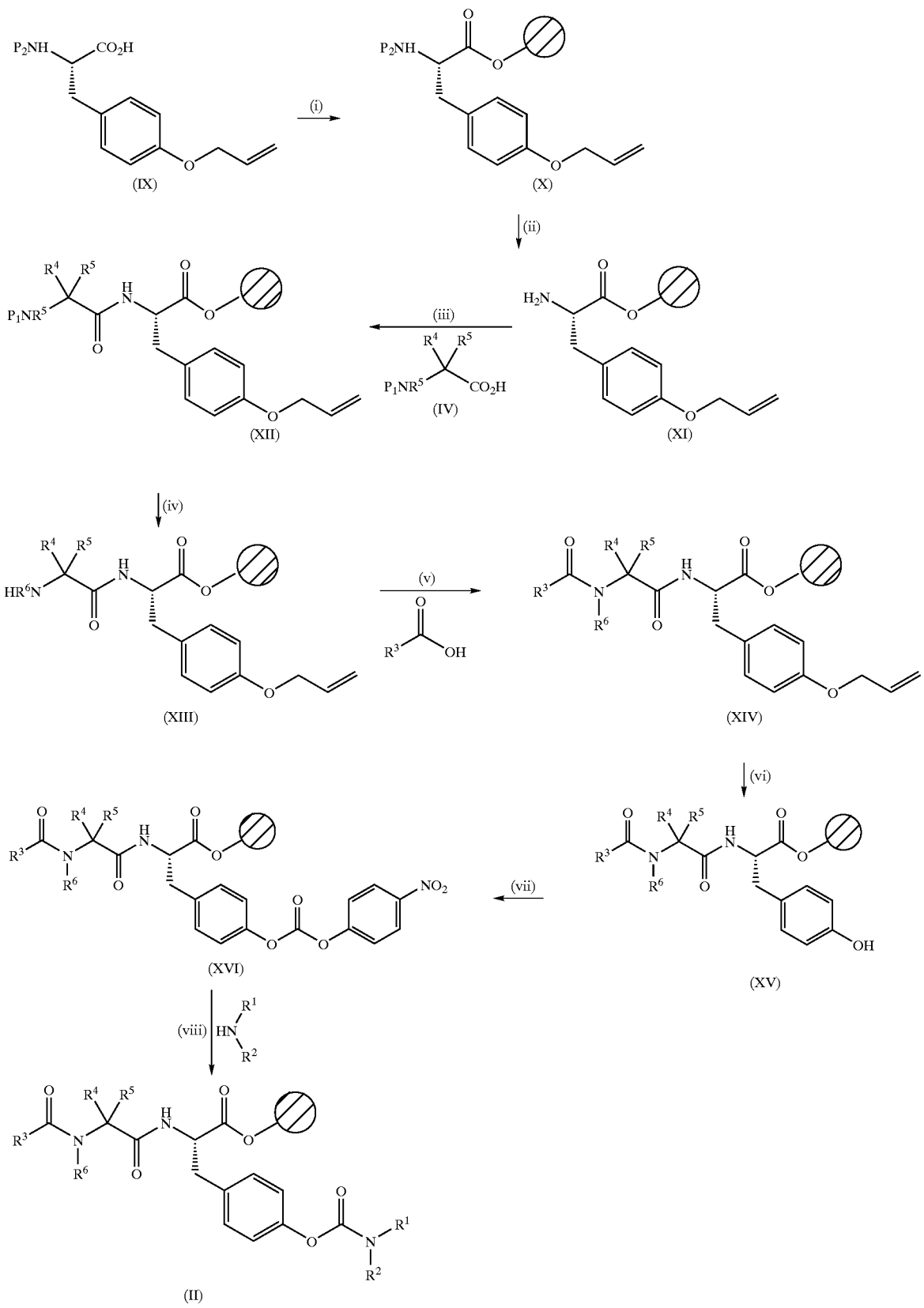

Step (i) $P_2$ is an amine protecting group such as one described previously and in this Scheme we prefer $P_2$ to represent Fmoc. More preferably $P_2$ will be Boc.

A compound of formula (IX) may be reacted onto a suitable solid phase, such as a hydroxy functionalised polystyrene resin (e.g. Wang or Sasrin resin) in the presence of 2,6-dichlorobenzoyl chloride, pyridine and a suitable solvent, such as DMF.

Step (ii) Removal of N-protecting group $P_2$ may be achieved under conventional conditions; e.g. when $P_2$ represents Fmoc, by treatment with an organic base such as piperidine in a suitable solvent, such as DMF or eg. when $P_2$ represents Boc, by treatment with chlorotrimethylsilane and phenol in a suitable solvent such as DCM.

Step (iii) In this Scheme, $P_1$ may suitably represent Fmoc. Alternatively, it may suitably represent Boc. Reaction of a compound of formula (XI) with the compound of formula (IV) to produce an amide, may be performed in the presence of a coupling agent, such as PyBop, an organic base, such as DIPEA and a suitable solvent, such as DMF.

Step (iv) This de-protection reaction may be performed under conventional conditions eg. when $P_1$ represents Fmoc or Boc, under conditions analogous to those described above for step (ii).

Step (v) A condensation reaction of formula (XIII) with the compound of formula $R^3CO_2H$ may be performed in the presence of a suitable coupling agent, such as PyBop, an organic base, such as DIPEA and a suitable solvent, such as DMF.

Step (vi) This step comprises an alkenyl chain cleavage reaction on the compound of formula (XIV) to produce a compound of formula (XV), eg. by the treatment with $Pd(PH_3)_4$ and $PhSiH_3$ (or morphoaine) in the presence of a suitable solvent, such as DCM.

Step (vii) The conversion of a compound of formula (XV) to a compound of formula (XVI) is suitably performed by treatment with p-nitrophenyl chloroformate, under conventional conditions, in the presence of an organic base, such as DIPEA and an inert organic solvent, such as THF and/or DCM.

Step (viii) This reaction may be performed by combination of the reagents in the presence of an organic base, such as DIPEA and suitable solvents, such as DCM and/or THF.

An alternative process for preparation of certain compounds of formula (II) is given in Scheme 4 below:

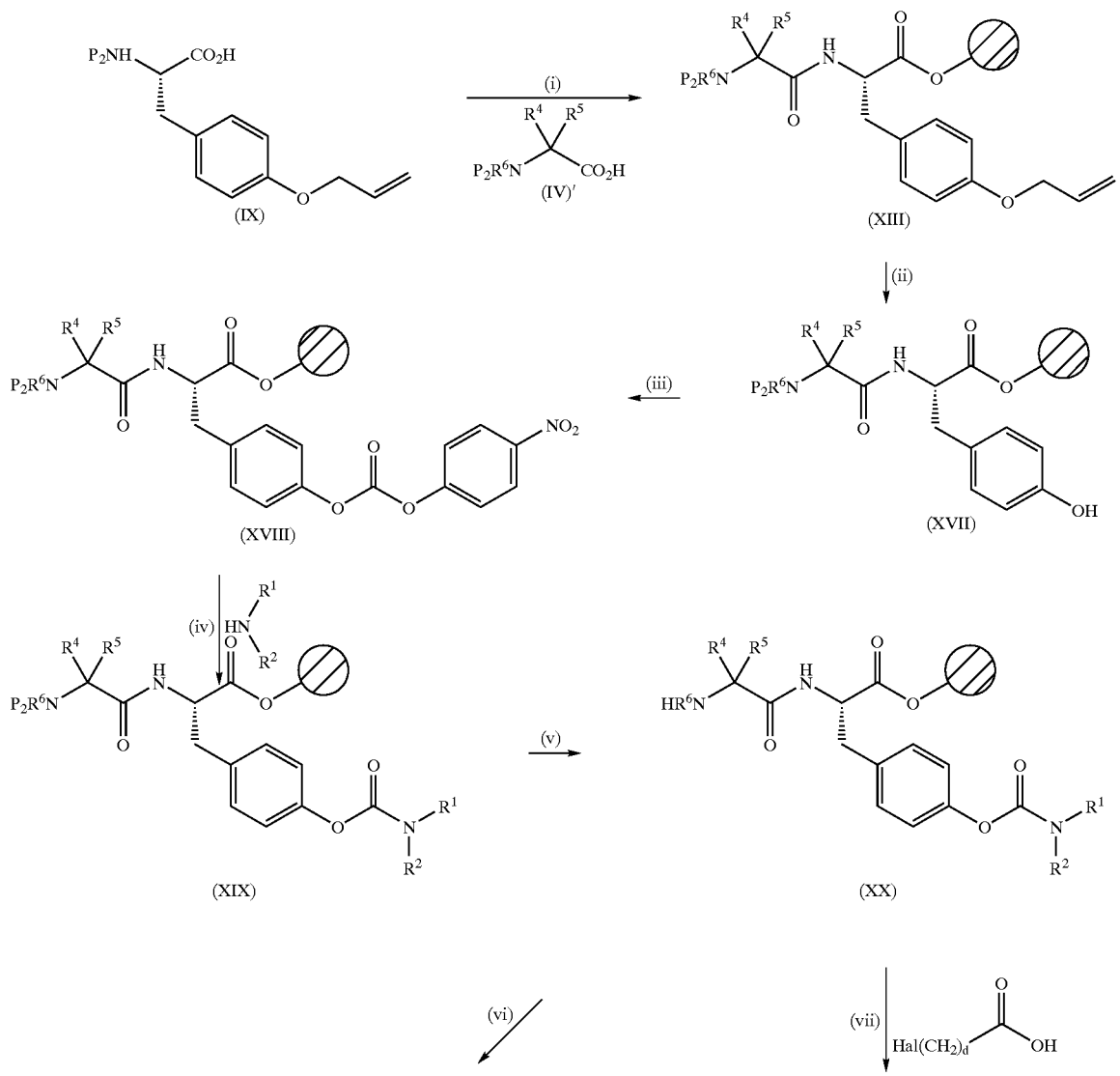

Scheme 4

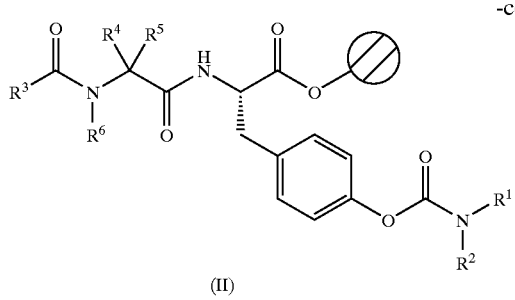

(II)

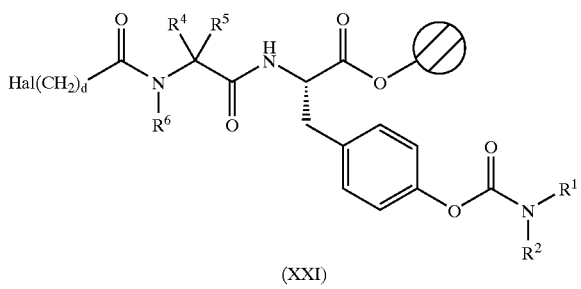

(XXI)

(viii) | Ar³—OH

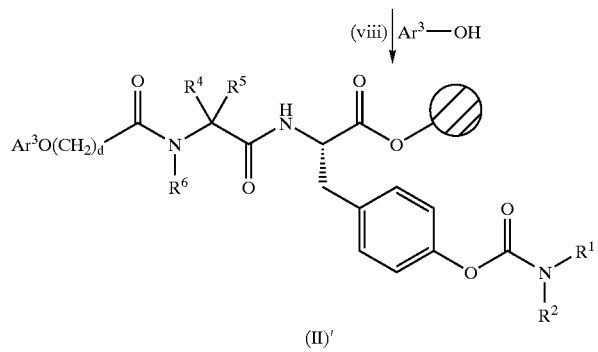

(II)'

Step (i) In this Scheme we prefer $P_2$ to represent Fmoc. This conversion may be achieved following processes analogous to those of Scheme 3 steps (i) to (iii).

Step (ii) An alkenyl chain cleavage reaction may be performed by a process analogous to Scheme 3 step (vi).

Step (iii) A p-nitrophenyl carbonate formation reaction, may be performed with reaction conditions analogous to Scheme 3 step (vii).

Step (iv) The conversion of formula (XVIII) to (XIX) can be performed by a reaction analogous to Scheme 3 step (viii).

Step (v) This de-protection reaction may be performed using an analogous process to Scheme 3 step (ii).

Step (vi) The conversion of formula (XX) to (II) can be performed by a condensation reaction in the presence of a suitable acid, employing a suitable coupling agent, such as PyBop, an organic base, such as DIPEA and a solvent, such as DMF.

Compounds of formula (II) in which $R^3$ represents —$(CH_2)_dOAr^3$ may alternatively be prepared from compounds of formula (XX) following steps (vii) and (viii):

Step (vii) The conversion of formula (XX) to (XXI) can be performed by a condensation reaction in the presence of a haloalkanoic acid (such as the bromo derivative i.e. Hal represents bromine), employing a suitable coupling agent, such as DIC and a solvent, such as DMF.

Step (viii) In this step, the reaction of a compound of formula (XXI) with a compound of formula $Ar^3$—OH group may be undertaken in the presence of potassium carbonate, sodium iodide and a suitable solvent, such as DMF.

Compounds of formula III, IV, IV, $HNR^1R^2$, $R^3COOH$, IX, $Hal(CH_2)_dCOOH$ and $Ar^3$—OH are either known or may be prepared by known methods.

Compounds of the invention may be tested for in vitro and in vivo biological activity in accordance with the following assays.

(1) Jurkat J6/VCAM-1 Adhesion Assay

This assay was used to investigate the interaction of the integrin VLA-4, expressed on the Jurkat J6 (human lymphoblast cell line) cell membrane with VCAM-1. Polystyrene 96-well microtitre plates were coated with human immunoglobulin G (IgG; Sigma Chemicals, UK, Product No. 14506) at a concentration of 0.05 mg ml$^{-1}$ in bicarbonate buffer (36 mM $NaHCO_3$ and 22 mM $Na_2CO_3$, prepared in Dulbecco's phosphate buffered saline at pH 9.8 (PBS); Sigma Chemicals, UK, Product No. 14190-094) for 2 hours at 37° C. This solution was then aspirated and the plates were washed twice with PBS.

VCAM-1 was prepared by cloning its constituent seven domains into a *Drosophila* expression system with a zz (Protein A) tag. This zzVCAM-1 was then expressed from *Drosophila melanogaster* S2 cell culture, induced with copper. Protease inhibitors were added and the culture supernatant was clarified either by filtration through a 0.2 μm filter or by centrifugation. The zzVCAM-1 was then purified from this clarified medium using an IgG agarose column, equilibrated with either 20 mM sodium phosphate pH 7.2 alone or in the presence of 0.5M sodium chloride. Elution of zzVCAM-1 from the column was mediated using 3M ammonium thiocyanate, which was subsequently removed using a G25 desalting column, equilibrated with 20 mM sodium phosphate, pH 7.2. The purified zzVCAM-1 was then concentrated to a small volume (Amicon stirred cell concentrators) until a concentration of 62.5 ng ml$^{-1}$ was obtained, calculated using the extinction coefficient value.

This solution of zzVCAM-1 was then incubated overnight at 4° C. in the IgG coated microtitre plates with 3% bovine serum albumin (BSA) in PBS, followed by aspiration and two further washes with PBS. A concentration of the Jurkat J6 cells (6×10$^6$ cels ml$^{-1}$), grown in cell media RPMI 1640 (HyClone Ltd, Product No. B-9106-L) supplemented with 10% heat inactivated fetal calf serum (FCS; Gibco BRL, Product No. 10099-075) and 2 mM L-glutamine, were labelled with 10 μM of the fluorescent dye, 2', 7'-bis(2-carboxyethyl)-5-(e6)-carboxyfluorescein acetoxymethyl ester (BCECF-AM; Molecular Probes Inc, Product No. B-1150) at 37° C. for 10 minutes. The excess dye was then removed by centrifugation at 500×g for 5 minutes and the cells were resuspended at a concentration of 1.2×10⁷ cells ml⁻¹ in Hank's balanced salt solution (HBSS; Gibco BRL, Product No. 14190-094).

Equal volumes of compounds (dissolved in an appropriate solvent and diluted in HBSS containing 1 mM $MnCl_2$) and the labelled Jurkat J6 cells, were added to the VCAM-1 coated plates and adhesion was allowed to proceed for 30 minutes at 37° C. Non, or loosely adhered cells, were removed by inversion of the plate and blotted with tissue paper. Two washes with PBS and further blotting were then performed, before the addition of 2% detergent (Triton-X®; Sigma Chemicals UK, Product No. X100). Counting was undertaken in a Wallac Viktor™ Fluorimeter, where low fluorescence values were indicative of compounds which had inhibited adhesion. All samples were assayed in singlicate and the following four parameter curve fit, shown by Equation (I) was applied:

$$y = \frac{a-d}{1+\left(\frac{x}{c}\right)^b} + d \qquad \text{Equation (I)}$$

Where a is the minimum, b is the Hill slope, c is the $IC_{50}$ and d is the maximum. (Maximum and minimum values are those compared to adhesion in the absence of compound and in the presence of the dipotassium salt of 2 mM EDTA; Sigma Chemicals, UK, Product No. ED2P). Data is presented as the mean $pIC_{50}$ with the standard error of the mean of n experiments.

(2) CD3/VCAM-1 Co-stimulation of T-Lymphocyte Proliferation

CD4⁺ T-cells were purified from peripheral blood mononuclear cells by negative selection with anti-CD14, CD19, CD16 and HLA.DR antibodies and Dynal beads. Flat bottomed 96-well tissue culture plates were coated with 1 µg ml⁻¹ anti-CD3 antibody (OKT3), washed and incubated with human IgG and zzVCAM-1 fusion proteins. The CD4⁺ T cells (prepared in RPMI-1640 medium supplemented with 10% FCS, penicillin or streptomycin and L-glutamine) were added to the coated plates (1×10⁵ cells well⁻¹) and incubated in the presence or absence of various doses of compound or blocking antibodies for 4 days. Radiolabelled thymidine [³H] was added for the final 6 hours of incubation and the cells were then harvested using a Skatron plate harvester. Incorporation of the [³H] label was measured as an indicator of T cell proliferation using a β plate counter. Compounds were assayed in triplicate and data was collected in an analogous procedure to that described for Assay (1).

(3) Inhibition of Eosinophil Infiltration and Hyper-Reactivity in the Guinea Pig In a method based on that described by Danahay et al., 1997, ovalbumin sensitised guinea pigs were dosed with mepyramine (30 mg kg⁻¹ ip) to protect against anaphylactic bronchospasm. Test compounds, dissolved in 0.9% saline, were given by the inhaled route (30 minutes breathing of an aerosol of the compound) or the intra-tracheal route, 30 minutes before and 6 hours after ovalbumin challenge (10 minutes breathing of an aerosol generated from a 0.5% solution of ovalbumin). Hyper-reactivity of the airways to the thromboxane mimetic U46619, was measured 24 hours after ovalbumin challenge in un-restrained animals using a whole body plethysmograph (Buxco Ltd., USA). The guinea pigs were then sacrificed and the lungs lavaged. Total and differential leukocyte counts were then obtained for the bronchoalveolar lavage fluid and the percentage reduction in eosinophil accumulation determined (Sanjar et al., 1992). Dexamethasone (200 µg kg⁻¹ i.t) was used as a positive control. Data was presented as the inhibitory effect of the specified dose expressed as a percentage of the vehicle control response.

(4) RPMI 8866/MAdCAM-1 Adhesion Assay

This assay was used to investigate the interaction of the integrin $\alpha_4\beta_7$, expressed on the RPMI 8866 (human B lymphoid cell line) cell membrane with MAdCAM-1. Polystyrene 96-well microtitre plates were coated with human immunoglobulin G (IgG; Sigma Chemicals, UK, Product No. 14506) at a concentration of 0.05 mg ml⁻¹ in bicarbonate buffer (36 mM $NaHCO_3$ and 22 mM $Na_2CO_3$, prepared in Dulbecco's phosphate buffered saline at pH 9.8 (PBS); Sigma Chemicals, UK, Product No. 14190-094) for 2 hours at 37° C. This solution was then aspirated and the plates were washed twice with PBS.

MAdCAM-1 was prepared by cloning its constituent domains, under the control of a polyhedrin promoter, into a baculovirus expression system with a zz (Protein A) tag. The amplified baculovirus containing zzMAdCAM-1 was used to infect *Spodoptera frugiperda* cells growing in suspension in SF900II medium supplemented with 5% foetal calf serum. The cells were infected at a multiplicity of infection of 1 and harvested 48 hours later by centrifugation. Protease inhibitors were added and the culture supernatant was clarified either by filtration through a 0.2 µm filter or by centrifugation. The zzMAdCAM-1 was then purified from this clarified medium using an IgG agarose column, equilibrated with either 20 mM sodium phosphate pH 7.2 alone or in the presence of 0.5M sodium chloride. Elution of zzMAdCAM-1 from the column was mediated using 3M ammonium thiocyanate. The sample was then dialysed thoroughly, using 20 mM sodium phosphate pH 7.2, to remove the ammonium thiocyanate. The purified zzMAdCAM-1 was then concentrated to a small volume (Amicon stirred cell concentrators) until a concentration of 0.5 mg ml⁻¹ was obtained, calculated using the extinction coefficient value.

This solution of zzMAdCAM-1 was diluted 1:2500 and then incubated overnight at 4° C. in the IgG coated microtitre plates with 3% bovine serum albumin (BSA) in PBS, followed by aspiration and two further washes with PBS. A concentration of the RPMI 8866 cells (3×10⁶ cells ml⁻¹), grown in cell media RPMI 1640 (HyClone Ltd, Product No. B-9106-L) supplemented with 10% heat inactivated foetal calf serum (FCS; Gibco BRL, Product No. 10099-075) and 2 mM L-glutamine, were labelled with 10 µM of the fluorescent dye, 2', 7'-bis(2-carboxyethyl)-5-(e6)-carboxyfluorescein acetoxymethyl ester (BCECF-AM; Molecular Probes Inc. Product No. B-1150) at 37° C. for 10 minutes. The excess dye was then removed by centrifugation at 500×g for 5 minutes and the cells were resuspended at a concentration of 6×10⁶ cells ml⁻¹ in Hank's balanced salt solution (HBSS; Gibco BRL, Product No. 1419D-094).

Equal volumes of compounds (dissolved in an appropriate solvent and diluted in HBSS containing 1 mM $MnCl_2$) and the labelled RPMI 8866 cells, were added to the MAdCAM-1 coated plates and adhesion was allowed to proceed for 30 minutes at 37° C. Non, or loosely adhered cells, were removed by inversion of the plate and blotted with tissue paper. Two washes with PBS and further blotting were then performed, before the addition of 2% detergent (Triton-X®; Sigma Chemicals UK, Product No. X100). Counting was undertaken in a Wallac Victor™ Fluorimeter, where low fluorescence values were indicative of compounds which had inhibited adhesion. All samples were assayed in singlicate and the following four parameter curve fit, shown by Equation (I) (above) was applied. Wherein the maximum and minimum values are those compared to adhesion in the absence of compound and in the presence of the dipotassium salt of 2 mM EDTA; Sigma Chemicals, UK, Product No. ED2P). Data is presented as the mean $pIC_{50}$ with the standard error of the mean of n experiments.

Examples of disease states in which the compounds of the invention have potentially beneficial anti-inflammatory effects include diseases of the respiratory tract such as bronchitis (including chronic bronchitis), asthma (including allergen-induced asthmatic reactions), chronic obstructive pulmonary disease (COPD) and rhinitis. Other relevant disease states include diseases of the gastrointestinal tract such as intestinal inflammatory diseases including inflammatory bowel disease (e.g. Crohn's disease or ulcerative colitis) and intestinal inflammatory diseases secondary to radiation exposure or allergen exposure. Furthermore, compounds of the invention may be used to treat nephritis, skin diseases such as psoriasis, allergic dermatitis and hypersensitivity reactions and diseases of the central nervous system which have an inflammatory component eg. Alzheimer's disease, meningitis, multiple sclerosis and AIDS dementia.

Further examples of disease states in which compounds of the invention have potentially beneficial effects include cardiovascular conditions such as atherosclerosis, peripheral vascular disease and idiopathic hypereosinophilic syndrome.

Compounds of the invention may be useful as immunosuppressive agents and so have use in the treatment of auto-immune diseases such as allograft tissue rejection after transplantation, rheumatoid arthritis and diabetes.

Compounds of the invention may also be useful in inhibiting metastasis.

Diseases of principal interest include asthma, COPD and inflammatory diseases of the upper respiratory tract involving seasonal and perennial rhinitis.

It will be appreciated by those skilled in the art that reference herein to treatment extends to prophylaxis as well as the treatment of established conditions.

As mentioned above, compounds of formula (I) are useful as pharmaceuticals, in particular as anti-inflammatory agents.

There is thus provided as a further aspect of the invention a compound of formula (I) or a physiologically acceptable salt or solvate thereof for use as pharmaceuticals, particularly in the treatment of patients with inflammatory conditions.

According to another aspect of the invention, there is provided the use of a compound of formula (I) or a physiologically acceptable salt or solvate thereof for the manufacture of a medicament for the treatment of patients with inflammatory conditions.

In a further or alternative aspect there is provided a method for the treatment of a human or animal subject with an inflammatory condition, which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in anti-inflammatory therapy, comprising a compound of formula (I) or a physiologically acceptable salt or solvate thereof together, if desirable, with one or more physiologically acceptable diluents or carriers.

There is also provided a process for preparing such a pharmaceutical formulation which comprises mixing the ingredients.

The compounds according to the invention may, for example, be formulated for oral, buccal, parenteral, topical or rectal administration, preferably for topical administration to the lung, eg. by aerosol or as a dry powder composition.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

By topical administration as used herein, we include administration by insufflation and inhalation. Examples of various types of preparation for topical administration include ointments, creams, lotions, powders, pessaries, sprays, aerosols, capsules or cartridges for use in an inhaler or insufflator, solutions for nebulisation or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents. Powder compositions for inhalation will preferably contain lactose. Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetra-fluoroethane, 1,1,1,2,3,3,3-heptafluoropropane, 1,1,1,2-tetrafluoroethane, carbon dioxide or other suitable gas.

Intranasal sprays may be formulated with aqueous or non-aqueous vehicles with the addition of agents such as thickening agents, buffer salts or acid or alkali to adjust the pH, isotonicity adjusting agents or antioxidants.

Capsules and cartridges of for example gelatin, or blisters of for example laminated aluminium foil, for use in an inhaler or insufflator may be formulated containing a powder mix of a compound of the invention and a suitable powder base such as lactose or starch.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

The pharmaceutical compositions according to the invention may also be used in combination with other therapeutic agents, for example anti-inflammatory agents (such as corticosteroids (eg. fluticasone propionate, beclomethasone dipropionate, mometasone furoate, triamcinolone acetonide or budesonide) or NSAIDs (eg. sodium cromoglycate, nedocromil sodium, PDE-4 inhibitors, leukotriene antagonists, iNOS inhibitors, tryptase and elastase inhibitors, beta-2 integrin antagonists and adenosine 2a agonists)) or beta adrenergic agents (such as salmeterol, salbutamol, formoterol, fenoterol or terbutaline and salts thereof) or antiinfective agents (eg. antibiotics, antivirals).

The invention thus provides, in a further aspect, a combination comprising a compound of formula (I) or a physiologically acceptable salt or solvate thereof together with another therapeutically active agent, for example an anti-inflammatory agent such as a corticosteroid, NSAID, beta adrenergic agent or an anti-infective agent. A pharmaceutical composition comprising a compound of formula (I) or a physiologically acceptable salt or solvate thereof in combination together with a long acting $\beta_2$ adrenergic receptor agonist (eg. salmeterol or a salt or solvate thereof such as salmeterol xinafoate) is of particular interest.

The combination referred to above may conveniently be presented for use in the form of a pharmaceutical formulation and thus pharmaceutical formulations comprising a combination as defined above together with a physiologically acceptable diluent or carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

Compounds of the invention may conveniently be administered in amounts of, for example, 0.001 to 500 mg/kg body weight, preferably 0.01 to 500 mg/kg body weight, more preferably 0.01 to 100 mg/kg body weight, 1 to 4 times daily. The precise dose will of course depend on the age and condition of the patient and the particular route of administration chosen.

The compounds of the invention have the advantage that they may be more efficacious, show greater selectivity (eg. in that they selectively antagonise α4 integrins relative to β2 integrins such as LFA-1 or VLA-5 (αvβ1)), have fewer side effects, have a longer duration of action, be less bioavailable or show less systemic activity when administered by inhalation, have ready and economic synthesis, or have other more desirable properties than similar known compounds.

Certain intermediates are new and provide a further aspect of the invention.

The invention may be illustrated by reference to the following examples:

EXAMPLES

General Experimental Details

Where compounds were purified by "flash column chromatography on silica gel" this refers to the use of silica gel, 0.040 to 0.063 mm mesh (e.g. Merck Art 9385), where column elution is accelerated by an applied pressure of nitrogen at up to 5 p.s.i. Where thin layer chromatography (TLC) has been used this refers to silica gel TLC using 5×10 cm silica gel plates (e.g. Polygram SIL G/UV$_{254}$).

Mass Spectroscopy

Mass Spectrometry (MS) was carried out using an HP5989A Engine Mass Spectrometer connected to a flow inject system (0.05M aqueous ammonium acetate/methanol (35:65) at a flow rate of 0.7 ml/min) with positive thermospray ionisation.

NMR

NMR spectra were run on a Bruker DPX400 400 MHz spectrometer.

LC/MS System

The Liquid Chromatography Mass Spectrometry (LCMS) system used was as follows:

A 3 μm ABZ+PLUS, 3.3 cm×4.6 mm internal diameter column eluting with solvents: A—0.01M Aqueous ammonium acetate+0.1% v/v formic acid, and B—95:5 acetonitrile/water+0.05% v/v formic acid with a flow rate of 3 ml/min. The following gradient protocol was used: 100% A for 0.7 mins; A+B mixtures, gradient profile 0–100% B over 3.7 mins; hold at 100% B for 0.9 mins; return to 0% B over 0.2 mins.

Positive and negative electrospray ionisation was employed.

Protection Measurement

The method for measuring the substitution of Fmoc-amino acid resins was as follows:

To 10 mg of resin was added 20% piperidine in DMF (1 ml). After shaking for 30 mins at 20° C. the resin was filtered. To 50 μL of the filtrate was added 20% piperidine in DMF (0.95 ml) and the absorbance of the solution was measured at 302 nm using a UV spectrophotometer. Substitution was calculated using the following equation:

Substitution (mmol/g)=(Absorbance×2×10$^4$)/(Extinction coefficient×weight in mg)

Intermediates

Intermediate 1

Methyl (2S)-2-({(2S)-2-[(tert-butoxycarbonyl) amino]-4-methyl pentanoyl}amino)-3-(4-hydroxyphenyl)propanoate To a solution of N-(tert-butoxycarbonyl)-L-leucine (7 g) in acetonitrile (100 ml), under a nitrogen atmosphere, was added 1-(3-dimethylaminopropyl)-3-ethylcarbodiimide hydrochloride (5.9 g) and 1-hydroxybenzotriazole (4.2 g). After stirring for 30 mins at 20° C. L-tyrosine methyl ester (5.5 g) was added and stirring was continued for 18 h. The mixture was concentrated in vacuo to ca. 10 ml and the residue was partitioned between 1M hydrochloric acid (200 ml) and ethyl acetate (100 ml). The layers were separated and the aqueous phase was further extracted with ethyl acetate (100 ml). The combined organic extracts were washed with saturated aqueous sodium hydrogen carbonate (100 ml), water (2×100 ml) and brine (50 ml), dried over sodium sulphate and evaporated in vacuo. The residue was co-evaporated with chloroform to give the title compound as a white foam (11.3 g, 98%). LCMS: $R_t$ 3.11 min; m/z 409 (MH$^+$).

Intermediate 2

Methyl (2S)-2-{[(2S)-2-amino-4-methylpentanoyl] amino}-3-(4-hydroxyphenyl)propanoate hydrochloride To a solution of Intermediate 1 (3.1 g) in 1,4-dioxane (10 ml) was added 4M hydrogen chloride in 1,4-dioxane (20 ml). The solution was stirred for 2 h at 20° C. then evaporated in vacuo. The residue was co-evaporated with toluene (2×20 ml) and ether (2×20 ml) to give the title compound as a white solid (2.6 g, 98%). LCMS: $R_t$ 1.98 min; m/z 309 (MH$^+$).

Intermediate 3

Methyl (2S)-3-(4-hydroxyphenyl)-2-({(2S)-4-methyl-2-[(2-{[3-(1-piperidinylcarbonyl)-2-naphthyl]oxy}acetyl)amino]pentanoyl}amino) propanoate To a suspension of Intermediate 44 (0.45 g) in acetonitrile (20 ml), under a nitrogen atmosphere, was added 1-(3-dimethylaminopropyl)-3-ethylcarbodiimide hydrochloride (0.31 g) and 1-hydroxybenzotriazole (0.22 g). After stirring for 30 mins at 20° C. Intermediate 2 (0.5 g) was added followed by diisopropylethylamine (0.28 ml) and stirring was continued for 18 h. The mixture was concentrated in vacuo and the residue was partitioned between 2M hydrochloric acid (50 ml) and ethyl acetate (30 ml). The layers were separated and the aqueous phase was further extracted with ethyl acetate (30 ml). The combined organic extracts were washed with saturated aqueous sodium hydrogen carbonate (30 ml), water (2×30 ml) and brine (20 ml), dried over sodium sulphate and evaporated in vacuo. The crude product was purified by flash column chromatography on silica gel eluting with ethyl acetate/petroleum ether (2:1) to give the title compound as a white foam (0.6 g, 69%). LCMS: $R_t$ 3.42 min; m/z 604 (MH$^+$).

Intermediate 4

Methyl (2S)-3-(4-hydroxyphenyl)-2-[((2S)-2-{[2-(2-iodophenoxy)acetyl]amino}-4-methylpentanoyl) amino]propanoate This was similarly prepared from Intermediate 43 (0.81 g) and Intermediate 2 (1.02 g). The crude product was purified by flash column chromatography on silica gel eluting with ethyl acetate/cyclohexane (1:1) to give the title compound as a white foam (1.2 g, 74%). LCMS: $R_t$ 3.40 min; m/z 569 (MH$^+$).

Intermediate 5

Methyl (2S)-2-({(2S)-2-[(dibenzo[b,d]furan-4-ylcarbonyl)amino]-4-methylpentanoyl}amino)-3-(4-hydroxyphenyl)propanoate This was similarly prepared from Intermediate 45 (0.29 g) and Intermediate 2 (0.5 g). The crude product was purified by flash column chromatography on silica gel eluting with ethyl acetate/cyclohexane (1:1) to give the title compound as a white foam (0.66 g, 97%). LCMS: $R_t$ 3.55 min; m/z 503 (MH$^+$).

Intermediate 6

Methyl (2S)-2-({(2S)-2-[(dibenzo[b,d]furan-4-ylcarbonyl)amino]-4-methylpentanoyl}amino)-3-(4-{[(4-nitrophenoxy)carbonyl]oxy}phenyl)propanoate To a solution of Intermediate 5 (0.59 g) in dichloromethane (5 ml), under a nitrogen atmosphere, was added 4-dimethylaminopyridine (0.18 g). The mixture was cooled to 0–5° C. and 4-nitrophenyl chloroformate (0.3 g) was added. Stirring was continued for 18 h allowing the reaction to warm to 20° C. The solution was diluted with chloroform (60 ml) and washed with 1M hydrochloric acid (2×40 ml) and water (40 ml), dried over magnesium sulphate and evaporated in vacuo. The crude product was purified by flash column chromatography on silica gel eluting with cyclohexane/ethyl acetate (3:2) to give the title compound as a white foam (0.36 g, 46%). LCMS: $R_t$ 3.98 min; m/z 668 (MH$^+$).

Intermediate 7

4-[(2S)-2-({(2S)-2-[(Tert-butoxycarbonyl)amino]-4-methyl pentanoyl}amino)-3-methoxy-3-oxopropyl] phenyl 4-[(2-phenylacetyl)amino]-1-piperidinecarboxylate To a solution of triphosgene (0.59 g) in anhydrous dichloromethane (40 ml), under a nitrogen atmosphere, was added a solution of Intermediate 1 (1.87 g) in anhydrous dichloromethane (10 ml) followed by diisopropylethylamine (1.2 ml). After stirring for 3 h at 20° C. Intermediate 59 (1 g) was added followed by diisopropylethylamine (0.8 ml). Stirring was continued for 18 h then the mixture was evaporated in vacuo. The crude product was purified by flash column chromatography on silica gel eluting with ethyl acetate/cyclohexane (1:1 switching to 5:1) to give the title compound as a white solid (1.76 g, 59%).

LCMS; $R_t$ 3.42 min; m/z 651 [M–H]$^-$.

Intermediate 8

4-((2S)-2-{[(2S)-2-Amino-4-methylpentanoyl] amino}-3-methoxy-3-oxopropyl)phenyl 4-[(2-phenylacetyl)amino]-1-piperidinecarboxylate hydrochloride To a solution of Intermediate 7 (1.76 g) in 1,4-dioxane (10 ml) was added 4M hydrogen chloride in 1,4-dioxane (8 ml). After stirring for 3 h at 20° C. the solvent was evaporated in vacuo and the residue was triturated with ether to give the title compound as a cream solid (1.59 g, 100%). LCMS: $R_t$ 2.50 min; m/z 553 (MH$^+$).

Intermediate 9

Methyl (2S)-2-({(2S)-2-[(tert-butoxycarbonyl) amino]-4-methyl pentanoyl}amino)-3-(4-{[(4-nitrophenoxy)carbonyl]oxy}phenyl)propanoate To a solution of Intermediate 1 (0.41 g) in dichloromethane (3 ml), under a nitrogen atmosphere, was added pyridine (1 ml). The mixture was cooled to 0–5° C. and 4-nitrophenyl chloroformate (0.22 g) was added. Stirring was continued for 18 h allowing the reaction to warm to 20°

C. The solution was diluted with dichloromethane (40 ml) and washed with 1M hydrochloric acid (50 ml). The aqueous phase was further extracted with dichloromethane (40 ml) and the combined organic extracts were dried over sodium sulphate and evaporated in vacuo. The crude product was purified by flash column chromatography on silica gel eluting with petroleum ether/ethyl acetate (3:1 switching to 3:2) to give the title compound as a white solid (0.29 g, 50%). LCMS: $R_t$ 3.39 min; m/z 574 (MH+).

Intermediate 10

4-((2S)-2-{[(2S)-2-Amino-4-methylpentanoyl]
amino}-3-methoxy-3-oxopropyl)phenyl 4-[(2,2-
dicyclohexylacetyl)amino]-1-piperidinecarboxylate
hydrochloride To a solution of Intermediate 9 (0.22 g) in anhydrous dichloromethane (4 ml), under a nitrogen atmosphere, was added Intermediate 58 (0.14 g) followed by diisopropylethylamine (0.08 ml). After stirring for 4 h at 20° C. the mixture was diluted with dichloromethane (50 ml), washed with saturated aqueous potassium carbonate (3×25 ml) and 1M hydrochloric acid (40 ml), dried over sodium sulphate and evaporated in vacuo to give a cream solid. To this was added 4M hydrogen chloride in 1,4-dioxane (3 ml) and the mixture was stirred for 3 h at 20° C. The solvent was evaporated in vacuo and the residue was triturated with ether to give the title compound as a cream solid (0.24 g, 95%). LCMS: $R_t$ 3.05 min; m/z 641 (MH+).

Intermediate 11

Tert-butyl (2S)-2-[((2S)-2-{[(benzyloxy)carbonyl]
amino}-4-methylpentanoyl)amino]-3-(4-
hydroxyphenyl)propanoate To a solution of N-carbobenzyloxy-L-leucine (8.6 g) in acetonitrile (150 ml), under a nitrogen atmosphere, was added 1-(3-dimethylaminopropyl)-3-ethylcarbodiimide hydrochloride (6.83 g) and 1-hydroxybenzotriazole (4.81 g). After stirring for 30 mins at 20° C. L-tyrosine tert-butyl ester (7.7 g) was added and stirring was continued for 18 h. The mixture was concentrated in vacuo to ca. 10 ml and the residue was partitioned between 1M hydrochloric acid (300 ml) and ethyl acetate (150 ml). The layers were separated and the aqueous phase was further extracted with ethyl acetate (150 ml). The combined organic extracts were washed with saturated aqueous sodium hydrogen carbonate (150 ml), water (2×150 ml) and brine (100 ml), dried over sodium sulphate and evaporated in vacuo. The residue was co-evaporated with chloroform to give the title compound as a white foam (15 g, 96%). LCMS: $R_t$ 3.56 min; m/z 485 (MH+).

Intermediate 12

Tert-butyl (2S)-2-[((2S)-2-{[(benzyloxy)carbonyl]
amino}-4-methyl pentanoyl)amino]-3-(4-{[(4-
nitrophenoxy)carbonyl]oxy}phenyl)propanoate To a solution of Intermediate 11 (1.36 g) in dichloromethane (15 ml), under a nitrogen atmosphere, was added 4-nitrophenyl chloroformate (0.75 g) and 4-dimethylaminopyridine (0.47 g). The mixture was stirred for 18 h at 20° C. then diluted with chloroform (50 ml), washed with 1M hydrochloric acid (2×30 ml) and water (30 ml), dried over sodium sulphate and evaporated in vacuo. The crude product was purified by flash column chromatography on silica gel eluting with petroleum ether/ethyl acetate (4:1 switching to 1:1) to give the title compound as a white solid (1.34 g, 74%). LCMS: $R_t$ 3.89 min; m/z 650 (MH+).

Intermediate 13

4-[(2S)-2-[((2S)-2-{[(Benzyloxy)carbonyl]amino}-
4-methyl pentanoyl)amino]-3-(tert-butoxy)-3-
oxopropyl]phenyl 4-morpholinecarboxylate To a solution of Intermediate 12 (0.34 g) in dichloromethane (8 ml), under a nitrogen atmosphere, was added morpholine (0.06 ml) and diisopropylethylamine (0.15 ml). The mixture was stirred for 18 h at 20° C. then diluted with chloroform (30 ml), washed with saturated aqueous potassium carbonate (3×40 ml), 2M hydrochloric acid (40 ml) and water (30 ml), dried over sodium sulphate and evaporated in vacuo. The crude product was purified by flash column chromatography on silica gel eluting with ethyl acetate/petroleum ether (3:2) to give the title compound as a colourless gum (0.31 g, 99%). LCMS: $R_t$ 3.60 min; m/z 598 (MH+).

Intermediate 13 (Alternative Procedure)

4-[(2S)-2-[((2S)-2-{[(Benzyloxy)carbonyl]amino}-
4-methylpentanoyl)amino]-3-(tert-butoxy)-3-
oxopropyl]phenyl 4-morpholinecarboxylate To a solution of triphosgene (2.24 g) in anhydrous dichloromethane (50 ml), under a nitrogen atmosphere, was added a solution of Intermediate 11 (10 g) in anhydrous THF (50 ml) followed by diisopropylethylamine (3.94 ml). After stirring for 4 h at 20° C. morpholine (2 ml) was added followed by diisopropylethylamine (3.94 ml). Stirring was continued for 18 h then the mixture was partitioned between 1M hydrochloric acid (100 ml) and ethyl acetate (75 ml). The layers were separated and the aqueous phase was further extracted with ethyl acetate (75 ml). The combined organic extracts were washed with saturated aqueous sodium hydrogen carbonate (50 ml), water (50 ml) and brine (30 ml), dried over sodium sulphate and evaporated in vacuo. The crude product was purified by flash column chromatography on silica gel eluting with cyclohexane/ethyl acetate (3:1 switching to 1:1) to give the title compound as a white solid (6.8 g, 58%).

Intermediate 14

4-(2S)-[2-[((2S)-2-{[(Benzyloxy)carbonyl]amino}-
4-methyl pentanoyl)amino]-3-(tert-butoxy)-3-
oxopropyl]phenyl 4-(aminocarbonyl)-1-
piperidinecarboxylate This was similarly prepared from Intermediate 11 (9 g) and isonipecotamide (5.2 g). The crude product was purified by flash column chromatography on silica gel eluting with ethyl acetate to give the title compound as a white solid (3.52 g, 30%).

Intermediate 14: (Alternative Procedure)

4-[(2S)-2-[((2S)-2-{[(Benzyloxy)carbonyl]amino}-
4-methyl pentanoyl)amino]-3-(tert-butoxy)-3-
oxopropyl]phenyl 4-(aminocarbonyl)-1-
piperidinecarboxylate To a solution of Intermediate 12 (1 g) in dichloromethane (20 ml), under a nitrogen atmosphere, was added isonipecotamide (0.23 g) and diisopropylethylamine (0.43 ml). The mixture was stirred for 18 h at 20° C. then diluted with chloroform (80 ml), washed with saturated aqueous potassium carbonate (3×50 ml), 2M hydrochloric acid (50 ml) and water (50 ml), dried over sodium sulphate and evaporated in vacuo. The crude product was purified by flash column chromatography on silica gel eluting with petroleum ether/ethyl acetate (3:2) switching to ethyl acetate/methanol (4:1) to give the title compound as a white solid (0.46 g, 47%). LCMS: $R_t$ 3.47 min; m/z 639 (MH$^+$).

Intermediate 15

4-[(2S)-2-{[(2S)-2-Amino-4-methylpentanoyl]amino}-3-(tert-butoxy)-3-oxopropyl]phenyl 4-morpholinecarboxylate To 10% palladium on carbon, Degussa type E101 (0.09 g), under a nitrogen atmosphere, was added a solution of Intermediate 13 (0.3 g) in ethanol (20 ml) followed by ammonium formate (0.17 g). After stirring for 4 h at 20° C. the mixture was filtered through a pad of Harbortite J2 Filter Aid and the pad was washed with ethanol (10 ml). The combined filtrate and washings were evaporated in vacuo and the residue was partitioned between dichloromethane (50 ml) and 1M sodium hydroxide (15 ml). The layers were separated and the organic phase was further washed with 1M sodium hydroxide (15 ml) and water (15 ml), dried over sodium sulphate and evaporated in vacuo to give the title compound as a grey gum (0.1 g, 41%). LCMS: $R_t$ 2.43 min: m/z 464 (MH$^+$).

Intermediate 16

4-[(2S)-2-{[(2S)-2-Amino-4-methylpentanoyl]amino}-3-(tert-butoxy)-3-oxopropyl]phenyl 4-(aminocarbonyl)-1-piperidinecarboxylate This was similarly prepared from Intermediate 14 (0.46 g). The title compound was obtained as a pale yellow gum (0.36 g, 99%). LCMS: $R_t$ 2.33 min; m/z 505 (MH$^+$).

Intermediate 17

4-[(2S)-2-[((2S)-2-{[(Benzyloxy)carbonyl]amino}-4-methyl pentanoyl)amino]-3-(tert-butoxy)-3-oxopropyl]phenyl 4-acetyl-1-piperazine carboxylate To a solution of triphosgene (0.24 g) in anhydrous dichloromethane (5 ml), under a nitrogen atmosphere, was added a solution of Intermediate 11 (1 g) in anhydrous THF (10 ml) followed by diisopropylethylamine (0.43 ml). After stirring for 4 h at 20° C. 1-acetylpiperazine (0.32 g) was added followed by diisopropylethylamine (0.43 ml). Stirring was continued for 18 h then the mixture was partitioned between 1M hydrochloric acid (100 ml) and ethyl acetate (75 ml). The layers were separated and the aqueous phase was further extracted with ethyl acetate (75 ml). The combined organic extracts were washed with saturated aqueous sodium hydrogen carbonate (50 ml), water (50 ml) and brine (30 ml), dried over sodium sulphate and evaporated in vacuo. The crude product was purified by flash column chromatography on silica gel eluting with ethyl acetate switching to ethyl acetate/ethanol (9:1) to give the title compound as a white foam (1.3 g, 99%). LCMS: $R_t$ 3.44 min; m/z 639 (MH$^+$).

Intermediate 18

4-[(2S)-2-[((2S)-2-{[(Benzyloxy)carbonyl]amino}-4-methyl pentanoyl)amino]-3-(tert-butoxy)-3-oxopropyl]phenyl 4-benzoyl-1-piperazine carboxylate To a solution of triphosgene (0.24 g) in anhydrous dichloromethane (5 ml), under a nitrogen atmosphere, was added a solution of Intermediate 11 (1 g) in anhydrous THF (10 ml) followed by diisopropylethylamine (0.43 ml). After stirring for 4 h at 20° C. Intermediate 56 (0.78 g) was added followed by diisopropylethylamine (1.15 ml). Stirring was continued for 18 h then the mixture was partitioned between 1M hydrochloric acid (100 ml) and ethyl acetate (75 ml). The layers were separated and the aqueous phase was further extracted with ethyl acetate (75 ml). The combined organic extracts were washed with saturated aqueous sodium hydrogen carbonate (50 ml), water (50 ml) and brine (30 ml), dried over sodium sulphate and evaporated in vacuo. The crude product was purified by flash column chromatography on silica gel eluting with ethyl acetate/petroleum ether (1:1 switching to 2:1) to give the title compound as a white foam (1.02 g, 71%). LCMS: $R_t$ 3.71 min; m/z 701 (MH$^+$).

Intermediate 19

4-[(2S)-2-[((2S)-2-{[(Benzyloxy)carbonyl]amino}-4-methyl pentanoyl)amino]-3-(tert-butoxy)-3-oxopropyl]phenyl 4-(1-piperidinylcarbonyl)-1-piperidinecarboxylate This was similarly prepared from Intermediate 11 (1.81 g) and Intermediate 55 (0.91 g). The crude product was purified by flash column chromatography on silica gel eluting with dichloromethane/methanol (20:1) to give the title compound as a white foam (1.24 g, 47%). LCMS: $R_t$ 3.63 min; m/z 707 (MH$^+$).

Intermediate 20

4-[(2S)-2-{[(2S)-2-Amino-4-methylpentanoyl]amino}-3-(tert-butoxy)-3-oxopropyl]phenyl 4-(1-piperidinylcarbonyl)-1-piperidinecarboxylate To 10% palladium on carbon, Degussa type E101 (0.27 g), under a nitrogen atmosphere, was added a solution of Intermediate 19 (1.24 g) in ethanol (20 ml) followed by ammonium formate (0.77 g). After stirring for 4 h at 20° C. the mixture was filtered through a pad of Harborlite J2 Filter Aid and the pad was washed with ethanol (20 ml). The combined filtrate and washings were evaporated in vacuo and the residue was partitioned between dichloromethane (50 ml) and 1M sodium hydroxide (15 ml). The layers were separated and the organic phase was further washed with 1M sodium hydroxide (15 ml) and water (15 ml), dried over sodium sulphate and evaporated in vacuo to give the title compound as a white foam (0.55 g, 54%). LCMS: $R_t$ 2.63 min; m/z 573 (MH$^+$).

Intermediate 21

4-[(2S)-2-{[(2S)-2-Amino-4-methylpentanoyl]amino}-3-(tert-butoxy)-3-oxopropyl]phenyl 4-acetyl-1-piperazinecarboxalate hydrochloride To 10% palladium on carbon, Degussa type E101 (0.4 g), under a nitrogen atmosphere, was added a solution of Intermediate 17 (1.28 g) in ethanol (30 ml) followed by ammonium formate (0.38 g). After stirring for 6 h at 20° C. the mixture was filtered through a pad of Harborlite J2 Filter Aid and the pad was washed with ethanol (20 ml). The combined filtrate and washings were evaporated in vacuo and the residue was partitioned between dichloromethane (70 ml) and 1M sodium hydroxide (30 ml). The layers were separated and the aqueous phase was further extracted with dichloromethane (2×50 ml). The combined organic extracts were dried over sodium sulphate. The solution was treated with 4M hydrogen chloride in 1,4-dioxane (0.55 ml) and evaporated in vacuo to give the title compound as a white solid (1.02 g, 94%). LCMS: $R_t$ 2.46 min; m/z 505 (MH$^+$).

Intermediate 22

4-[(2S)-2-{[(2S)-2-Amino-4-methylpentanoyl] amino}-3-(tert-butoxy)-3-oxopropyl]phenyl 4-benzoyl-1-piperazinecarboxylate hydrochloride To 10% palladium on carbon, Degussa type E101 (0.3 g), under a nitrogen atmosphere, was added a solution of Intermediate 18 (1 g) in ethanol (30 ml) followed by ammonium formate (0.27 g). After stirring for 6 h at 20° C. the mixture was filtered through a pad of Harborlite J2 Filter Aid and the pad was washed with ethanol (20 ml). The combined filtrate and washings were evaporated in vacuo and the residue was partitioned between dichloromethane (70 ml) and 1M sodium hydroxide (30 ml). The layers were separated and the aqueous phase was further extracted with dichloromethane (2×50 ml). The combined organic extracts were dried over sodium sulphate. The solution was treated with 4M hydrogen chloride in 1,4-dioxane (0.4 ml) and evaporated in vacuo to give the title compound as a white solid (0.8 g, 100%). LCMS: $R_t$ 2.72 min; m/z 567 (MH$^+$).

Intermediate 23

4-[(2S)-2-{[(2S)-2-Amino-4-methylpentanoyl] amino}-3-(tert-butoxy)-3-oxopropyl]phenyl 4-morpholinecarboxylate hydrochloride To 10% palladium on carbon, Degussa type E101 (2.1 g), under a nitrogen atmosphere, was added a solution of Intermediate 13 (6.8 g) in ethanol (500 ml) followed by ammonium formate (4.1 g). After stirring for 17 h at 20° C. the mixture was filtered through a pad of Harborlite J2 Filter Aid and the pad was washed with ethanol (50 ml). The combined filtrate and washings were evaporated in vacuo and the residue was partitioned between dichloromethane (150 ml) and 1M sodium hydroxide (75 ml). The layers were separated and the aqueous phase was further extracted with dichloromethane (2×100 ml). The combined organic extracts were dried over sodium sulphate. The solution was treated with 1M hydrogen chloride in ether (13 ml) and evaporated in vacuo. The residue was triturated with ether to give the title compound as a white solid (4.8 g, 87%). LCMS: $R_t$ 2.50 min; m/z 464 (MH$^+$).

Intermediate 24

4-[(2S)-2-{[(2S)-2-Amino-4-methylpentanoyl] amino}-3-(tert-butoxy)-3-oxopropyl]phenyl 4-(aminocarbonyl)-1-piperidinecarboxylate hydrochloride To 10% palladium on carbon, Degussa type E101 (1.1 g), under a nitrogen atmosphere, was added a solution of Intermediate 14 (3.41 g) in ethanol (80 ml) followed by ammonium formate (2.1 g). After stirring for 3 h at 20° C. the mixture was filtered through a pad of Harborlite J2 Filter Aid and the pad was washed with ethanol (40 ml). The combined filtrate and washings were evaporated in vacuo and the residue was partitioned between chloroform (500 ml) and saturated aqueous sodium hydrogen carbonate (200 ml). The layers were separated and the aqueous phase was further extracted with chloroform (2×100 ml). The combined organic extracts were washed with saturated aqueous sodium hydrogen carbonate (3×100 ml) and water (2×100 ml) then dried over sodium sulphate. The solution was treated with 4M hydrogen chloride in 1,4-dioxane (1.5 ml) and evaporated in vacuo. The residue was azeotroped with toluene (2×50 ml) to give the title compound as a white solid (2.88 g, 100%). LCMS: $R_t$ 2.36 min; m/z 505 (MH$^+$).

Intermediate 25

Tert-butyl (2S)-2-{[(2S)-2-({2-[2-(tert-butyl) phenoxy]acetyl}amino)-4-methylpentanoyl]amino}-3-(4-hydroxyphenyl)propanoate To 10% palladium on carbon, Degussa type E101 (0.63 g), under a nitrogen atmosphere, was added a solution of Intermediate 11 (2 g) in ethanol (20 ml) followed by ammonium formate (1.8 g). After stirring for 2 h at 20° C. the mixture was filtered through a pad of Harborlite J2 Filter Aid and the pad was washed with ethanol (50 ml). The combined filtrate and washings were evaporated in vacuo and the residue was partitioned between dichloromethane (100 ml) and saturated aqueous sodium hydrogen carbonate (50 ml). The layers were separated and the organic phase was further washed with saturated aqueous sodium hydrogen carbonate (50 ml) and water (50 ml), dried over magnesium sulphate and evaporated in vacuo to give a white solid. A solution of this in DMF (5 ml) was added to a pre-mixed solution of Intermediate 46 (0.879 g), 1-(3-dimethylaminopropyl)-3-ethylcarbodiimide hydrochloride (0.809 g) and 1-hydroxybenzotriazole (0.578 g) in acetonitrile (10 ml) which had been stirring under a nitrogen atmosphere for 30 mins at 20° C. Stirring was continued for 18 h. The mixture was diluted with ethyl acetate (200 ml), washed with 1M hydrochloric acid (3×50 ml), saturated aqueous sodium hydrogen carbonate (3×50 ml) and brine (50 ml), dried over magnesium sulphate and evaporated in vacuo to give the title compound as a white foam (2.1 g, 94%). LCMS: $R_t$ 3.83 min; m/z 541 (MH$^+$).

Intermediate 26

Tert-butyl (2S)-2-{[(2S)-2-({2-[2-(tert-butyl) phenoxy]acetyl}amino)-4-methylpentanoyl]amino}-3-(4-{[(4-nitrophenoxy)carbonyl]oxy}phenyl) propanoate To a solution of Intermediate 25 (2.1 g) in dichloromethane (20 ml), under a nitrogen atmosphere, was added 4-nitrophenyl chloroformate (1.1 g) and 4-dimethylaminopyridine (0.69 g). The mixture was stirred for 18 h at 20° C. then diluted with chloroform (80 ml), washed with 1M hydrochloric acid (2×50 ml) and water (50 ml), dried over magnesium sulphate and evaporated in vacuo. The crude product was purified by flash column chromatography on silica gel eluting with cyclohexane/ethyl acetate (2:1) to give the title compound as a clear oil (2.65 g, 97%). LCMS: $R_t$ 4.17 min; m/z 706 (MH$^+$).

Intermediate 27

4-[(2S)-2-({(2S)-2-[(2-Bromoacetyl)amino]-4-methylpentanoyl}amino)-3-(tert-butoxy)-3-oxopropyl]phenyl 4-morpholinecarboxylate A solution of Intermediate 23 (0.5 g) and diisopropylethylamine (0.19 ml) in dichloromethane (10 ml) was cooled to 0–5° C. To this was added bromoacetyl chloride (0.09 ml) followed by diisopropylethylamine (0.19 ml) and stirring was continued for 2 h. The mixture was diluted with dichloromethane (50 ml), washed with 2M hydrochloric acid (50 ml), saturated aqueous sodium hydrogen carbonate (50 ml) and brine (30 ml), dried over magnesium sulphate and evaporated in vacuo to give the title compound as a white foam (0.52 g, 89%).

LCMS: $R_t$ 3.28 min; m/z 584 (MH$^+$).

Intermediate 28

4-[(2S)-2-({(2S)-2-[(2-Bromoacetyl)amino]-4-methylpentanoyl}amino)-3-methoxy-3-oxopropyl] phenyl 4-[(2-phenylacetyl)amino]-1-piperidine carboxylate To a solution of Intermediate 8 (0.48 g) in anhydrous dichloromethane (4 ml) was added diisopropylethylamine (0.142 ml). The mixture was cooled to 0–5° C. and bromoacetyl chloride (0.07 ml) was added. Stirring was continued for 1 h allowing the reaction to warm to 20° C. The mixture was diluted with dichloromethane (5 ml) and washed with saturated aqueous sodium hydrogen carbonate (5 ml), water (10 ml) and brine (10 ml), dried over sodium sulphate and evaporated in vacuo to give the title compound as a white solid (0.464 g, 85%). LCMS: $R_t$ 3.20 min; m/z 672 [M–H]$^-$.

Intermediate 29

(2S)-3-[4-(Allyloxy)phenyl]-2-{[(9H-fluoren-9-ylmethoxy)carbonyl]amino}propanoic acid bound to Wang resin via acid To Wang resin (100–200 mesh, 10 g) was added a solution of (2S)-3-[4-(allyloxy)phenyl]-2-{[(9H-fluoren-9-ylmethoxy)carbonyl]amino}propanoic acid (8.5 g) in DMF (45 ml). After 15 mins pyridine (2.4 ml) was added followed by 2,6-dichlorobenzoyl chloride (2.75 ml). The mixture was shaken for 18 h at 20° C. The resin was filtered and washed with DMF (5×40 ml), dichloromethane (5×40 ml) and ether (5×40 ml) then dried in vacuo. The amount of (2S)-3-[4-(allyloxy)phenyl]-2-{[(9H-fluoren-9-ylmethoxy)carbonyl] amino}propanoic acid substituted on the resin was calculated to be 0.52 mmol/g.

Intermediate 30

(2S)-3-[4-(Allyloxy)phenyl]-2-[((2S)-2-{[(9H-fluoren-9-ylmethoxy)carbonyl]amino}-4-methylpentanoyl)amino]propanoic acid bound to Wang resin via acid Intermediate 29 (2.5 mmol) was treated with 20% piperidine in DMF (15 ml) and shaken for 1 h 30 mins at 20° C. The resin was filtered and washed with DMF (5×20 ml). A solution of Fmoc-leucine (2.8 g) in DMF (10 ml) was added followed by a solution of benzotriazol-1-yl-oxy-trispyrrolidinophosphonium hexafluoro phosphate (4.1 g) in DMF (5 ml) and diisopropylethylamine (2.8 ml). The mixture was shaken for 18 h at 20° C. The resin was filtered and washed with DMF (5×20 ml), dichloromethane (5×20 ml) and ether (5×20 ml) then dried in vacuo. A 5 mg sample was treated with trifluoroacetic acid/dichloromethane (1:1) (1 ml) for 0.5 h at 20° C., resin was filtered and the filtrate analysed by LCMS: $R_t$ 4.22 min; m/z 557 (MH$^+$).

Intermediate 31

(2S)-3-[4-(Allyloxy)phenyl]-2-{[(2S)-2-({2-[2-(tert-butyl)phenoxy]acetyl}amino)-4-methylpentanoyl]amino}propanoic acid bound to Wang resin via acid Intermediate 30 (1 mmol) was treated with 20% piperidine in DMF (10 ml) and shaken for 1 h at 20° C. The resin was filtered and washed with DMF (5×10 ml). A solution of Intermediate 46 (0.314 g) in DMF (10 ml) was added followed by a solution of benzotriazol-1-yl-oxy-trispyrrolidinophosphonium hexafluoro phosphate (0.78 g) in DMF (5 ml) and diisopropylethylamine (0.68 ml). The mixture was shaken for 18 h at 20° C. The resin was filtered and washed with DMF (5×10 ml), dichloromethane (5×10 ml) and ether (5×10 ml) then dried in vacuo. A 5 mg sample was treated with trifluoroacetic acid/dichloromethane (1:1) (1 ml) for 0.5 h at 20° C., resin was filtered and the filtrate analysed by LCMS: $R_t$ 4.27 min; m/z 525 (MH$^+$).

Intermediate 32

(2S)-3-[4-(Allyloxy)phenyl]-2-[((2S)-4-methyl-2-{[2-(2-methyl phenoxy)acetyl]amino}pentanoyl) amino]propanoic acid bound to Wang resin via acid This was similarly prepared from Intermediate 30 (0.97 mmol) and (2-methylphenoxy)acetic acid (0.48 g). LCMS: $R_t$ 3.89 min; m/z 483 (MH$^+$).

Intermediate 33

(2S)-2-{[(2S)-2-({2-[2-(Tert-butyl)phenoxy] acetyl}amino)-4-methylpentanoyl]amino}-3-(4-{[(4-nitrophenoxy)carbonyl]oxy}phenyl)propanoic acid bound to Wang resin via acid Intermediate 31 (1 mmol) was treated with a solution of phenylsilane (1 ml) in dichloromethane (9 ml) followed by tetrakis(triphenylphosphine)palladium(0) (0.1 g). The mixture was shaken for 40 mins at 20° C. The resin was filtered and washed with dichloromethane (5×10 ml) then retreated with a solution of phenylsilane (1 ml) in dichloromethane (9 ml) followed by tetrakis(triphenylphosphine)palladium(0) (0.1 g). After shaking for 40 mins at 20° C. the resin was filtered and washed with dichloromethane (5×10 ml) then treated with a solution of diisopropylethylamine (1.74 ml) in 1:1 dichloromethane/THF (16 ml). 4-Nitrophenyl chloroformate (2 g) was added portionwise and the mixture was shaken for 18 h at 20° C. The resin was filtered and washed with dichloromethane (5×10 ml) and ether (5×10 ml) then dried in vacuo. A 5 mg sample was treated with trifluoroacetic acid/dichloromethane (1:1) (1 ml) for 0.5 h at 20° C., resin was filtered and the filtrate analysed by LCMS: $R_t$ 4.33 min; m/z 650 (MH$^+$).

Intermediate 34

(2S)-2-[((2S)-4-Methyl-2-{[2-(2-methylphenoxy) acetyl]amino}pentanoyl)amino]-3-(4-{[(4-nitrophenoxy)carbonyl]oxy}phenyl)propanoic acid bound to Wang resin via acid This was similarly prepared from Intermediate 32 (0.97 mmol). LCMS: $R_t$ 3.31 min; m/z 443 (MH$^+$).

Intermediate 35

(2S)-2-[((2S)-2-{[(9H-Fluoren-9-ylmethoxy) carbonyl]amino}-4-methylpentanoyl)amino]-3-(4-{[(4-nitrophenoxy)carbonyl]oxy}phenyl)propanoic acid bound to Wang resin via acid This was similarly prepared from Intermediate 30 (1.05 mmol). LCMS: $R_t$ 4.32 min; m/z 682 (MH$^+$).

Intermediate 36

(2S)-2-[((2S)-2-{[(9H-Fluoren-9-ylmethoxy) carbonyl]amino}-4-methylpentanoyl)amino]-3-[4-({ [4-(2-furoyl)-1-piperazinyl]carbonyl}oxy)phenyl] propanoic acid bound to Wang resin via acid Intermediate 35 (1.05 mmol) was treated with a solution of 1-(2-furoyl)piperazine (0.57 g) in 1:1 dichloromethane/

THF (9 ml) followed by diisopropylethylamine (1.1 ml). After shaking for 4 h at 20° C. the resin was filtered and washed with dichloromethane (5×10 ml) and ether (5×10 ml) then dried in vacuo. A 5 mg sample was treated with trifluoroacetic acids dichloromethane (1:1) (1 ml) for 0.5 h at 20° C., resin was filtered and the filtrate analysed by LCMS: $R_t$ 3.67 min; m/z 723 (MH$^+$).

Intermediate 37

(2S)-3-(4-{[(4-{[2-(4-Chlorophenyl)acetyl]amino}-1-piperidinyl)carbonyl]oxy}phenyl)-2-[((2S)-2-{[(9H-fluoren-9-ylmethoxy)carbonyl]amino}-4-methylpentanoyl)amino]propanoic acid bound to Wang resin via acid This was similarly prepared from Intermediate 35 (1.7 mmol) and Intermediate 53 (1.02 g). LCMS: $R_t$ 4.03 min; m/z 795 (MH$^+$).

Intermediate 38

(2S)-2-({(2S)-2-[(2-Bromoacetyl)amino]-4-methylpentanoyl}amino)-3-[4-({[4-(2-furoyl)-1-piperazinyl]carbonyl}oxy)phenyl]propanoic acid bound to Wang resin via acid Intermediate 36 (1.05 mmol) was treated with 20% piperidine in DMF (8 ml) and shaken for 1 h 30 mins at 20° C. The resin was filtered and washed with DMF (5×10 ml). A solution of bromoacetic acid (0.44 g) in DMF (8 ml) was added followed by 1,3-diisopropylcarbodiimide (0.49 ml). The mixture was shaken for 18 h at 20° C. The resin was filtered and washed with DMF (5×10 ml), dichloromethane (5×10 ml) and ether (5×10 ml) then dried in vacuo. A 5 mg sample was treated with trifluoroacetic acid/dichloromethane (1:1) (1 ml) for 0.5 h at 20° C., resin was filtered and the filtrate analysed by LCMS: $R_t$ 3.11 min; m/z 621 (MH$^+$).

Intermediate 39

(2S)-2-({(2S)-2-[(2-Bromoacetyl)amino]-4-methylpentanoyl}amino)-3-(4-{[(4-{[2-(4-chlorophenyl)acetyl]amino}-1-piperidinyl)carbonyl]oxy}phenyl)propanoic acid bound to Wang resin via acid This was similarly prepared from Intermediate 37 (0.73 mmol). LCMS: $R_t$ 3.43 min; m/z 695 (MH$^+$).

Intermediate 40

(2S)-3-[4-(Allyloxy)phenyl]-2-({(2S)-2-[(2-bromoacetyl)amino]-4-methylpentanoyl}amino)propanoic acid bound to Wang resin via acid Intermediate 30 (0.55 mmol) was treated with 20% piperidine in DMF (6 ml) and shaken for 1 h at 20° C. The resin was filtered and washed with DMF (5×10 ml). A solution of bromoacetic acid (0.23 g) in DMF (3 ml) was added followed by 1,3-diisopropylcarbodiimide (0.26 ml). The mixture was shaken for 18 h at 20° C. The resin was filtered and washed with DMF (5×10 ml), dichloromethane (5×10 ml) and ether (5×10 ml) then dried in vacuo. A 5 mg sample was treated with trifluoroacetic acid/dichloromethane (1:1) (1 ml) for 0.5 h at 20° C., resin was filtered and the filtrate analysed by LCMS: $R_t$ 3.47 min; m/z 455 (MH$^+$).

Intermediate 41

(2S)-3-[4-(Allyloxy)phenyl]-2-[((2S)-2-{[2-(2-cyclohexylphenoxy)acetyl]amino}-4-methylpentanoyl)amino]propanoic acid bound to Wang resin via acid Intermediate 40 (0.55 mmol) was treated with DMF (4 ml). 2-Cyclohexylphenol (0.97 g), potassium carbonate (0.76 g) and sodium iodide (0.82 g) were added and the mixture was shaken for 40 h at 20° C. The resin was filtered and washed with water (3×5 ml), DMF (5×5 ml), dichloromethane (5×5 ml) and ether (5×5 ml) then dried in vacuo. A 5 mg sample was treated with trifluoroacetic acid/dichloromethane (1:1) (1 ml) for 0.5 h at 20° C., resin was filtered and the filtrate analysed by LCMS: $R_t$ 4.49 min; m/z 551 (MH$^+$).

Intermediate 42

(2S)-2-[((2S)-2-{[2-(2-Cyclohexylphenoxy)acetyl]amino}-4-methylpentanoyl)amino]-3-(4-{[(4-nitrophenoxy)carbonyl]oxy}phenyl)propanoic acid bound to Wang resin via acid Intermediate 41 (0.55 mmol) was treated with a solution of phenylsilane (1.35 ml) in dichloromethane (10 ml) followed by tetrakis(triphenylphosphine)palladium(0) (0.063 g). The mixture was shaken for 40 mins at 20° C. The resin was filtered and washed with dichloromethane (5×10 ml) then retreated with a solution of phenylsilane (1.35 ml) in dichloromethane (10 ml) followed by tetrakis(triphenylphosphine)palladium(0) (0.063 g). After shaking for 40 mins at 20° C. the resin was filtered and washed with dichloromethane (5×10 ml) then treated with a solution of diisopropylethylamine (1.9 ml) in 1:1 dichloromethane/THF (8 ml). 4-Nitrophenyl chloroformate (2.2 g) was added portionwise and the mixture was shaken for 18 h at 20° C. The resin was filtered and washed with dichloromethane (5×10 ml) and ether (5×10 ml) then dried in vacuo. A 5 mg sample was treated with trifluoroacetic acid/dichloromethane (1:1) (1 ml) for 0.5 h at 20° C., resin was filtered and the filtrate analysed by LCMS: $R_t$ 4.54 min; m/z 676 (MH$^+$).

Intermediate 43

(2-Iodophenoxy)acetic acid tert-Butyl bromoacetate (4.0 ml) was added to a suspension containing 2-iodophenol (4.98 g) and potassium carbonate (6.3 g) in DMF (40 ml). The mixture was stirred for 1 h at 20° C. under a nitrogen atmosphere and was then partitioned between ethyl acetate (150 ml) and water (100 ml). The aqueous layer was extracted with fresh ethyl acetate (2×80 ml) and the combined organic extracts washed with brine (100 ml), dried over magnesium sulphate and evaporated in vacuo to give a clear liquid (7.56 g). This was dissolved in dichloromethane (20 ml) and trifluoroacetic acid (5 ml) and the solution stirred for 2 h at 20° C. Solvent was evaporated in vacuo and the residue triturated in a mixture of cyclohexane/ethyl acetate (5:1) to give the title compound as a white solid (5.19 g, 82%). LCMS: $R_t$ 3.02 min; m/z 277 [M–H]$^-$.

Intermediate 44

{[3-(1-Piperidinylcarbonyl)-2-naphthyl]oxy}acetic acid

This was similarly prepared from 3-(1-piperidinylcarbonyl)-2-naphthol (Griffiths and Hawkins, 1977) (4.98 g). The intermediate ester was purified by flash column chromatography on silica gel eluting with ethyl acetate/cyclohexane (1:1) and the title compound was isolated as a white solid (3.2 g, 53%). LCMS: $R_t$ 3.74 min; m/z 314 (MH$^+$).

Intermediate 45

Dibenzo[b,d]furan-4-carboxylic acid

A solution of 1.6M n-butyllithium in hexane (18.5 ml) was added dropwise to a stirred solution of dibenzofuran (5.0 g) in anhydrous THF (25 ml) at −78° C. under a nitrogen atmosphere. The resulting suspension was allowed to warm to 20° C. where it was stirred for 3 h. It was then cooled to −78° C. and added to a mixture of excess solid carbon dioxide in diethyl ether (250 ml) under a nitrogen atmosphere. The resulting white suspension was allowed to stand for 1 h at 20° C. and was then diluted with 2M sodium hydroxide (500 ml). The aqueous extract was washed with ether (3×200 ml), acidified to pH 1 with 6M hydrochloric acid and extracted with ethyl acetate (3×200 ml). The combined organic extracts were washed with brine (50 ml), dried over magnesium sulphate and evaporated in vacuo to give the title compound as a white solid (3.64 g, 58%). LCMS: $R_t$ 5.06 min; m/z 213 (MH$^+$).

Intermediate 46

[2-(Tert-butyl)phenoxy]acetic acid

Methyl bromoacetate (3.0 ml) was added to a suspension containing 2-tert-butylphenol (5.0 ml) and potassium carbonate (10.6 g) in DMF (250 ml). The mixture was stirred for 20 h at 20° C. under a nitrogen atmosphere and was then evaporated in vacuo to a slurry which was partitioned between ether (200 ml) and 1M hydrochloric acid (100 ml). The aqueous layer was extracted with more ether (100 ml) and the combined organic extracts washed with brine (100 ml), dried over magnesium sulphate and evaporated in vacuo. The crude material was purified by flash column chromatography on silica gel eluting with ethyl acetate/cyclohexane (1:9) to give a clear liquid (6.64 g). This was dissolved in methanol (100 ml) and 2M sodium hydroxide (100 ml) and the solution was stirred for 0.5 h at 20° C. The methanol was evaporated in vacuo and the aqueous residue was washed with diethyl ether (50 ml), acidified to pH 1 with 6M hydrochloric acid and extracted with ethyl acetate (2×200 ml). The combined organic extracts were washed with brine (50 ml), dried over magnesium sulphate and evaporated in vacuo to give the title compound as a white crystalline mass (5.86 g, 95%). LCMS: $R_t$ 3.78 min; m/z 207 [M−H]$^−$.

Intermediate 47

4-(2-Methoxy-2-oxoethoxy)benzoic acid

Methyl bromoacetate (1.6 ml) was added to a suspension containing tert-butyl 4-hydroxybenzoate (Shah et al., 1992) (3.03 g), sodium iodide (2.55 g) and potassium carbonate (4.2 g) in acetonitrile (60 ml). The mixture was stirred for 17 h at 90° C. under a nitrogen atmosphere and then allowed to cool to 20° C. It was then partitioned between water (50 ml) and ethyl acetate (100 ml) and the organic extract washed with water (2×80 ml) and brine (60 ml), dried over magnesium sulphate and evaporated in vacuo. The crude material was purified by flash column chromatography on silica gel eluting with a gradient of ethyl acetate/petroleum ether (1:9) to ethyl acetate/petroleum ether (1:2) to give a pale red gum (3.85 g). This was dissolved in dichloromethane (50 ml) and trifluoroacetic acid (15 ml) was added and the solution was stirred for 3 h at 20° C. Solvents were evaporated in vacuo to give the title compound as a white solid (2.97 g, 91%). LCMS: $R_t$ 2.45 min; m/z 211 (MH$^+$).

Intermediate 48

[4-(1-Piperidinylcarbonyl)phenoxy]acetic acid

To a suspension of Intermediate 47 (2.95 g) in acetonitrile (55 ml) was added diisopropylethylamine (3.5 ml) followed by (1H-benzotriazol-1-yl)-1,1,3,3-tetramethyluronium tetrafluoroborate (4.5 g). The resulting solution was stirred for 10 mins at 20° C. under a nitrogen atmosphere and then piperidine (1.4 ml) was added and the mixture was stirred for 18 h at 20° C. under a nitrogen atmosphere and then evaporated in vacuo. The residue was partitioned between ethyl acetate (100 ml) and 8% aqueous sodium hydrogen carbonate (65 ml) and the organic extract was washed with 2M hydrochloric acid (50 ml) and brine (100 ml), dried over magnesium sulphate and evaporated in vacuo to give an orange oil (4.05 g). This was dissolved in methanol (100 ml) and 1M sodium hydroxide (30 ml) was added and the mixture stirred for 3 h at 20° C. It was then acidified to pH 1 with 1M hydrochloric acid and cooled to 5° C. and the precipitate collected by filtration and dried in vacuo to give the title compound as a white solid (3.03 g, 80%). LCMS: $R_t$ 4.17 min; m/z 264 (MH$^+$).

Intermediate 49

(2-Benzoylphenoxy)acetic acid

Methyl bromoacetate (3.0 ml) was added to a suspension containing 2-hydroxybenzophenone (2.3 g), potassium carbonate (3.2 g) and sodium iodide (2.33 g) in acetonitrile (35 ml). The mixture was stirred for 18 h at 90° C. under a nitrogen atmosphere and was then allowed to cool to 20° C. It was then partitioned between ethyl acetate (80 ml) and water (60 ml) and the organic extract washed with water (2×60 ml) and brine (60 ml), dried over magnesium sulphate and evaporated in vacuo. The crude material was purified by flash column chromatography on silica gel eluting with ethyl acetate/petroleum ether (1:1) to give a pale yellow oil (3.05 g). This was dissolved in methanol (100 ml) and 1M sodium hydroxide (35 ml) and the solution was stirred for 18 h at 20° C. The solution was acidified to pH 1 with 2M hydrochloric acid and extracted with ethyl acetate (2×80 ml). The combined organic extracts were washed with water (2×70 ml), dried over magnesium sulphate and evaporated in vacuo. The crude product was purified by flash column chromatography on silica gel eluting with a gradient of ethyl acetate/petroleum ether (1:1) to ethyl acetate/methanol (4:1) to give the title compound as a pale yellow gum (1.62 g, 57%). LCMS: $R_t$ 3.41 min; m/z 257 (MH$^+$).

Intermediate 50

[(1-Bromo-2-naphthyl)oxy]acetic acid

This was similarly prepared from 1-bromo-2-naphthol (10.55 g). The intermediate ester was purified by flash column chromatography on silica gel eluting with ethyl acetate/cyclohexane (1:3) and the title compound was isolated as a pale brown solid (11.36 g, 89%). LCMS: $R_t$ 4.17 min; m/z 281 [M−H]$^−$.

Intermediate 51

[4-(Aminocarbonyl)phenoxy]acetic acid

A solution of 4-formylphenoxyacetic acid (1.86 g) and hydroxylamine hydrochloride (1.07 g) in 98% formic acid (50 ml) was stirred under reflux for 2 h and then cooled in an ice bath. The precipitate was collected by filtration, washed with water and dried in vacuo to give a white solid (1.1 g). A mixture of this with powdered potassium hydroxide (2.3 g) in tert-butanol (50 ml) was stirred under reflux under a nitrogen atmosphere for 4 h and then allowed to cool. The mixture was diluted with water (100 ml), washed with ethyl acetate (50 ml) and acidified to pH 2 with 6M hydrochloric acid. The precipitate was collected by filtration, washed with water and dried in vacuo to give the title compound as a white solid (1.06 g, 53%). LCMS: $R_t$ 1.90 min; m/z 196 (MH$^+$).

Intermediate 52

Tert-butyl 4-amino-1-piperidinecarboxylate

Sodium triacetoxyborohydride (30.2 g) was added portionwise over 10 min to an ice-cooled mixture of 1-(tert-butoxycarbonyl)-4-piperidone (20.07 g), dibenzylamine (19.7 g) and acetic acid (5 ml) in dichloromethane (500 ml) and stirring was then continued for 16 h at 20° C. The solution was then treated cautiously with 2M sodium hydroxide (400 ml) and the separated organic layer, dried over magnesium sulphate and evaporated in vacuo. The residue was triturated in hexane/ether (2:1) (250 ml) to give a white solid (18.75 g). This was dissolved in a mixture of THF (50 ml), ethanol (50 ml) and 2M hydrochloric acid (8 ml) and the solution added to a suspension of 20% palladium hydroxide on carbon (5.0 g) in ethanol (100 ml). The mixture was hydrogenated at 20° C. and 1 atmosphere for 17 h and was then filtered through a pad of Harborlite J2 Filter Aid and the pad washed with ethanol (100 ml). The combined filtrate and washings were evaporated in vacuo and the residue dissolved in water (50 ml) and adjusted to pH 9 with 2M sodium hydroxide and evaporated in vacuo. The residue was leached into a mixture of ethanol (30 ml) and chloroform (70 ml) and insoluble material removed by filtration. The mother liquors were evaporated in vacuo to give the title compound as a colourless oil (10.04 g, 49%). LCMS: $R_t$ 1.81 min; m/z 201 (MH$^+$).

Intermediate 53

2-(4-Chlorophenyl)-N-(4-piperidinyl)acetamide hydrochloride

To a solution of 4-chlorophenylacetic acid (2.55 g) in acetonitrile (100 ml), under a nitrogen atmosphere, was added 1-(3-dimethylaminopropyl)-3-ethylcarbodiimide hydrochloride (3.16 g) and 1-hydroxybenzotriazole (2.22 g). After stirring for 10 mins at 20° C. a solution of Intermediate 52 (3 g) in acetonitrile (20 ml) was added, and stirring was continued for 18 h. The mixture was evaporated in vacuo and the residue partitioned between water (100 ml) and ethyl acetate (100 ml). The organic phase was washed with saturated aqueous sodium hydrogen carbonate (2×80 ml) and water (50 ml), dried over magnesium sulphate and evaporated in vacuo to give a pale yellow solid. This was triturated with ether to give a white solid (4.15 g). A portion of this (2.36 g) was dissolved in 1,4-dioxane (100 ml) and 4M hydrogen chloride in 1,4-dioxane (12 ml) was added. The solution was stirred for 18 h at 20° C. and then a further portion of 4M hydrogen chloride in 1,4-dioxan (8 ml) was added. Stirring was continued for a further 18 h at 20° C. and the solution was evaporated in vacuo to give a white solid. This was triturated in ether to give the title compound as a white solid (1.9 g, 77%). LCMS: $R_t$ 1.89 min; m/z 253 (MH$^+$).

Intermediate 54

N-(4-Fluorobenzyl)-4-piperidinecarboxamide hydrochloride

To a solution of 1-tert-butoxycarbonylpiperidine-4-carboxylic acid (3.61 g) in acetonitrile (25 ml), under a nitrogen atmosphere, was added 1-(3-dimethylaminopropyl)-3-ethylcarbodiimide hydrochloride (3.21 g) and 1-hydroxybenzotriazole (2.29 g). After stirring for 20 mins at 20° C. fluorobenzylamine (2.0 ml) was added and stirring was continued for 3 h. The mixture was concentrated in vacuo and the residue was partitioned between 1M hydrochloric acid (50 ml) and thyl acetate (200 ml). The layers were separated and the organic phase was washed with 1M hydrochloric acid (3×50 ml), saturated aqueous sodium hydrogen carbonate (3×50 ml) and brine (50 ml), dried over magnesium sulphate and evaporated in vacuo. The crude material was purified by flash column chromatography on silica gel eluting with a gradient of cyclohexanelethyl acetate (1:1) to neat ethyl acetate to give colourless crystals (5.02 g). A portion of this (4.96 g) was dissolved in 1,4-dioxane (20 ml) and 4M hydrogen chloride in 1,4-dioxane (15 ml) was added. The mixture was stirred for 2 h at 20° C. and the precipitate was collected by filtration, washed with 1,4-dioxane and diethyl ether and dried in vacuo to give the title compound as a white hygroscopic solid (3.54 g, 83%). LCMS: $R_t$ 1.52 min; m/z 237 (MH$^+$).

Intermediate 55

1-(4-Piperidinylcarbonyl)piperidine hydrochloride

This was similarly prepared from 1-tert-butoxycarbonylpiperidine-4-carboxylic acid (3.68 g) and piperidine (1.6 ml). The intermediate amide was purified by flash column chromatography on silica gel eluting with dichloromethane/methanol (10:1) and the title compound was isolated as a white solid (3.26 g, 93%). MS: m/z 197 (MH$^+$), TLC; $R_t$ 0.1 [dichloromethane/ethanol/880 ammonia (50:8:1) visualisation with iodoplatinic acid].

Intermediate 56

1-Benzoylpiperazine

This was similarly prepared from benzoic acid (5.02 g) and 1-(tert-butoxycarbonyl)piperazine (7.66 g) and the title compound was isolated as a white solid (7.7 g, 82%). LCMS: $R_t$ 0.51 min; m/z 191 (MH$^+$).

Intermediate 57

2-Cyclohexyl-N-(4-piperidinyl)acetamide

A solution of 4-amino-1-benzylpiperidine (5.0 ml), cyclohexaneacetic acid (3.79 g) and (1H-benzotriazol-1-yl)-1,1,3,3-tetramethyluronium tetrafluoroborate (8.35 g) in acetonitrile (60 ml) was stirred for 18 h at 20° C. under a nitrogen atmosphere and was then evaporated in vacuo to a syrup. This was partitioned between ethyl acetate (200 ml) and saturated aqueous sodium hydrogen carbonate (200 ml). The organic extract was washed with saturated aqueous sodium hydrogen carbonate (2×100 ml) and brine (100 ml), dried over magnesium sulphate and evaporated in vacuo to give an off-white solid. This was crystallised from cyclohexane to give cream crystals (6.24 g). A portion of this (3.8 g) was dissolved in ethanol (100 ml) and treated with 10% palladium on carbon, Degussa type E101 (1.2 g) and ammonium formate (2.24 g). The mixture was stirred for 2.5 h at 20° C. under a nitrogen atmosphere and was then filtered through a pad of Harborlite J2 Filter Aid and the pad washed with thanol (100 ml). The combined filtrate and washings were evaporated in vacuo and the residue was partitioned between chloroform (100 ml) and 0.5M potassium hydroxide (10 ml).

The layers were separated and the aqueous phase extracted with fresh chloroform (2×100 ml) and the combined organic extracts dried over magnesium sulphate and evaporated in vacuo to give a white solid. This was triturated with ether to give the title compound as a white solid (2.01 g, 60%).

LCMS: $R_t$ 1.93 min; m/z 225 (MH$^+$).

Intermediate 58

2,2-Dicyclohexyl-N-(4-piperidinyl)acetamide

A solution containing dicyclohexylacetic acid (4.75 g), diisopropylethylamine (7.5 ml) and benzotriazol-1-yl-oxy-trispyrrolidinophosphonium hexafluoro phosphate (1 g) in DMF (250 ml) was stirred for 10 min at 20° C. and then 4-amino-1-benzylpiperidine (4.3 ml) was added dropwise over 10 min. The mixture was stirred for 18 h at 20° C. and was then diluted with ethyl acetate (200 ml) and the precipitate collected by filtration, washed with ethyl acetate (60 ml) and water (50 ml) and dried in vacuo to give a white solid (5.91 g). A portion of this (3 g) was suspended in ethanol (300 ml) and treated with 10% palladium on carbon, Degussa type E101 (1.2 g) and ammonium formate (2.68 g). The mixture was stirred for 4 h at 20° C. under a nitrogen atmosphere and was then filtered through a pad of Harborlite J2 Filter Aid and the pad washed with ethanol (50 ml). The combined filtrate and washings were evaporated in vacuo and the residue was partitioned between chloroform (200 ml) and 0.5M sodium hydroxide (150 ml). The layers were separated and the aqueous phase extracted with fresh chloroform (100 ml) and the combined organic extracts dried over magnesium sulphate and evaporated in vacuo to give a white solid. This was triturated with ice cold ether to give the title compound as a white solid (1.8, 78%). LCMS: $R_t$ 2.69 min; m/z 307 (MH$^+$).

Intermediate 59

2-Phenyl-N-(4-piperidinyl)acetamide

To a solution of phenylacetic acid (3.4 g) in acetonitrile (100 ml), under a nitrogen atmosphere, was added 1-(3-dimethylaminopropyl)-3-ethylcarbodiimide hydrochloride (5.28 g) and 1-hydroxybenzotriazole (3.72 g). After stirring for 30 mins at 20° C. 4-amino-1-benzylpiperidine (5.1 ml) was added and stirring was continued for 18 h. The mixture was concentrated in vacuo and the residue was partitioned between 2M hydrochloric acid (100 ml) and ethyl acetate (75 ml). The layers were separated and the aqueous phase was washed with more ethyl acetate (75 ml), basified with solid potassium carbonate and extracted with dichloromethane (2×100 ml). The combined organic extracts were washed with water (2×100 ml) and brine (50 ml), dried over sodium sulphate and evaporated in vacuo to give a white solid (4.8 g). A portion of this (4.7 g) was dissolved in ethanol (150 ml) and treated with 10% palladium on carbon, Degussa type E101 (1.5 g) and ammonium formate (2.88 g). The mixture was stirred for 4 h at 20° C. under a nitrogen atmosphere and was then filtered through a pad of Harborlite J2 Filter Aid and the pad washed with ethanol (150 ml). The combined filtrate and washings were evaporated in vacuo and the residue was partitioned between chloroform (100 ml) and 0.5M sodium hydroxide (50 ml). The layers were separated and the aqueous phase extracted with fresh chloroform (2×100 ml) and the combined organic extracts dried over sodium sulphate and evaporated in vacuo to give the title compound as a white solid (2.4 g, 45%). MS: m/z 219 (MH$^+$), TLC: $R_t$ 0.16 [dichloromethane/methanol/880 ammonia (40:10:1) visualisation with iodine].

EXAMPLES

Example 1

(2S)-2-[((2S)-2-{[2-(2-Benzoylphenoxy)acetyl]amino}-4-methyl pentanoyl)amino]-3-{4-[({4-[(2-phenylacetyl)amino]-1-piperidinyl}carbonyl)oxy]phenyl}propanoic acid

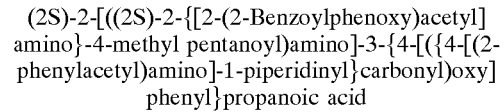

To a solution of 2-hydroxybenzophenone (0.134 g) in anhydrous DMF (0.5 ml) was added anhydrous potassium carbonate (0.093 g) followed by Intermediate 28 (0.152 g) and sodium iodide (0.1 g). After stirring for 18 h at 20° C. the mixture was partitioned between saturated aqueous sodium hydrogen carbonate (10 ml) and ethyl acetate (10 ml). The layers were separated and the aqueous phase was further extracted with ethyl acetate (3×10 ml). The combined organic extracts were washed with water (20 ml) and brine (20 ml), dried over sodium sulphate and evaporated in vacuo. The crude material was purified by flash column chromatography on silica gel eluting with dichloromethane/methanol (10:1) to give a pale yellow solid. To a solution of this in methanol (0.5 ml) was added 1M sodium hydroxide (0.22 ml). After stirring for 1.5 h at 20° C. the mixture was partitioned between 2M hydrochloric add (5 ml) and dichloromethane (10 ml). The layers were separated and the aqueous phase was further extracted with dichloromethane (2×10 ml). The combined organic extracts were washed with water (20 ml) and brine (20 ml), dried over sodium sulphate and evaporated in vacuo to give the title compound as a pale yellow foam (0.123 g, 73%). LCMS: $R_t$ 3.84 min; m/z 775 [M−H]$^-$.

Example 2

(2S)-2-({(2S)-4-Methyl-2-[(2-{[3-(1-piperidinylcarbonyl)-2-naphthyl]oxy}acetyl)amino]pentanoyl}amino)-3-{4-[({4-[(2-phenylacetyl)amino]-1-piperidinyl}carbonyl)oxy]phenyl}propanoic acid

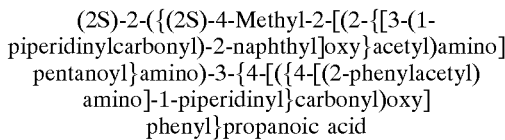

To a solution of triphosgene (0.04 g) in anhydrous dichloromethane (1 ml), under a nitrogen atmosphere, was added a solution of Intermediate 3 (0.2 g) in anhydrous THF (2 ml) followed by diisopropylethylamine (0.07 ml). After stirring for 3 h at 20° C. Intermediate 59 (0.09 g) was added followed by diisopropylethylamine (0.07 ml). Stirring was continued for 18 h then the mixture was partitioned between 2M hydrochloric acid (30 ml) and ethyl acetate (30 ml). The layers were separated and the aqueous phase was further extracted with ethyl acetate (20 ml). The combined organic extracts were washed with saturated aqueous sodium hydrogen carbonate (20 ml), water (20 ml) and brine (20 ml), dried over sodium sulphate and evaporated in vacuo. The crude material was purified by flash column chromatography on silica gel eluting with ethyl acetate switching to ethyl acetate/ethanol (9:1) to give a white foam (0.19 g). To a solution of this (0.15 g) in methanol (2 ml) was added 2M sodium hydroxide (0.18 ml). After stirring for 1 h at 20° C. the mixture was partitioned between 2M hydrochloric acid (40 ml) and ethyl acetate (30 ml). The layers were separated and the aqueous phase was further extracted with ethyl acetate (30 ml). The combined organic extracts were dried over sodium sulphate and evaporated in vacuo. The crude product was purified by flash column chromatography on silica gel eluting with chloroform/methanol/acetic acid (95:5:1) to give the title compound as a white solid (0.12 g, 54% from Intermediate 3). LCMS: $R_t$ 3.73 min; m/z 834 (MH$^+$).

Example 3

(2S)-3-{4-[({4-[(2,2-Dicyclohexylacetyl)amino]-1-piperidinyl}carbonyl)oxy]phenyl}-2-{[(2S)-4-methyl-2-({2-[4-(1-piperidinylcarbonyl)phenoxy]acetyl}amino)pentanoyl]amino}propanoic acid To a solution of Intermediate 48 (0.05 g) in anhydrous DMF (3 ml), under a nitrogen atmosphere, was added 1-(3-dimethylaminopropyl)-3-ethylcarbodiimide hydrochloride (0.04 g) and 1-hydroxybenzotriazole (0.03 g). After stirring for 30 mins at 20° C. Intermediate 10 (0.13 g) was added followed by diisopropylethylamine (0.08 ml), and stirring was continued for 18 h. The mixture was partitioned between 2M hydrochloric acid (40 ml) and ethyl acetate (30 ml). The layers were separated and the aqueous phase was further extracted with ethyl acetate (30 ml). The combined organic extracts were washed with saturated aqueous sodium hydrogen carbonate (30 ml), water (2×30 ml) and brine (20 ml), dried over sodium sulphate and evaporated in vacuo to give a cream coloured solid (0.16 g). To a solution of this (0.15 g) in methanol (2 ml) was added 2M sodium hydroxide (0.18 ml). After stirring for 1 h at 20° C. the mixture was partitioned between 2M hydrochloric acid (40 ml) and ethyl acetate (30 ml). The layers were separated and the aqueous phase was further extracted with ethyl acetate (30 ml). The combined organic extracts were dried over sodium sulphate and evaporated in vacuo. The crude product was purified by flash column chromatography on silica gel eluting with chloroform/methanol/acetic acid (95:5:1) to give the title compound as a white solid (0.12 g, 62% from Intermediate 10). LCMS: $R_t$ 4.26 min; m/z 872 (MH$^+$).

Example 4

(2S)-2-{[(2S)-4-Methyl-2-({2-[4-(1-piperidinylcarbonyl)phenoxy]acetyl}amino)pentanoyl]amino}-3-{4-[(4-morpholinylcarbonyl)oxy]phenyl}propanoic acid To a solution of Intermediate 48 (0.06 g) in acetonitrile (5 ml), under a nitrogen atmosphere, was added 1-(3-dimethylaminopropyl)-3-ethylcarbodiimide hydrochloride (0.06 g) and 1-hydroxybenzotriazole (0.04 g). After stirring for 30 mins at 20° C. Intermediate 15 (0.1 g) was added, and stirring was continued for 18 h. The mixture was partitioned between water (20 ml) and ethyl acetate (25 ml). The layers were separated and the aqueous phase was further extracted with ethyl acetate (20 ml). The combined organic extracts were washed with water (20 ml) and brine (20 ml), dried over sodium sulphate and evaporated in vacuo. The crude material was purified by flash column chromatography on silica gel eluting with dichloromethane/ethanol/880 ammonia (250:8:1) to give a white sticky solid (0.1 g). To this was added trifluoroacetic acid (3 ml) and water (3 drops). After stirring for 4 h at 20° C. the solvent was evaporated in vacuo and the residue was triturated with ether to give the title compound as a white solid (0.06 g, 50%). LCMS: $R_t$ 3.21 min; m/z 653 (MH$^+$).

Example 5

(2S)-3-[4-({[4-(Aminocarbonyl)-1-piperidinyl]carbonyl}oxy)phenyl]-2-{[(2S)-4-methyl-2-({2-[4-(1-piperidinylcarbonyl)phenoxy]acetyl}amino)pentanoyl]amino}propanoic acid This was similarly prepared from Intermediate 48 (0.06 g) and Intermediate 16 (0.12 g). The crude intermediate ester was purified by flash column chromatography on silica gel eluting with dichloromethane/ethanol/880 ammonia (500:8:1 switching via 250:8:1 to 100:8:1). The title compound was obtained as a white solid (0.09 g, 59%). LCMS: $R_t$ 2.84 min; m/z 694 (MH$^+$).

Example 6

(2S)-3-[4-({[4-(Aminocarbonyl)-1-piperidinyl]carbonyl}oxy)phenyl]-2-[((2S)-2-{[2-(2-benzoylphenoxy)acetyl]amino}-4-methylpentanoyl)amino]propanoic acid This was similarly prepared from Intermediate 49 (0.07 g) and Intermediate 16 (0.11 g). The crude intermediate ester was purified by flash column chromatography on silica gel eluting with dichloromethane/ethanol/880 ammonia (500:8:1 switching via 250:8:1 to 100:8:1). The title compound was obtained as a white solid (0.08 g, 42%). LCMS: $R_t$ 3.16 min; m/z 687 (MH$^+$).

Example 7

(2S)-2-{[(2S)-2-({2-[4-(Aminocarbonyl)phenoxy]acetyl}amino)-4-methylpentanoyl]amino}-3-[4-({[4-(aminocarbonyl)-1-piperidinyl]carbonyl}oxy)phenyl]propanoic acid This was similarly prepared from Intermediate 51 (0.06 g) and Intermediate 16 (0.11 g). The crude intermediate ester was purified by flash column chromatography on silica gel eluting with dichloromethane/ethanol/880 ammonia (500:8:1 switching via 250:8:1 and 100:8:1 to 75:8:1). The title compound was obtained as a white solid (0.07 g, 55%). LCMS: $R_t$ 2.65 min; m/z 626 (MH$^+$).

Example 8

(2S)-3-{4-[({4-[(2-Cyclohexylacetyl)amino]-1-piperidinyl}carbonyl)oxy]phenyl}-2-[((2S)-2-{[2-(2-iodophenoxy)acetyl]amino}-4-methylpentanoyl)amino]propanoic acid To a solution of triphosgene (0.058 g) in anhydrous dichloromethane (2 ml), under a nitrogen atmosphere, was added a solution of Intermediate 4 (0.246 g) in anhydrous THF (2 ml) followed by diisopropylethylamine (0.11 ml). After stirring for 4 h at 20° C. Intermediate 57 (0.1 g) was added followed by diisopropylethylamine (0.07 ml). Stirring was continued for 18 h then the mixture was partitioned between 2M hydrochloric acid (50 ml) and dichloromethane (50 ml). The layers were separated and the organic extract was washed with water (20 ml), dried over magnesium sulphate and evaporated in vacuo. The crude material was purified by flash column chromatography on silica gel eluting with ethyl acetate/cyclohexane (1:1) to give a white foam (0.13 g). To a solution of this (0.12 g) in methanol (3 ml) was added 2M sodium hydroxide (1 ml) and water (2 ml). After stirring for 18 h at 20° C. the mixture was partitioned between 2M hydrochloric acid (30 ml) and chloroform (30 ml). The layers were separated and the organic phase was washed with water (20 ml), dried over magnesium sulphate and evaporated in vacuo. The crude product was purified by flash column chromatography on silica gel eluting with chloroform/methanol (4:1) to give the title compound as a white solid (0.064 g, 20%). LCMS: $R_t$ 4.12 min; m/z 805 (MH$^+$).

Example 9

(2S)-3-{4-[({4-[(2,2-Dicyclohexylacetyl)amino]-1-piperidinyl}carbonyl)oxy]phenyl}-2-[((2S)-2-{[2-(2-iodophenoxy)acetyl]amino}-4-methylpentanoyl)amino]propanoic acid This was similarly prepared from Intermediate 4 (0.203 g) and Intermediate 58 (0.14 g). The crude product was purified by flash column chromatography on silica gel eluting with chloroform/methanol (9:1) to give the title compound as a white foam (0.153 g, 52%). LCMS: $R_t$ 4.45 min; m/z 887 (MH$^+$).

Example 10

(2S)-2-({(2S)-2-[(Dibenzo[b,d]furan-4-ylcarbonyl) amino]-4-methyl pentanoyl}amino)-3-{4-[(4-morpholinylcarbonyl)oxy]phenyl}propanoic acid To a solution of Intermediate 6 (0.165 g) in dichloromethane (5 ml), under a nitrogen atmosphere, was added morpholine (0.04 ml) and diisopropylethylamine (0.05 ml). After stirring for 30 mins at 20° C. the solution was diluted with dichloromethane (50 ml) and washed with saturated aqueous potassium carbonate (3×30 ml), 1M hydrochloric acid (2×40 ml) and water (30 ml), dried over magnesium sulphate and evaporated in vacuo to give a white foam (0.143 g). To a solution of this (0.14 g) in methanol (2 ml) was added 1M sodium hydroxide (2 ml) and the mixture was stirred for 30 mins at 20° C., then partitioned between 1M hydrochloric acid (40 ml) and ethyl acetate (50 ml). The organic extract was washed with brine (30 ml), dried over magnesium sulphate and evaporated in vacuo. The crude product was purified by flash column chromatography on silica gel eluting with chloroform/methanol (4:1) to give the title compound as a white solid (0.1 g, 69%). LCMS: $R_t$ 3.85 min; m/z 602 (MH$^+$).

Example 11

(2S)-2-({(2S)-2-[(Dibenzo[b,d]furan-4-ylcarbonyl) amino]-4-methyl pentanoyl}amino)-3-[4-({[4-(2-furoyl)-1-piperazinyl]carbonyl}oxy)phenyl] propanoic acid To a solution of Intermediate 6 (0.13 g) in dichloromethane (5 ml), under a nitrogen atmosphere, was added 1-(2-furoyl)piperazine (0.04 g) and diisopropylethylamine (0.04 ml). After stirring for 3 h at 20° C. the solution was diluted with dichloromethane (20 ml) and washed with saturated aqueous potassium carbonate (3×20 ml), 1M hydrochloric acid (2×20 ml) and water (20 ml), dried over magnesium sulphate and evaporated in vacuo to give a white foam (0.153 g). To a solution of this (0.15 g) in methanol (2 ml) was added 1M sodium hydroxide (2 ml) and the mixture was stirred for 30 mins at 20° C., then partitioned between 1M hydrochloric acid (20 ml) and ethyl acetate (20 ml). The organic extract was washed with brine (20 ml), dried over magnesium sulphate and evaporated in vacuo. The crude product was purified by flash column chromatography on silica gel eluting with chloroform/methanol (4:1) to give the title compound as a white solid (0.126 g, 92%). LCMS: $R_t$ 3.85 min; m/z 695 (MH$^+$).

Example 12

(2S)-3-(4-{[(4-Benzoyl-1-piperazinyl)carbonyl] oxy}phenyl)-2-({(2S)-2-[(dibenzo[b,d]furan-4-ylcarbonyl)amino]-4-methylpentanoyl}amino) propanoic acid To a solution of Intermediate 6 (0.172 g) in dichloromethane (4 ml), under a nitrogen atmosphere, was added Intermediate 56 (0.084 g) and diisopropylethylamine (0.2 ml). After stirring for 3 h at 20° C. the solution was diluted with dichloromethane (50 ml) and washed with saturated aqueous potassium carbonate (3×50 ml), 1M hydrochloric acid (2×50 ml) and water (50 ml), dried over magnesium sulphate and evaporated in vacuo. The crude material was purified by flash column chromatography on silica gel eluting with ethyl acetate/cyclohexane (4:1) to give a white foam. To a solution of this in methanol (2 ml) was added 1M sodium hydroxide (2 ml) and the mixture was stirred for 1 h at 20° C., then partitioned between 1M hydrochloric acid (50 ml) and ethyl acetate (50 ml). The organic extract was washed with brine (50 ml), dried over magnesium sulphate and evaporated in vacuo. The crude product was purified by flash column chromatography on silica gel eluting with chloroform/methanol (4:1) to give the title compound as a white solid (0.041 g, 23%). LCMS: $R_t$ 3.72 min; m/z 705 (MH$^+$).

Example 13

(2S)-2-({(2S)-2-[(Dibenzo[b,d]furan-4-ylcarbonyl) amino]-4-methyl pentanoyl}amino)-3-{4-[({4-[(2-phenylacetyl)amino]-1-piperidinyl}carbonyl)oxy] phenyl}propanoic acid To a solution of Intermediate 45 (0.055 g) in acetonitrile (2 ml), under a nitrogen atmosphere, was added 1-(3-dimethylaminopropyl)-3-ethylcarbodiimide hydrochloride (0.052 g) and 1-hydroxybenzotriazole (0.038 g). After stirring for 30 mins at 20° C. Intermediate 8 (0.15 g) was added followed by diisopropylethylamine (0.047 ml), and stirring was continued for 18 h. The mixture was diluted with chloroform (100 ml) and washed with 1M hydrochloric acid (3×50 ml), saturated aqueous sodium hydrogen carbonate (3×50 ml) and water (50 ml), dried over magnesium sulphate and evaporated in vacuo to give a white foam (0.189 g). To a solution of this (0.176 g) in methanol (4 ml) was added 1M sodium hydroxide (1 ml) and the mixture was stirred for 2 h at 20° C., then partitioned between 1M hydrochloric acid (50 ml) and ethyl acetate (200 ml). The organic extract was washed with brine (30 ml), dried over magnesium sulphate and evaporated in vacuo. The crude product was purified by flash column chromatography on silica gel eluting with a gradient of chloroform/methanol (9:1) to chloroform/methanol (4:1) to give the title compound as a white solid (0.103 g, 79%). LCMS: $R_t$ 4.00 min; m/z 733 (MH$^+$).

Example 14

(2S)-2-[((2S)-2-{[2-(2-Iodophenoxy)acetyl]amino}-4-methyl pentanoyl)amino]-3-{4-[({4-[(2-phenylacetyl)amino]-1-piperidinyl}carbonyl)oxy] phenyl}propanoic acid This was similarly prepared from Intermediate 43 (0.073 g) and Intermediate 8 (0.15 g). The crude product was purified by flash column chromatography on silica gel eluting with chloroform/methanol (6:1) to give the title compound as a white solid (0.103 g, 53%). LCMS: $R_t$ 3.84 min; m/z 799 (MH$^+$).

Example 15

(2S)-3-(4-{[(4-Acetyl-1-piperazinyl)carbonyl] oxy}phenyl)-2-[((2S)-2-{[2-(2-iodophenoxy)acetyl] amino}-4-methylpentanoyl)amino]propanoic acid To a solution of Intermediate 43 (0.07 g) in acetonitrile (5 ml), under a nitrogen atmosphere, was added 1-(3-dimethylaminopropyl)-3-ethylcarbodiimide hydrochloride (0.05 g) and 1-hydroxybenzotriazole (0.04 g). After stirring for 30 mins at 20° C. Intermediate 21 (0.135 g) was added followed by diisopropylethylamine (0.05 ml) and stirring was continued for 18 h. The mixture was partitioned between 1M hydrochloric acid (50 ml) and ethyl acetate (30 ml). The layers were separated and the aqueous phase was further extracted with ethyl acetate (30 ml). The combined organic extracts were washed with saturated aqueous sodium hydrogen carbonate (40 ml) and water (2×50 ml), dried over sodium sulphate and evaporated in vacuo. The residue was co-evaporated with dichloromethane to give a white foam. To this was added trifluoroacetic acid (2 ml) and water (3 drops). After stirring for 4 h at 20° C. the solvent was evaporated in vacuo and the residue was triturated with ether to give the title compound as a white solid (0.143 g, 83%). LCMS: $R_t$ 3.12 min; m/z 709 (MH$^+$).

Example 16

(2S)-3-(4-{[(4-Acetyl-1-piperazinyl)carbonyl]oxy}phenyl)-2-{[(2S)-2-({2-[2-(tert-butyl)phenoxy]acetyl}amino)-4-methylpentanoyl]amino}propanoic acid To a solution of Intermediate 46 (0.052 g) in acetonitrile (5 ml), under a nitrogen atmosphere, was added 1-(3-dimethylaminopropyl)-3-ethylcarbodiimide hydrochloride (0.05 g) and 1-hydroxybenzotriazole (0.04 g). After stirring for 30 mins at 20° C. Intermediate 21 (0.135 g) was added followed by diisopropylethylamine (0.05 ml) and stirring was continued for 18 h. The mixture was partitioned between 1M hydrochloric acid (50 ml) and ethyl acetate (30 ml). The layers were separated and the aqueous phase was further extracted with ethyl acetate (30 ml). The combined organic extracts were washed with saturated aqueous sodium hydrogen carbonate (40 ml) and water (2×50 ml), dried over sodium sulphate and evaporated in vacuo. The residue was co-evaporated with dichloromethane to give a white foam. To this was added trifluoroacetic acid (2 ml) and water (3 drops). After stirring for 4 h at 20° C. the solvent was evaporated in vacuo and the residue was triturated with ether to give the title compound as a white solid (0.115 g, 74%). LCMS: $R_t$ 3.31 min; m/z 639 (MH$^+$).

Example 17

(2S)-3-(4-{[(4-Acetyl-1-piperazinyl)carbonyl]oxy}phenyl)-2-[((2S)-4-methyl-2-{[2-(2-methylphenoxy)acetyl]amino}pentanoyl)amino]propanoic acid To a solution of (2-methylphenoxy)acetic acid (0.042 g) in acetonitrile (5 ml), under a nitrogen atmosphere, was added 1-(3-dimethylaminopropyl)-3-ethylcarbodiimide hydrochloride (0.05 g) and 1-hydroxybenzotriazole (0.04 g). After stirring for 30 mins at 20° C. Intermediate 21 (0.135 g) was added followed by diisopropylethylamine (0.05 ml) and stirring was continued for 18 h. The mixture was partitioned between 1M hydrochloric acid (50 ml) and ethyl acetate (30 ml). The layers were separated and the aqueous phase was further extracted with ethyl acetate (30 ml). The combined organic extracts were washed with saturated aqueous sodium hydrogen carbonate (40 ml) and water (2×50 ml), dried over sodium sulphate and evaporated in vacuo. The residue was co-evaporated with dichloromethane to give a white foam. To this was added trifluoroacetic acid (2 ml) and water (3 drops). After stirring for 4 h at 20° C. the solvent was evaporated in vacuo and the residue triturated with ether to give the title compound as a white solid (0.124 g, 86%). LCMS: $R_t$ 3.10 min; m/z 597 (MH$^+$).

Example 18

(2S)-3-(4-{[(4-Acetyl-1-piperazinyl)carbonyl]oxy}phenyl)-2-({(2S)-2-[(dibenzo[b,d]furan-4-ylcarbonyl)amino]-4-methylpentanoyl}amino)propanoic acid To a solution of Intermediate 45 (0.053 g) in acetonitrile (5 ml), under a nitrogen atmosphere, was added 1-(3-dimethylaminopropyl)-3-ethylcarbodiimide hydrochloride (0.05 g) and 1-hydroxybenzotriazole (0.04 g). After stirring for 30 mins at 20° C. Intermediate 21 (0.135 g) was added followed by diisopropylethylamine (0.05 ml) and stirring was continued for 18 h. The mixture was partitioned between 1M hydrochloric acid (50 ml) and ethyl acetate (30 ml). The layers were separated and the aqueous phase was further extracted with ethyl acetate (30 ml). The combined organic extracts were washed with saturated aqueous sodium hydrogen carbonate (40 ml) and water (2×50 ml), dried over sodium sulphate and evaporated in vacuo. The residue was co-evaporated with dichloromethane to give a white foam. To this was added trifluoroacetic acid (2 ml) and water (3 drops). After stirring for 4 h at 20° C. the solvent was evaporated in vacuo and the residue was triturated with ether to give the title compound as a white solid (0.127 g, 83%). LCMS: $R_t$ 3.33 min; m/z 643 (MH$^+$).

Example 19

(2S)-3-(4-{[(4-Benzoyl-1-piperazinyl)carbonyl]oxy}phenyl)-2-[((2S)-2-{[2-(2-iodophenoxy)acetyl]amino}-4-methylpentanoyl)amino]propanoic acid This was similarly prepared from Intermediate 43 (0.07 g) and Intermediate 22 (0.151 g). The title compound was obtained as a white solid (0.152 g, 81%).

LCMS: $R_t$ 3.58 min; m/z 771 (MH$^+$).

Example 20

(2S)-3-(4-{[(4-Benzoyl-1-piperazinyl)carbonyl]oxy}phenyl)-2-{[(2S)-2-({2-[2-(tert-butyl)phenoxy]acetyl}amino)-4-methylpentanoyl]amino}propanoic acid To a solution of Intermediate 46 (0.052 g) in acetonitrile (5 ml), under a nitrogen atmosphere, was added 1-(3-dimethylaminopropyl)-3-ethylcarbodiimide hydrochloride (0.05 g) and 1-hydroxybenzotriazole (0.04 g). After stirring for 30 mins at 20° C. Intermediate 22 (0.151 g) was added followed by diisopropylethylamine (0.05 ml) and stirring was continued for 18 h. The mixture was partitioned between 1M hydrochloric acid (50 ml) and ethyl acetate (30 ml). The layers were separated and the aqueous phase was further extracted with ethyl acetate (30 ml). The combined organic extracts were washed with saturated aqueous sodium hydrogen carbonate (40 ml) and water (2×50 ml), dried over sodium sulphate and evaporated in vacuo. The residue was co-evaporated with dichloromethane to give a white foam. To this was added trifluoroacetic acid (2 ml) and water (3 drops). After stirring for 4 h at 20° C. the solvent was evaporated in vacuo and the residue was triturated with ether to give the title compound as a white foam (0.17 g, 90%). LCMS: $R_t$ 3.61 min; m/z 701 (MH$^+$).

Example 21

(2S)-3-(4-{[(4-Benzoyl-1-piperazinyl)carbonyl]oxy}phenyl)-2-[((2S)-4-methyl-2-{[2-(2-methylphenoxy)acetyl]amino}pentanoyl)amino]propanoic acid To a solution of (2-methylphenoxy)acetic acid (0.472 g) in acetonitrile (30 ml), under a nitrogen atmosphere, was added 1-(3-dimethylaminopropyl)-3-ethylcarbodiimide hydrochloride (0.56 g) and 1-hydroxybenzotriazole (0.4 g). After stirring for 30 mins at 20° C. a solution of Intermediate 22 (1.5 g) in acetonitrile (25 ml) was added and stirring was continued for 18 h. The mixture was partitioned between 1M hydrochloric acid (50 ml) and ethyl acetate (75 ml). The layers were separated and the organic phase was washed with saturated aqueous sodium hydrogen carbonate (40 ml) and water (50 ml), dried over sodium sulphate and evaporated in vacuo to give a white foam. To a solution of this in chloroform (12 ml) was added trifluoroacetic acid (6 ml). After stirring for 4 h at 20° C. the solvent was evaporated in vacuo and the residue was co-evaporated with chloroform and ether to give the title compound as a white foam (0.17 g, 90%). LCMS: $R_t$ 3.44 min; m/z 659 (MH$^+$).

Example 22

(2S)-3-(4-{[(4-Benzoyl-1-piperazinyl)carbonyl]oxy}phenyl)-2-[((2S)-2-{[2-(2,4-dichlorophenoxy)acetyl]amino}-4-methylpentanoyl)amino]propanoic acid This was similarly prepared from 2,4-dichlorophenoxyacetic acid (0.055 g) and Intermediate 22 (0.151 g). The title compound was obtained by trituration with ether as a white solid (0.129 g, 75%). LCMS: $R_t$ 3.52 min; m/z 713 (MH$^+$).

Example 23

(2S)-2-[((2S)-2-{[2-(2-Iodophenoxy)acetyl]amino}-4-methyl pentanoyl)amino]-3-{4-[(4-morpholinylcarbonyl)oxy]phenyl}propanoic acid To a solution of Intermediate 43 (0.556 g) in acetonitrile (40 ml), under a nitrogen atmosphere, was added 1-(3-dimethylaminopropyl)-3-ethylcarbodiimide hydrochloride (0.383 g) and 1-hydroxybenzotriazole (0.27 g). After stirring for 30 mins at 20° C. Intermediate 23 (1 g) was added followed by diisopropylethylamine (0.35 ml) and stirring was continued for 18 h. The mixture was partitioned between 1M hydrochloric acid (50 ml) and ethyl acetate (75 ml). The layers were separated and the organic phase was washed with saturated aqueous sodium hydrogen carbonate (40 ml) and water (50 ml), dried over sodium sulphate and evaporated in vacuo to give a white foam. To a solution of this in dichloromethane (20 ml) was added trifluoroacetic acid (20 ml) and water (1 ml). After stirring for 4 h at 20° C. the solvent was evaporated in vacuo and the residue was triturated with ether to give the title compound as a white solid (1.15 g, 92%). LCMS: $R_t$ 3.68 min; m/z 668 (MH$^+$).

Example 24

(2S)-2-{[(2S)-2-({2-[2-(Tert-butyl)phenoxy]acetyl}amino)-4-methyl pentanoyl]amino}-3-{4-[(4-morpholinylcarbonyl)oxy]phenyl}propanoic acid To a solution of Intermediate 46 (0.416 g) in acetonitrile (40 ml), under a nitrogen atmosphere, was added 1-(3-dimethylaminopropyl)-3-ethylcarbodiimide hydrochloride (0.383 g) and 1-hydroxybenzotriazole (0.27 g). After stirring for 30 mins at 20° C. Intermediate 23 (1 g) was added followed by diisopropylethylamine (0.35 ml, and stirring was continued for 18 h. The mixture was partitioned between 1M hydrochloric acid (50 ml) and ethyl acetate (75 ml). The layers were separated and the organic phase was washed with saturated aqueous sodium hydrogen carbonate (40 ml) and water (50 ml), dried over sodium sulphate and evaporated in vacuo to give a white foam. To a solution of this in dichloromethane (20 ml) was added trifluoroacetic acid (20 ml) and water (1 ml). After stirring for 4 h at 20° C. the solvent was evaporated in vacuo and the residue was triturated with ether to give the title compound as a white solid (0.63 g, 53%). LCMS: $R_t$ 3.90 min; m/z 598 (MH$^+$).

NMR (DMSO-d$_6$) δH 12.74 (br s, 1H), 8.38 (d, 1H), 7.81 (d, 1H), 7.20–7.25 (m's, 3H), 7.14 (m, 1H), 6.99 (d, 2H), 6.90 (m, 1H), 6.85 (d, 1H), 4.57 (d, 1H), 4.50 (m's, 3H), 3.61 (m, 4H), 3.52 (br m, 2H), 3.30–3.40 (excess 2H, obscured by water), 3.06 (dd, 1H), 2.90 (dd, 1H), 1.57 (m, 1H), 1.38–1.50 (m's, 2H), 1.35 (s, 9H), 0.87 (d, 3H), 0.85 (d, 3H).

Example 24 (Alternative Procedure)

(2S)-2-{[(2S)-2-({2-[2-(Tert-butyl)phenoxy]acetyl}amino)-4-methyl pentanoyl]amino}-3-{4-[(4-morpholinylcarbonyl)oxy]phenyl}propanoic acid To Sasrin resin (125 g) was added a solution of (2S)-3-[4-(allyloxy)phenyl]-2-{[(9H-fluoren-9-ylmethoxy)carbonyl]amino}propanoic acid (300 g) in DMF (970 ml). After 15 mins pyridine (60 ml) was added followed by 2,6-dichlorobenzoyl chloride (106.5 ml) dropwise. The mixture was stirred for 18 h at 20° C. The resin was filtered and washed with DMF (3×800 ml), methanol (3×800 ml) and dichloromethane (3×1 l). The resin was treated with acetic anhydride (800 ml) and pyridine (10 ml) and the mixture was stirred for 3.5 h at 45° C. After cooling to 20° C. the resin was filtered and washed with NMP (3×800 ml), methanol (3×800 ml) and dichloromethane (3×800 ml) then dried in vacuo.

200 g of the resin was treated with 20% piperidine in DMF (1.2 l) and stirred for 3 h at 20° C. The resin was filtered and washed with DMF (3×1 l), methanol (3×1 l) and dichloromethane (3×1 l). To this was added a solution of Fmoc-leucine (233.3 g), 1,3-diisopropylcarbodiimide (84.7 g) and 1-hydroxybenzotriazole (89.3 g) in NMP (1.2 l). The mixture was stirred for 18 h at 20° C. The resin was filtered and washed with NMP (3×1 l), methanol (3×1 l) and dichloromethane (3×1 l).

The resin was treated with 20% piperidine in DMF (1.2 l) and stirred for 3 h at 20° C. The resin was filtered and washed with DMF (3×1 l), methanol (3×1 l) and dichloromethane (3×1 l). To this was added a solution of Intermediate 46 (68.8 g), 1,3-diisopropylcarbodiimide (42.3 g) and 1-hydroxybenzotriazole (44.7 g) in NMP (1.2 l). The mixture was stirred for 18 h at 20° C. The resin was filtered and washed with NMP (3×1 l), methanol (3×1 l) and dichloromethane (3×1 l).

To the resin was added dichloromethane (500 ml), phenylsilane (160 ml) and a slurry of tetrakis(triphenylphosphine)palladium(0) (34 g) in dichloromethane (500 ml). The mixture was stirred for 2 h at 20° C. The resin was filtered and washed with dichloromethane (3×1 l), ether (3×1 l) and dichloromethane (6×1 l).

A slurry of the resin in dichloromethane (800 ml) was treated with diisopropylethylamine (120 ml) followed by 4-nitrophenyl chloroformate (131 g) in 3 portions at 10 minute intervals. The mixture was stirred for 2 h at 20° C. The resin was filtered and washed with dichloromethane (3×1 l), ether (3×1 l) and DMF (3×1 l). A slurry of the resin in DMF (800 ml) was treated with a solution of morpholine (56.5 ml) in DMF (200 ml). The mixture was stirred for 2 h at 20° C. The resin was filtered and washed with DMF (3×1 l), ether (3×1 l) and dichloromethane (3×1 l).

A slurry of the resin in dichloromethane (400 ml) was treated with 10% TFA in dichloromethane (800 ml). After stirring for 30 mins at 20° C. the resin was filtered and washed with dichloromethane (2×500 ml). The combined filtrate and washings were evaporated in vacuo. The residue was triturated with ether (750 ml) and the resulting white solid filtered. To this was added acetonitrile (500 ml) and the mixture was heated to reflux. The hot solution was filtered and the filtrate allowed to cool to 20° C. The mixture was filtered to give the title compound as a white solid (50.9 g).

Example 25

(2S)-2-[((2S)-4-Methyl-2-{[2-(2-methylphenoxy) acetyl]amino}pentanoyl)amino]-3-{4-[(4-morpholinylcarbonyl)oxy]phenyl}propanoic acid To a solution of (2-methylphenoxy)acetic acid (0.332 g) in acetonitrile (40 ml), under a nitrogen atmosphere, was added 1-(3-dimethylaminopropyl)-3-ethylcarbodiimide hydrochloride (0.383 g) and 1-hydroxybenzotriazole (0.27 g). After stirring for 30 mins at 20° C. Intermediate 23 (1 g) was added followed by diisopropylethylamine (0.35 ml) and stirring was continued for 18 h. The mixture was partitioned between 1M hydrochloric acid (50 ml) and ethyl acetate (75 ml). The layers were separated and the organic phase was washed with saturated aqueous sodium hydrogen carbonate (40 ml) and water (50 ml), dried over sodium sulphate and evaporated in vacuo to give a white foam. To a solution of this in dichloromethane (20 ml) was added trifluoroacetic acid (20 ml) and water (1 ml). After stirring for 4 h at 20° C. the solvent was evaporated in vacuo and the residue was triturated with ether to give the title compound as a white solid (0.895 g, 80%). LCMS: $R_t$ 3.31 min; m/z 556 (MH$^+$).

Example 26

(2S)-3-[4-({[4-(Aminocarbonyl)-1-piperidinyl] carbonyl}oxy)phenyl]-2-[((2S)-2-{[2-(2-iodophenoxy)acetyl]amino}-4-methylpentanoyl) amino]propanoic acid This was similarly prepared from Intermediate 43 (0.06 g) and Intermediate 24 (0.1 g). The title compound was obtained as a white solid (0.07 g, 56%).

LCMS: $R_t$ 3.33 min; m/z 709 (MH$^+$).

Example 27

(2S)-3-[4-({[4-(Aminocarbonyl)-1-piperidinyl] carbonyl}oxy)phenyl]-2-[((2S)-4-methyl-2-{[2-(2-methylphenoxy)acetyl]amino}pentanoyl)amino] propanoic acid To a solution of (2-methylphenoxy)acetic acid (0.345 g) in acetonitrile (50 ml), under a nitrogen atmosphere, was added 1-(3-dimethylaminopropyl)-3-ethylcarbodiimide hydrochloride (0.4 g) and 1-hydroxybenzotriazole (0.3 g). After stirring for 30 mins at 20° C. Intermediate 24 (1 g) was added followed by diisopropylethylamine (0.35 ml) and stirring was continued for 18 h. The mixture was concentrated in vacuo and the residue was partitioned between 1M hydrochloric acid (100 ml) and ethyl acetate (300 ml). The layers were separated and the organic phase was washed with 1M hydrochloric acid (2×100 ml), saturated aqueous sodium hydrogen carbonate (3×100 ml) and brine (100 ml), dried over magnesium sulphate and evaporated in vacuo to give a white solid. To a solution of this in chloroform (5 ml) was added trifluoroacetic acid (5 ml) and water (1 ml). After stirring for 3 h at 20° C. the solvent was evaporated in vacuo and the residue was azeotroped with toluene (2×20 ml) then triturated with ether to give the title compound as a white solid (1.06 g, 96%). LCMS: $R_t$ 3.20 min; m/z 597 (MH$^+$). Solubility in water 0.01 mg/ml.

NMR (DMSO-d$_6$) δH 12.75 (br s, 1H), 8.33 (d, 11H), 7.81 (d, 1H), 7.32 (br s, 1H), 7.21 (d, 2H), 7.15 (d, 1H), 7.11 (t, 1H), 6.98 (d, 2H), 6.79–6.89 (m's, 3H), 4.46–4.56 (AB system, 2H), 4.39–4.46 (m's, 2H), 3.95–4.14 (m's, 2H), 2.80–3.10 (m's, 4H), 2.33 (m, 1H), 2.20 (s, 3H), 1.75 (m, 2H), 1.40–1.60 (m's, 5H), 0.82–0.87 (m's, 6H).

Example 27 (Alternative Procedure)

(2S)-3-[4-({[4-(Aminocarbonyl)-1-piperidinyl] carbonyl}oxo)phenyl]-2-[((2S)-4-methyl-2-{[2-(2-methylphenoxy)acetyl]amino}pentanoyl)amino] propanoic acid To Wang resin (50 g) was added a solution of (2S)-3-[4-(allyloxy)phenyl]-2-[(tert-butoxycarbonyl)amino]propanoic acid (115.8 g) and 1-hydroxybenzotriazole (48.6 g) in DMF (475 ml). After 15 minutes 1,3-diisopropylcarbodiimide (56.5 ml) was added and the mixture was stirred for 24 h at 45° C. The resin was filtered and washed with DMF (3×360 ml), methanol (3×360 ml) and dichloromethane (3×700 ml). To a slurry of the resin in dichloromethane (644 ml) was added pyridine (14.7 ml). Acetic anhydride (26.9 ml) was added and the mixture was stirred for 12 h at 20° C. The resin was filtered and washed with dichloromethane (3×550 ml), methanol (3×370 ml) and dichloromethane (3×550 ml).

A slurry of 20 g of the resin in dichloromethane (100 ml) was cooled to 2–5° C. and treated with a solution of phenol (20 g) in dichloromethane (80 ml). Chlorotrimethylsilane (20 ml) was added dropwise and the mixture was stirred for 6 h at 2–5° C. The resin was filtered and washed with dichloromethane (3×200 ml), methanol (3×200 ml), 10% water in DMF (2×200 ml), 10% diisopropylethylamine in DMF (3×200 ml), DMF (200 ml), methanol (3×200 ml) and dichloromethane (3×200 ml).

A slurry of the resin in DMF (55 ml) was treated with a solution of Fmoc-leucine (32.7 g) and 1-hydroxybenzotriazole (12.5 g) in DMF (85 ml). After 5 minutes 1,3-diisopropylcarbodiimide (19.3 ml) was added and the mixture was stirred for 15 h at 20° C. The resin was filtered and washed with DMF (3×150 ml), methanol (3×150 ml) and dichloromethane (3×150 ml).

The resin was treated with 20% piperidine in DMF (180 ml) and stirred for 1 h at 20° C. The resin was filtered and washed with DMF (3×150 ml), dichloromethane (3×150 ml), DMF (3×150 ml) and dichloromethane (3×150 ml). To a slurry of this in DMF (50 ml) was added a solution of (2-methylphenoxy)acetic acid (17.9 g) and 1-hydroxybenzotriazole (14.6 g) in DMF (100 ml). After 5 minutes 1,3-diisopropylcarbodiimide (16.9 ml) was added and the mixture was stirred for 65 h at 20° C. The resin was filtered and washed with DMF (2×150 ml), methanol (3×150 ml) and dichloromethane (3×150 ml).

A slurry of the resin in dichloromethane (60 ml) was treated with a solution of tetrakis(triphenylphosphine) palladium(0) (5.21 g) in dichloromethane (140 ml) followed by morpholine (13 ml). The mixture was stirred for 2 h at 20° C. then the resin was filtered and washed with dichloromethane (7×200 ml).

A slurry of the resin in dichloromethane (160 ml) was treated with diisopropylethylamine (12.4 ml) followed by 4-nitrophenyl chloroformate (24.8 g) in 3 portions at 5 minute intervals. The mixture was stirred for 1 h at 20° C. The resin was filtered and washed with dichloromethane (3×200 ml). The resin was treated with a solution of isonipecotamide (15.8 g) in DMF (180 ml) and the mixture was stirred for 1.5 h at 20° C. The resin was filtered and washed with DMF (4×200 ml) and dichloromethane (2×200 ml).

The resin was treated with 50% TFA in dichloromethane (200 ml). After stirring for 1 h at 20° C. the resin was filtered and washed with dichloromethane (5×200 ml). The combined filtrate and washings were evaporated in vacuo. The residue was azeotroped with toluene (2×100 ml) then triturated with ether (50 ml) and the resulting white solid filtered. To this was added acetonitrile (150 ml) and the mixture was heated to reflux. The resulting suspension was allowed to cool to 20° C. and stirred for 18 h. The mixture was filtered to give the title compound as a white solid (4.9 g).

Example 27A (2S)-3-[4-({[4-(Aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid potassium salt A suspension of Example 27 (10 g) in methanol (150 ml) was warmed to reflux to obtain a clear solution. To this was added a solution of potassium carbonate (1.16 g) in water (7.5 ml). After heating under reflux for two minutes the solvents were evaporated in vacuo to give a crisp foam. To this was added acetonitrile (100 ml) and the mixture was warmed to reflux, during which time the foam collapsed and started to crystallise. After ten minutes the mixture was allowed to cool to 20° C. then filtered under reduced pressure, washed with acetonitrile (25 ml) and ether (50 ml) to give the title compound as a white solid (10.65 g, 100%). The product is believed to be isolated in the form of its monohydrate. Solubility in water: >250 mg/ml.

NMR (DMSO-$d_6$) δH 8.27 (d, 1H), 7.42 (d, 1H), 7.37 (d, 1H), 7.04–7.16 (m's, 4H), 6.78–8.88 (m's, 5H), 4.44–4.59 (AB system, 2H), 4.21 (m, 1H), 3.95–4.12 (br m's, 2H), 3.87 (m, 1H), 2.80–3.10 (m's, 4H), 2.34 (m, 1H), 2.20 (s, 3H), 1.75 (m, 2H), 1.41–1.60 (m's, 5H), 0.86 (d, 3H), 0.80 (d, 3H).

Example 28

(2S)-3-[4-({[4-(Aminocarbonyl)-1-piperidinyl]carbonyl}oxy)phenyl]-2-({(2S)-2-[(dibenzo[b,d]furan-4-ylcarbonyl)amino]-4-methylpentanoyl}amino)propanoic acid To a solution of Intermediate 45 (0.438 g) in acetonitrile (50 ml), under a nitrogen atmosphere, was added 1-(3-dimethylaminopropyl)-3-ethylcarbodiimide hydrochloride (0.4 g) and 1-hydroxybenzotriazole (0.29 g). After stirring for 30 mins at 20° C. Intermediate 24 (1 g) was added followed by diisopropylethylamine (0.35 ml) and stirring was continued for 18 h. The mixture was concentrated in vacuo and the residue was partitioned between 1M hydrochloric acid (100 ml) and ethyl acetate (300 ml). The layers were separated and the organic phase was washed with 1M hydrochloric acid (2×100 ml), saturated aqueous sodium hydrogen carbonate (3×100 ml) and brine (100 ml), dried over magnesium sulphate and evaporated in vacuo to give a white solid. To a solution of this in chloroform (5 ml) was added trifluoroacetic acid (5 ml) and water (1 ml). After stirring for 3 h at 20° C. the solvent was evaporated in vacuo and the residue was azeotroped with toluene (2×20 ml) then triturated with ether to give the title compound as a white solid (0.95 g, 80%). LCMS: $R_t$ 3.48 min; m/z 643 (MH$^+$).

Example 29

(2S)-2-{[(2S)-2-({2-[2-(Tert-butyl)phenoxy]acetyl}amino)-4-methyl pentanoyl]amino}-3-[4-({[4-(1-piperidinylcarbonyl)-1-piperidinyl]carbonyl}oxy)phenyl]propanoic acid To a solution of Intermediate 46 (0.1 g) in acetonitrile (5 ml), under a nitrogen atmosphere, was added 1-(3-dimethylaminopropyl)-3-ethylcarbodiimide hydrochloride (0.09 g) and 1-hydroxybenzotriazole (0.063 g). After stirring for 30 mins at 20° C. Intermediate 20 (0.18 g) was added and stirring was continued for 18 h. The mixture was partitioned between water (20 ml) and ethyl acetate (20 ml). The layers were separated and the organic phase was washed with saturated aqueous sodium hydrogen carbonate (2×30 ml), water (30 ml) and brine (30 ml), dried over sodium sulphate and evaporated in vacuo. The crude material was purified by flash column chromatography on silica gel eluting with dichloromethane/methanol (20:1) to give a clear oil. To a solution of this in dichloromethane (8 ml) was added trifluoroacetic acid (2 ml). After stirring for 2 h at 20° C. the solvent was evaporated in vacuo and the crude product purified by flash column chromatography on silica gel eluting with dichloromethane/methanol/acetic acid/water (240:15:3:2) to give the title compound as a white foam (0.08 g, 36%). LCMS: $R_t$ 4.07 min; m/z 707 (MH$^+$).

Example 30

(2S)-2-[((2S)-4-Methyl-2-{[2-(2-methylphenoxy)acetyl]amino}pentanoyl)amino]-3-[4-({[4-(1-piperidinylcarbonyl)-1-piperidinyl]carbonyl}oxy)phenyl]propanoic acid This was similarly prepared from (2-methylphenoxy)acetic acid (0.09 g) and Intermediate 20 (0.3 g). The crude product was purified by flash column chromatography on silica gel eluting with dichloromethane/methanol/acetic acid/water (240:15:3:2) to give the title compound as a white foam (0.116 g, 34%). LCMS: $R_t$ 3.56 min; m/z 665 (MH$^+$).

Example 31

(2S)-2-({(2S)-2-[(Dibenzo[b,d]furan-4-ylcarbonyl)amino]-4-methyl pentanoyl}amino)-3-[4-({[4-(1-piperidinylcarbonyl)-1-piperidinyl]carbonyl}oxy)phenyl]propanoic acid This was similarly prepared from Intermediate 45 (0.1 g) and Intermediate 20 (0.176 g). The crude product was purified by flash column chromatography on silica gel eluting with dichloromethane/methanol/acetic acid/water (180:15:3:2) to give the title compound as a white foam (0.075 g, 35%). LCMS: $R_t$ 4.09 min; m/z 711 (MH$^+$).

Example 32

(2S)-2-{[(2S)-2-({2-[(1-Bromo-2-naphthyl)oxy]acetyl}amino)-4-methylpentanoyl]amino}-3-[4-({[4-(1-piperidinylcarbonyl)-1-piperidinyl]carbonyl}oxy)phenyl]propanoic acid This was similarly prepared from Intermediate 50 (0.124 g) and Intermediate 20 (0.168 g). The crude product was purified by flash column chromatography on silica gel eluting with dichloromethane/methanol/acetic acid/water (200:15:3:2) to give the title compound as a white foam (0.055 g, 24%). LCMS: $R_t$ 4.19 min; m/z 779 (MH$^+$).

Example 33

(2S)-3-[4-({[4-(Aminocarbonyl)-1-piperidinyl]carbonyl}oxy)phenyl]-2-{[(2S)-2-({2-[2-(tert-butyl)phenoxy]acetyl}amino)-4-methylpentanoyl]amino}propanoic acid To a solution of Intermediate 26 (0.47 g) in dichloromethane (8 ml), under a nitrogen atmosphere, was added isonipecotamide (0.106 g) and diisopropylethylamine (0.2 ml). The mixture was stirred for 18 h at 20° C. then diluted with chloroform (100 ml), washed with saturated aqueous potassium carbonate (3×50 ml), 1M hydrochloric acid (3×50 ml) and water (50 ml), dried over magnesium sulphate and evaporated in vacuo to give a white foam. To a solution of this in chloroform (3 ml) was added trifluoroacetic acid (3 ml). After stirring for 4 h at 20° C. the solvent was evaporated in vacuo and the residue was triturated with ether to give the title compound as a white solid (0.223 g, 52%).

LCMS: $R_t$ 3.35 min; m/z 639 (MH$^+$).

Example 34

(2S)-2-{[(2S)-2-({2-[2-(Tert-butyl)phenoxy]acetyl}amino)-4-methyl pentanoyl]amino}-3-(4-{[(4-{[(4-fluorobenzyl)amino]carbonyl}-1-piperidinyl)carbonyl]oxy}phenyl)propanoic acid This was similarly prepared from Intermediate 26 (0.312 g) and Intermediate 54 (0.181 g). The title compound was obtained as a white solid (0.187 g, 57%).

LCMS: $R_t$ 3.71 min; m/z 747 (MH$^+$).

Example 35

(2S)-2-[((2S)-2-{[2-(2,4-Dichlorophenoxy)acetyl]amino}-4-methyl pentanoyl)amino]-3-{4-[(4-morpholinylcarbonyl)oxy]phenyl}propanoic acid To a suspension of anhydrous potassium carbonate (0.057 g) and sodium iodide (0.051 g) in anhydrous DMF (1 ml) was added 2,4-dichlorophenol (0.166 g) followed by Intermediate 27 (0.2 g). The mixture was stirred for 18 h at 20° C. then partitioned between saturated aqueous sodium hydrogen carbonate (10 ml) and ethyl acetate (10 ml). The layers were separated and the organic phase was further washed with saturated aqueous sodium hydrogen carbonate (10 ml) and brine (10 ml), dried over magnesium sulphate and evaporated in vacuo. The crude material was purified by flash column chromatography on silica gel eluting with ethyl acetate/cyclohexane (1:1) to give a white foam. To a solution of this in dichloromethane (2 ml) was added trifluoroacetic acid (2 ml). After stirring for 2 h at 20° C. the solvent was evaporated in vacuo and the residue was triturated with ether to give the title compound as a white solid (0.146 g, 70%). LCMS: $R_t$ 3.70 min; m/z 610 (MH$^+$).

Example 36

(2S)-2-[((2S)-2-{[2-(2-Benzoylphenoxy)acetyl]amino}-4-methyl pentanoyl)amino]-3-{4-[(4-morpholinylcarbonyl)oxy]phenyl}propanoic acid This was similarly prepared from 2-hydroxybenzophenone (0.2 g) and Intermediate 27 (0.2 g). The title compound was obtained as a pale yellow foam (0.057 g, 26%). LCMS: $R_t$ 3.60 min; m/z 646 (MH$^+$).

Example 37

(2S)-2-[((2S)-4-Methyl-2-{[2-(2-propylphenoxy)acetyl]amino}pentanoyl)amino]-3-{4-[(4-morpholinylcarbonyl)oxy]phenyl}propanoic acid This was similarly prepared from 2-propylphenol (0.14 ml) and Intermediate 27 (0.2 g). The title compound was obtained as a white solid (0.141 g, 70%).

LCMS: $R_t$ 3.71 min; m/z 584 (MH$^+$).

Example 38

(2S)-2-{[(2S)-2-({2-[(1-Bromo-2-naphthyl)oxy]acetyl}amino)-4-methylpentanoyl]amino}-3-{4-[(4-morpholinylcarbonyl)oxy]phenyl}propanoic acid This was similarly prepared from 1-bromo-2-naphthol (0.23 g) and Intermediate 27 (0.2 g). The title compound was obtained as a white solid (0.11 g, 48%).

LCMS: $R_t$ 3.91 min; m/z 670 (MH$^+$).

Example 39

(2S)-2-[((2S)-2-{[2-(2-Cyclohexylphenoxy)acetyl]amino}-4-methyl pentanoyl)amino]-3-{4-[(4-morpholinylcarbonyl)oxy]phenyl}propanoic acid To a suspension of anhydrous potassium carbonate (0.1 g) and sodium iodide (0.06 g) in anhydrous DMF (1 ml) was added 2-cyclohexylphenol (0.12 g) followed by Intermediate 27 (0.2 g). The mixture was stirred for 18 h at 20° C. then partitioned between saturated aqueous sodium hydrogen carbonate (10 ml) and ethyl acetate (10 ml). The layers were separated and the organic phase was further washed with saturated aqueous sodium hydrogen carbonate (10 ml) and brine (10 ml), dried over magnesium sulphate and evaporated in vacuo. The crude material was purified by flash column chromatography on silica gel eluting with ethyl acetate/cyclohexane (1:1) to give a white foam. To a solution of this in dichloromethane (3 ml) was added trifluoroacetic acid (3 ml). After stirring for 2 h at 20° C. the solvent was evaporated in vacuo and the residue was azeotroped with toluene then triturated with ether to give the title compound as a white solid (0.118 g, 55%). LCMS: $R_t$ 4.16 min; m/z 624 (MH$^+$).

Example 40

(2S)-2-[((2S)-2-{[(Benzyloxy)carbonyl]amino}-4-methylpentanoyl)amino]-3-{4-[(4-morpholinylcarbonyl)oxy]phenyl}propanoic acid To a solution of Intermediate 13 (0.19 g) in chloroform (2 ml) was added trifluoroacetic acid (2 ml). After stirring for 4 h at 20° C. the solvent was evaporated in vacuo and the residue was triturated with ether to give the title compound as a white solid (0.156 g, 90%). LCMS: $R_t$ 3.22 min; m/z 542 (MH$^+$).

Example 41

(2S)-3-[4-({[4-(2-Furoyl)-1-piperazinyl]carbonyl}oxy)phenyl]-2-[((2S)-2-{[2-(2-iodophenoxy)acetyl]amino}-4-methylpentanoyl)amino]propanoic acid Intermediate 38 (0.26 mmol) was treated with DMF (4 ml). 2-Iodophenol (0.57 g), potassium carbonate (0.36 g) and sodium iodide (0.39 g) were added and the mixture was shaken for 16 h at 20° C. The resin was filtered and washed with water (2×5 ml), DMF (5×5 ml) and dichloromethane (5×5 ml) then treated with 1:1 trifluoroacetic acid/dichloromethane (4 ml). After 30 mins the resin was filtered and the filtrate was evaporated in vacuo. The residue was azeotroped with toluene (5 ml) then triturated with ether. The crude product was crystallised from acetonitrile to give the title compound as a white solid (0.043 g).

LCMS: $R_t$ 3.50 min; m/z 761 (MH$^+$).

Example 42

(2S)-2-{[(2S)-2-({2-[2-(Tert-butyl)phenoxy]acetyl}amino)-4-methyl pentanoyl]amino}-3-[4-({[4-(2-furoyl)-1-piperazinyl]carbonyl}oxy)phenyl]propanoic acid Intermediate 38 (0.26 mmol) was treated with DMF (4 ml). 2-tert-butyl phenol (0.4 ml), potassium carbonate (0.36 g) and sodium iodide (0.39 g) were added and the mixture was shaken for 16 h at 20° C. The resin was filtered and washed with water (2×5 ml), DMF (5×5 ml) and dichloromethane (5×5 ml) then treated with 1:1 trifluoroacetic acid/dichloromethane (4 ml). After 30 mins the resin was filtered and the filtrate was evaporated in vacuo. The residue was azeotroped with toluene (5 ml) then triturated with ether. The crude product was purified by flash column chromatography on silica gel eluting with chloroform/methanol/acetic acid (95:5:1) to give the title compound as a white solid (0.04 g). LCMS: $R_t$ 3.63 min; m/z 691 (MH$^+$).

Example 43

(2S)-2-[((2S)-2-{[2-(2-Cyohexylphenoxy)acetyl]amino}-4-methyl pentanoyl)amino]-3-[4-({[4-(2-furoyl)-1-piperazinyl]carbonyl}oxy)phenyl]propanoic acid This was similarly prepared from Intermediate 38 (0.26 mmol) and 2-cyclohexyl phenol (0.46 g). The crude product was purified using a solid phase extraction cartridge containing reverse phase silica eluting with a chloroform/methanol gradient (increasing from 98:2 to 80:20) to give the title compound as a cream solid (0.037 g). LCMS: $R_t$ 3.83 min; m/z 717 (MH$^+$).

Example 44

(2S)-2-{[(2S)-2-({2-[(1-Bromo-2-naphthyl)oxy]acetyl}amino)-4-methylpentanoyl]amino}-3-[4-({[4-(2-furoyl)-1-piperazinyl]carbonyl}oxy)phenyl]propanoic acid This was similarly prepared from Intermediate 38 (0.26 mmol) and 1-bromo-2-naphthol (0.58 g). The crude product was crystallised from acetonitrile to give the title compound as a cream coloured solid (0.064 g). LCMS: $R_t$ 3.69 min; m/z 763 (MH$^+$).

Example 45

(2S)-3-(4-{[(4-{[2-(4-Chlorophenyl)acetyl]amino}-1-piperidinyl)carbonyl]oxy}phenyl)-2-[((2S)-2-{[2-(2-cyclohexylphenoxy)acetyl]amino}-4-methylpentanoyl)amino]propanoic acid This was similarly prepared from Intermediate 39 (0.29 mmol) and 2-cyclohexyl phenol (0.48 g). The crude product was purified by flash column chromatography on silica gel eluting with chloroform/methanol/acetic acid (95:5:0.5) to give the title compound as a white solid (0.073 g). LCMS: $R_t$ 4.13 min; m/z 789 (MH$^+$).

Example 46

(2S)-2-[((2S)-2-{[2-(2-Benzoylphenoxy)acetyl]amino}-4-methyl pentanoyl)amino]-3-(4-{[(4-{[2-(4-chlorophenyl)acetyl]amino}-1-piperidinyl)carbonyl]oxy}phenyl)propanoic acid This was similarly prepared from Intermediate 39 (0.29 mmol) and 2-hydroxybenzophenone (0.55 g). The crude product was purified by flash column chromatography on silica gel eluting with chloroform/methanol/acetic acid (95:5:0.5) to give the title compound as a white solid (0.065 g). LCMS: $R_t$ 3.75 min; m/z 811 (MH$^+$).

Example 47

(2S)-3-(4-{[(4-{[2-(4-Chlorophenyl)acetyl]amino}-1-piperidinyl)carbonyl]oxy}phenyl)-2-[((2S)-2-{[2-(2-iodophenoxy)acetyl]amino}-4-methyl pentanoyl)amino]propanoic acid Intermediate 37 (0.27 mmol) was treated with 20% piperidine in DMF (5 ml) and shaken for 1 h at 20° C. The resin was filtered and washed with DMF (5×5 ml). A solution of Intermediate 43 (0.154 g) in DMF (3 ml) was added followed by a solution of benzotriazol-1-yl-oxy-trispyrrolidinophosphonium hexafluoro phosphate (0.285 g) in DMF (2 ml) and diisopropylethylamine (0.26 ml). The mixture was shaken for 18 h at 20° C. The resin was filtered and washed with DMF (5×5 ml) and dichloromethane (5×5 ml), then treated with 1:1 trifluoroacetic acid/dichloromethane (5 ml). After 30 mins the resin was filtered and the filtrate was evaporated in vacuo. The crude product was purified by flash column chromatography on silica gel eluting with chloroform/methanol/acetic acid (95:5:0.5) to give the title compound as a white solid (0.083 g). LCMS: $R_t$ 3.76 min; m/z 833 (MH$^+$).

Example 48

(2S)-2-{[(2S)-2-({2-[2-(Tert-butyl)phenoxy]acetyl}amino)-4-methyl pentanoyl]amino}-3-(4-{[(4-{[2-(4-chlorophenyl)acetyl]amino}-1-piperidinyl)carbonyl]oxy}phenyl)propanoic acid This was similarly prepared from Intermediate 37 (0.27 mmol) and Intermediate 46 (0.115 g). The crude product was purified by flash column chromatography on silica gel eluting with chloroform/methanol/acetic acid (95:5:0.5) to give the title compound as a white solid (0.107 g). LCMS: $R_t$ 3.93 min; m/z 763 (MH$^+$).

Example 49

(2S)-3-(4-{[(4-{[2-(4-Chlorophenyl)acetyl]amino}-1-piperidinyl)carbonyl]oxy}phenyl)-2-({(2S)-2-[(dibenzo[b,d]furan-4-ylcarbonyl)amino]-4-methylpentanoyl}amino)propanoic acid This was similarly prepared from Intermediate 37 (0.27 mmol) and Intermediate 45 (0.117 g). The crude product was purified by flash column chromatography on silica gel eluting with chloroform/methanol/acetic acid (95:5:0.5) to give the title compound as a white solid (0.056 g). LCMS: $R_t$ 3.80 min; m/z 765 [M–H]$^-$.

Example 50

(2S)-3-(4-{[(4-{[2-(4-Chlorophenyl)acetyl]amino}-1-piperidinyl)carbonyl]oxy}phenyl)-2-({(2S)-4-methyl-2-[(2-{[3-(1-piperidinylcarbonyl)-2-naphthyl]oxy}acetyl)amino]pentanoyl}amino)propanoic acid This was similarly prepared from Intermediate 37 (0.27 mmol) and Intermediate 44 (0.173 g). The crude product was purified by flash column chromatography on silica gel eluting with chloroform/methanol/acetic acid (95:5:0.5) to give the title compound as a white solid (0.062 g). LCMS: $R_t$ 3.71 min; m/z 868 (MH$^+$).

Example 51

(2S)-2-{[(2S)-2-({2-[2-(Tert-butyl)phenoxy]acetyl}amino)-4-methyl pentanoyl]amino}-3-{4-[({4-[(2-phenylacetyl)amino]-1-piperidinyl}carbonyl)oxy]phenyl}propanoic acid Intermediate 33 (0.23 mmol) was treated with 1:1 dichloromethane/THF (3 ml). Intermediate 59 (0.105 g) was added followed by diisopropylethylamine (0.16 ml). After shaking for 18 h at 20° C. the resin was filtered, washed with dichloromethane (4×5 ml) and ether (3×5 ml) and then dried in vacuo. LCMS showed that some of the 4-nitrophenyl carbonate had been hydrolysed to the phenol so the resin was treated with 1:1 dichloromethane/THF (3 ml), diisopropylethylamine (0.2 ml) and 4-nitrophenyl chloroformate (0.23 g). After shaking for 18 h at 20° C. the resin was filtered and washed with dichloromethane (4×5 ml) then treated with 1:1 dichloromethane/THF (3 ml), Intermediate 59 (0.07 g) and diisopropylethylamine (0.12 ml). After shaking for 18 h at 20° C. the resin was filtered and washed with dichloromethane (4×5 ml) then treated with 1:1 trifluoroacetic acid/dichloromethane (3 ml). After 30 mins the resin was filtered and the filtrate was evaporated in vacuo. The residue was co-evaporated with dichloromethane followed by ether to give the title compound as an off-white solid (0.083 g). LCMS: $R_t$ 3.99 min; m/z 729 (MH$^+$).

Example 52

(2S)-2-{[(2S)-2-({2-[2-(Tert-butyl)phenoxy]acetyl}amino)-4-methyl pentanoyl]amino}-3-{4-[({4-[(2-cyclohexylacetyl)amino]-1-piperidinyl}carbonyl)oxy]phenyl}propanoic acid This was similarly prepared from Intermediate 33 (0.23 mmol) and Intermediate 57 (0.106 g). The title compound was obtained as an off-white solid (0.073 g).

LCMS: $R_t$ 4.27 min; m/z 735 (MH$^+$).

Example 53

(2S)-2-{[(2S)-2-({2-[2-(Tert-butyl)phenoxy]acetyl}amino)-4-methyl pentanoyl]amino}-3-{4-[({4-[(2,2-dicyclohexylacetyl)amino]-1-piperidinyl}carbonyl)oxy]phenyl}propanoic acid This was similarly prepared from Intermediate 33 (0.25 mmol) and Intermediate 58 (0.144 g). The title compound was obtained as an off-white solid (0.105 g).

LCMS: $R_t$ 4.63 min; m/z 817 (MH$^+$).

Example 54

(2S)-2-[((2S)-4-Methyl-2-{[2-(2-methylphenoxy)acetyl]amino}pentanoyl)amino]-3-{4-[({4-[(2-phenylacetyl)amino]-1-piperidinyl}carbonyl)oxy]phenyl}propanoic acid This was similarly prepared from Intermediate 34 (0.3 mmol) and Intermediate 59 (0.196 g). The crude product was purified by flash column chromatography on silica gel eluting with dichloromethane/methanol/acetic acid/water (240:15:3:2) to give the title compound as a pale yellow foam (0.091 g). LCMS: $R_t$ 3.49 min; m/z 687 (MH$^+$).

Example 55

(2S)-2-[((2S)-2-{[2-(2-Cyclohexylphenoxy)acetyl]amino}-4-methyl pentanoyl)amino]-3-{4-[({4-[(2-phenylacetyl)amino]-1-piperidinyl}carbonyl)oxy]phenyl}propanoic acid Intermediate 42 (0.27 mmol) was treated with a solution of Intermediate 59 (0.178 g) in 1:1 dichloromethane/THF (2 ml) followed by diisopropylethylamine (0.95 ml). After shaking for 2 h at 20° C. the resin was filtered and washed with dichloromethane (5×5 ml) then treated with 1:1 trifluoroacetic acid/dichloromethane (3 ml). After 30 mins the resin was filtered and the filtrate was evaporated in vacuo.

The residue was triturated with ether to give the title compound as an off-white solid (0.074 g). LCMS: $R_t$ 4.04 min; m/z 755 (MH$^+$).

Example 56

(2S)-3-{4-[({4-[(2-Cyclohexylacetyl)amino]-1-piperidinyl}carbonyl)oxy]phenyl}-2-[((2S)-2-{[2-(2-cyclohexylphenoxy)acetyl]amino}-4-methyl pentanoyl)amino]propanoic acid This was similarly prepared from Intermediate 42 (0.27 mmol) and Intermediate 57 (0.18 g). The title compound was obtained as an off-white solid (0.102 g).

LCMS: $R_t$ 4.22 min; m/z 761 (MH$^+$).

Biological Data

The compounds of the Examples were tested in assay (1), the Jurkat adhesion assay, and the results obtained were as follows:

| Example | pIC$_{50}$ | SEM* | n* |
|---|---|---|---|
| 1 | 7.88 | 0.18 | 6 |
| 2 | 8.03 | 0.24 | 4 |
| 3 | 7.38 | 0.12 | 4 |
| 4 | 7.78 | 0.08 | 4 |
| 5 | 8.11 | 0.03 | 4 |
| 6 | 8.25 | 0.06 | 4 |
| 7 | 8.58 | 0.03 | 4 |
| 8 | 7.37 | 0.15 | 4 |
| 9 | 7.58 | 0.10 | 5 |
| 10 | 8.08 | 0.05 | 9 |
| 11 | 8.08 | 0.12 | 10 |
| 12 | 7.96 | 0.06 | 8 |
| 13 | 7.59 | 0.11 | 4 |
| 14 | 7.78 | 0.07 | 4 |
| 15 | 8.57 | 0.04 | 8 |
| 16 | 8.49 | 0.10 | 8 |
| 17 | 8.59 | 0.09 | 8 |
| 18 | 8.43 | 0.38 | 5 |
| 19 | 8.12 | 0.06 | 5 |
| 20 | 7.83 | 0.03 | 6 |
| 21 | 8.41 | 0.07 | 9 |
| 22 | 7.65 | 0.17 | 4 |
| 23 | 8.35 | 0.02 | 10 |
| 24 | 8.22 | 0.08 | 10 |
| 25 | 8.50 | 0.08 | 10 |
| 26 | 8.53 | 0.03 | 4 |
| 27 | 8.55 | 0.10 | 7 |
| 28 | 8.46 | 0.05 | 10 |
| 29 | 7.79 | 0.08 | 6 |
| 30 | 8.24 | 0.03 | 4 |
| 31 | 7.59 | 0.04 | 4 |
| 32 | 7.62 | 0.13 | 6 |
| 33 | 8.46 | 0.03 | 9 |
| 34 | 7.57 | 0.14 | 4 |
| 35 | 8.18 | 0.06 | 6 |
| 36 | 7.91 | 0.07 | 6 |
| 37 | 8.24 | 0.07 | 6 |
| 38 | 7.81 | 0.15 | 4 |
| 39 | 7.65 | 0.12 | 4 |
| 40 | 8.04 | 0.15 | 4 |
| 41 | 8.03 | 0.07 | 4 |
| 42 | 7.96 | 0.07 | 6 |
| 43 | 7.65 | 0.07 | 6 |
| 44 | 7.62 | 0.05 | 5 |
| 45 | 7.24 | 0.11 | 6 |
| 46 | 7.36 | 0.04 | 4 |
| 47 | 7.48 | 0.07 | 4 |
| 48 | 7.38 | 0.04 | 4 |
| 49 | 7.35 | 0.06 | 4 |
| 50 | 7.60 | 0.10 | 4 |
| 51 | 7.86 | 0.05 | 8 |
| 52 | 7.48 | 0.21 | 4 |
| 53 | 6.81 | 0.10 | 5 |
| 54 | 8.25 | 0.03 | 5 |

-continued

| Example | pIC$_{50}$ | SEM* | n* |
|---------|-----------|------|-----|
| 55 | 7.21 | 0.13 | 4 |
| 56 | 7.06 | 0.19 | 6 |

*SEM standard error of the mean of n experiments

The compounds of Examples 16, 17, 20, 21, 23, 24, 27 and 28 were tested in assay (2) the CD3/VCAM-1 Co-stimulation of T-cell proliferation assay, and the results were obtained as follows:

| Example | pIC$_{50}$ |
|---------|-----------|
| 16 | 7.4 |
| 17 | 7.5 |
| 20 | 6.9 |
| 21 | 6.9 |
| 23 | 6.9 |
| 24 | 7.1 |
| 27 | 7.5 |
| 28 | 6.8 |

The compounds of Examples 16, 17, 20, 21, 23, 24, 27 and 28 were also tested in assay (3) the inhibition of lung eosinophil infiltration and hyper-reactivity in the guinea pig (intratracheal dose given 0.5 hours before and 6 hours after antigen challenge) and the results were as follows:

| Example | Dose (μg/kg body weight) | % Inhibition Eosinophil Accumulation | % Inhibition Hyper-reactivity |
|---------|-----|-----|-----|
| 16 | 0.2 | 62 | 80 |
|    | 2   | 78 | 95 |
| 17 | 0.2 | 68 | 58 |
|    | 2   | 61 | 88 |
| 20 | 0.2 | 67 | 85 |
|    | 2   | 79 | 100 |
| 21 | 0.2 | 49 | 82 |
|    | 2   | 79 | 85 |
| 23 | 2   | 51 | 79 |
| 24 | 0.2 | 26 | 44 |
|    | 2   | 77 | 85 |
| 27 | 0.2 | 58 | 88 |
|    | 2   | 90 | 87 |
| 28 | 0.2 | 3  | 70 |
|    | 2   | 62 | 47 |
| Dexamethasone (Positive Control) | 200 | 55 | 80 |

The compounds of Examples 16, 17, 20, 21, 23, 24, 27 and 28 were also tested in assay (4) the RPMI 8866/MAdCAM-1 adhesion assay and the results were as follows:

| Example | pIC$_{50}$ | SEM* | n* |
|---------|-----------|------|-----|
| 16 | 6.8 | 0.09 | 3 |
| 17 | 6.8 | 0.08 | 3 |
| 20 | 6.7 | 0.16 | 2 |
| 21 | 6.7 | 0.08 | 3 |
| 23 | 7.2 | 0.27 | 3 |
| 24 | 6.6 | 0.05 | 3 |
| 27 | 7.5 | 0.2 | 3 |
| 28 | 6.9 | 0.1 | 3 |

*SEM standard error of the mean of n experiments

| Abbreviations | |
|---|---|
| WSCDI | 1-(3-dimethylaminopropyl)-3-ethylcarbodiimide hydrochloride |
| PyBop | benzotriazol-1-yl-oxy-trispyrrolidinophosphonium hexafluorophosphate |
| DIC | 1,3-diisopropylcarbodiimide |
| HOBT | 1-hydroxybenzotriazole |
| Boc | tert butoxycarbonyl |
| Fmoc | 9-fluorenylmethoxycarbonyl |
| Cbz | carbobenzyloxy |
| DIPEA | diisopropylethylamine |
| DCM | dichloromethane |
| DMF | dimethylformamide |
| THF | tetrahydrofuran |
| NMP | 1-methyl-2-pyrrolidinone |

References:
Baron, J. L. et al., (1994). J. Clin. Invest. 93, 1700–1708.
Danahay et al., (1997). Br. J. Pharmacol. 120(2), 289–297.
Ferguson, T. A et al., (1991). Proc. Natl. Acad. Sci. USA 88, 8072–8076.
Griffiths, J. and Hawkins, C. (1977). J. Appl. Chem. Biotechnol. 27(10), 558–564.
Lobb, R. R. and Hemler, M. E. (1994). J. Clin. Invest. 94, 1722–1728.
Podolsky, D. K. et al., (1993). J. Clin. Invest. 92, 372–380.
Sanjar, S., McCabe, P. J., Fattah, D., Humbles, A. A. and Pole, S. M. (1992). Am. Rev. Respir. Dis. 145, A40.
Shah, S. et al., (1992). J. Med. Chem. 35(21), 3745–3754.
Wahl, S. M. et al., (1994). J. Clin. Invest. 94, 655–662.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

What is claimed is:

1. A compound of formula I:

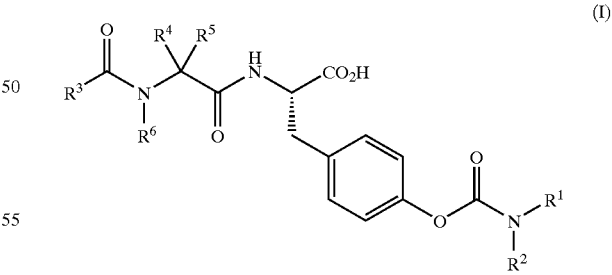

wherein $R^1$ and $R^2$ independently represent
(i) —$C_{1-6}$ alkyl, —$C_{3-8}$ cycloalkyl or —$C_{1-3}$ alkylC$_{3-8}$ cycloalkyl,
or such a group in which alkyl or cycloalkyl is substituted by one or more halogen, —CN, nitro, hydroxy or —O$C_{1-6}$ alkyl groups;
(ii) —(CH$_2$)$_e$Ar$^1$ or —(CH$_2$)$_e$OAr$^1$;
or NR$^1$R$^2$ together represent pyrrolidinyl, piperidinyl, piperazinyl, thiomorpholinyl, morpholinyl or azepinyl, or such a group fused to a benzene ring, optionally substituted by one or more —(CO)$_n$(CH$_2$)$_r$Ar$^1$, —(CO)$_n$ C$_{1-6}$ alkylAr$^1$Ar$^2$, —(CO)$_n$C$_{1-6}$alkyl, —(CH$_2$)$_r$ OH, —(CH$_2$)$_r$O(CH$_2$)$_p$OH, —(CH$_2$)$_r$OC$_{1-6}$ alkyl, —O(CH$_2$)$_r$Ar$^1$, —(CH$_2$)$_r$SO$_2$Ar$^1$, piperidin-1-yl, —(CH$_2$)$_r$CONR$^8$R$^9$, —NR$^{10}$(CO)$_n$(CH$_2$)$_r$Ar$^1$, —NR$^{10}$(CO)$_n$C$_{1-3}$alkylC$_{3-6}$ cycloalkyl, —NR$^{10}$(CO)$_n$C$_{1-6}$ alkyldiC$_{3-6}$ cycloalkyl, —CONR$^{10}$(CH$_2$)$_r$Ar$^1$, halogen, —NHSO$_2$C$_{1-6}$alkyl, —SO$_2$NR$^{10}$R$^{11}$, —SO$_2$C$_{1-6}$ alkyl or —SO$_2$Ar$^2$ groups;

R$^3$ represents —C$_{1-6}$alkylNHC(=NH)NH$_2$, —C$_{2-6}$alkenylNHC(=NH)NH$_2$, —C$_{2-6}$alkynylNHC(=NH)NH$_2$, —C$_{1-6}$alkylNR$^{14}$R$^{18}$, —(CH$_2$)$_h$CONR$^{14}$R$^{18}$, —(CH$_2$)$_h$COC$_{1-6}$alkyl, —(CH$_2$)$_d$CHNR$^{18}$CONR$^{20}$R$^{21}$, —(CH$_2$)$_m$NR$^{18}$CONR$^{14}$R$^{18}$, —(CH$_2$)$_d$NR$^{18}$Ar$^3$, —(CH$_2$)$_d$CONR$^{18}$Ar$^3$, —(CH$_2$)$_h$COOR$^{18}$, —(CH$_2$)$_c$Ar$^3$, —O(CH$_2$)$_c$Ar$^3$, —(CH$_2$)$_d$CO(CH$_2$)$_s$Ar$^3$ or —(CH$_2$)$_d$OAr$^3$;

or R$^3$ represents —(CH$_2$)$_c$-2,4-imidazolidinedione, —(CH$_2$)$_c$(piperidin-4-yl), —(CH$_2$)$_c$(piperidin-3-yl), —(CH$_2$)$_c$(piperidin-2-yl), —(CH$_2$)$_c$(morpholin-3-yl) or —(CH$_2$)$_c$(morpholin-2-yl) optionally substituted on nitrogen by —(CO)$_f$C$_{1-6}$alkyl, —(CO)$_f$(CH$_2$)$_c$Ar$^2$ or —C(=NH)NH$_2$;

or R$^3$ represents —(CH$_2$)$_z$dibenzofuran optionally substituted by —C$_{1-6}$alkyl or halogen;

or R$^3$ represents —(CH$_2$)$_c$-thioxanthen-9-one;

R$^4$ represents hydrogen, —C$_{1-6}$ alkyl, —C$_{1-3}$ alkylC$_{3-6}$ cycloalkyl, —(CH$_2$)$_q$Ar$^2$, —C$_{1-4}$alkyl-X—R$^7$, —C$_{1-4}$ alkyl SO$_2$C$_{1-4}$ alkyl, —C$_{1-6}$alkylNR$^{12}$R$^{13}$ or —C$_{1-6}$ alkylNR$^{12}$COC$_{1-6}$ alkyl;

R$^5$ represents hydrogen, or R$^4$R$^5$ together with the carbon to which they are attached form a C$_{5-7}$ cycloalkyl ring;

R$^6$ represents hydrogen or —C$_{1-6}$alkyl;

R$^7$ represents hydrogen, —(CH$_2$)$_w$NR$^{12}$R$^{13}$, —(CH$_2$)$_u$Ar$^2$ or —(CH$_2$)$_w$NR$^{12}$COC$_{1-6}$ alkyl;

R$^8$, R$^9$, R$^{16}$ and R$^{17}$ independently represent hydrogen, —C$_{1-6}$alkyl, —C$_{3-6}$cycloalkyl, —C$_{1-3}$ alkylC$_{3-6}$ cycloalkyl, —C$_{2-6}$alkenyl or NR$^8$R$^9$ or NR$^{16}$R$^{17}$ together represents morpholinyl, pyrrolidinyl, piperidinyl, piperazinyl or piperazinyl N-substituted by —C$_{1-6}$ alkyl, —COphenyl or —SO$_2$methyl;

R$^{10}$, R$^{11}$, R$^{12}$, R$^{13}$, R$^{15}$, R$^{18}$, R$^{20}$ and R$^{21}$ independently represent hydrogen or —C$_{1-6}$alkyl;

R$^{14}$, R$^{19}$ and R$^{22}$ independently represent hydrogen, —C$_{1-6}$alkyl, —C$_{3-6}$ cycloalkyl or —(CH$_2$)$_x$Ar$^4$ or NR$^{14}$R$^{18}$ or NR$^{15}$R$^{22}$ together represents morpholinyl, pyrrolidinyl, piperidinyl, piperazinyl or N—C$_{1-6}$alkylpiperazinyl;

Ar$^1$ represents phenyl or a 5 or 6 membered heterocyclic aromatic ring containing 1 to 3 heteroatoms selected from O, N and S optionally substituted by one or more halogen, —C$_{1-6}$alkyl, hydroxy, —OC$_{1-6}$alkyl, —CF$_3$, nitro, —Ar$^2$ or —OAr$^2$ groups;

Ar$^2$ represents phenyl optionally substituted by one or more halogen, —C$_{1-6}$alkyl, hydroxy, —OC$_{1-6}$alkyl, —CF$_3$ or nitro groups;

Ar$^3$ represents phenyl, a 5 or 6 membered heterocyclic aromatic ring containing 1 to 3 heteroatoms selected from O, N or S, or such a group fused to a benzene ring, optionally substituted by one or more —CO(CH$_2$)$_g$Ar$^4$, —(CH$_2$)$_y$Ar$^4$, —(CH$_2$)$_y$COAr$^4$, —(CO)$_a$C$_{1-6}$ alkyl, —(CO)$_a$C$_{2-6}$ alkenyl, —(CO)$_a$C$_{2-6}$ alkynyl, —(CO)$_a$ C$_{3-8}$cycloalkyl, —(CO)$_a$C$_{1-6}$haloalkyl, halogen, —COCH$_2$ CN, —(CH$_2$)$_b$NR$^{16}$R$^{17}$, —(CH$_2$)$_b$NHC(=NH)NH$_2$, —CYNR$^{16}$(CO)$_a$R$^{17}$, —(CH$_2$)$_b$NR$^{15}$COR$^{19}$, —(CH$_2$)$_b$CONR$^{15}$R$^{22}$, —(CH$_2$)$_b$NR$^{15}$CONR$^{15}$R$^{22}$, —(CH$_2$)$_b$CONR$^{15}$(CH$_2$)$_j$NR$^{15R22}$, —(CH$_2$)$_b$SO$_2$NR$^{15}$R$^{22}$, —(CH$_2$)$_b$SO$_2$NR$^{15}$COAr$^2$, —(CH$_2$)$_b$NR$^{15}$SO$_2$R$^{19}$, —SO$_2$R$^{19}$, —SOR$^{19}$, —(CH$_2$)$_z$ OH, —COOR$^{15}$, —CHO, —OC$_{1-10}$alkyl, —O(CH$_2$)$_j$ NR$^{15}$R$^{22}$, —O(CH$_2$)$_j$NHC(=NH)NH$_2$, —O(CH$_2$)$_b$ CONR$^{16}$R$^{17}$, —O(CH$_2$)$_k$COOR$^{15}$, —O(CH$_2$)$_j$OAr$^2$, —O(CH$_2$)$_b$Ar$^2$, 3-phenyl-2-pyrazolin-5-one or 4,5-dihydro-3(2H)-pyridazinone groups;

Ar$^4$ represents phenyl or a 5 or 6 membered heterocyclic aromatic ring containing 1 to 3 heteroatoms selected from O, N and S optionally substituted by one or more halogen, —C$_{1-6}$alkyl, hydroxy, —OC$_{1-6}$alkyl, —CF$_3$, nitro or —CONH$_2$ groups;

X and Y independently represent O or S;

a, f, k, s and n independently represent 0 or 1;

b, c, r, x, y and z independently represent an integer 0 to 2;

d, g and u independently represent 1 or 2;

e, h, q and w independently represent an integer 1 to 3;

j and p independently represent an integer 2 to 4;

m independently represents an integer 0 to 4;

t independently represents an integer 0 to 3;

or salts or solvates thereof.

2. A compound according to claim 1 wherein R$^4$ represents —C$_{1-6}$ alkyl, R$^5$ represents hydrogen or R$^4$R$^5$, together with the carbon to which they are attached, forms a cyclohexyl ring, and R$^6$ represents hydrogen or methyl.

3. A compound according to claim 2 wherein R$^4$ represents —C$_{1-6}$ alkyl and R$^5$ and R$^6$ represent hydrogen.

4. A compound according to claim 3 wherein R$^4$ represents —CH$_2$CHMe$_2$ and R$^5$ and R$^6$ represent hydrogen.

5. A compound according to claim 1 wherein NR$^1$R$^2$ together represent piperidinyl, piperazinyl, thiomorpholinyl, morpholinyl or 1,2,3,4-tetrahydroisoquinoline optionally substituted by a —C(CO)$_n$ (CH$_2$)$_r$Ar$^1$, —(CO)$_n$C$_{1-6}$alkyl, —(CH$_2$)$_r$CONR$^8$R$^9$, —NR$^{10}$(CO)$_n$(CH$_2$)$_r$Ar$^1$, —NR$^{10}$(CO)$_n$C$_{1-3}$ alkylC$_{3-6}$ cycloalkyl, —NR$^{10}$(CO)$_n$C$_{1-6}$ alkyldiC$_{3-6}$ cycloalkyl, —(CH$_2$)$_r$OC$_{1-6}$ alkyl, —(CH$_2$)$_r$O(CH$_2$)$_p$OH, piperidin-1-yl, —(CH$_2$)$_r$OH or —CONR$^{10}$(CH$_2$)$_r$Ar$^1$ group.

6. A compound according to claim 5 wherein NR$^1$R$^2$ together represents morpholinyl or piperazinyl optionally N-substituted by —(CO)$_n$C$_{1-6}$ alkyl, piperazinyl N-substituted by —(CO)$_n$(CH$_2$)$_r$Ar$^1$, piperidinyl substituted by —NR$^{10}$(CO)$_n$(CH$_2$)$_r$Ar$^1$ or piperidinyl substituted by —(CH$_2$)$_t$CONR$^8$R$^9$.

7. A compound according to claim 1 wherein R$^3$ represents —(CH$_2$)$_c$-2,4-imidazolidinedione-3-yl, —(CH$_2$)$_c$-thioxanthen-9-one-3-yl, —(CH$_2$)$_c$Ar$^3$, —O(CH$_2$)$_c$Ar$^3$, —(CH$_2$)$_d$OAr$^3$ or —(CH$_2$)$_z$dibenzofuran.

8. A compound according to claim 7 wherein R$^3$ represents —OCH$_2$Ar$^3$, —CH$_2$OAr$^3$ or dibenzofuran.

9. A compound according to claim 8 wherein R$^3$ represents —CH$_2$OAr$^3$.

10. A compound according to claim 1 wherein R$^4$ and R$^5$ have the stereochemical orientation shown in formula (Ia):

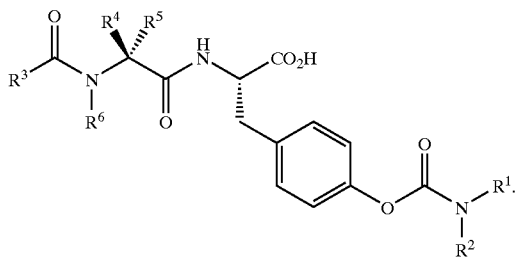

(Ia)

11. A compound selected from the group consisting of:
(2S)-2-[((2S)-2-{[2-(2-Benzoylphenoxy)acetyl]amino}-4-methyl pentanoyl)amino]-3-{4-[({4-[(2-phenylacetyl)amino]-1-piperidinyl}carbonyl)oxy]phenyl}propanoic acid;
(2S)-2-({(2S)-4-Methyl-2-[(2-{[3-(1-piperidinylcarbonyl)-2-naphthyl]oxy}acetyl)amino]pentanoyl}amino)-3-{4-[({4-[(2-phenylacetyl)amino]-1-piperidinyl}carbonyl)oxy]phenyl}propanoic acid;
(2S)-3-{4-[({4-[(2,2-Dicyclohexylacetyl)amino]-1-piperidinyl}carbonyl)oxy]phenyl}-2-{[(2S)-4-methyl-2-({2-[4-(1-piperidinylcarbonyl)phenoxy]acetyl}amino)pentanoyl]amino}propanoic acid;
(2S)-2-{[(2S)-4-Methyl-2-({2-[4-(1-piperidinylcarbonyl)phenoxy]acetyl}amino)pentanoyl]amino}-3-{4-[(4-morpholinylcarbonyl)oxy]phenyl}propanoic acid;
(2S)-3-[4-({[4-(Aminocarbonyl)-1-piperidinyl]carbonyl}oxy)phenyl]-2-{[(2S)-4-methyl-2-({2-[4-(1-piperidinylcarbonyl)phenoxy]acetyl}amino)pentanoyl]amino}propanoic acid;
(2S)-3-{4-[({4-[(2-Cyclohexylacetyl)amino]-1-piperidinyl}carbonyl)oxy]phenyl}-2-[((2S)-2-{[2-(2-iodophenoxy)acetyl]amino}-4-methylpentanoyl)amino]propanoic acid;
(2S)-3-{4-[({4-[(2,2-Dicyclohexylacetyl)amino]-1-piperidinyl}carbonyl)oxy]phenyl}-2-[((2S)-2-{[2-(2-iodophenoxy)acetyl]amino}-4-methylpentanoyl)amino]propanoic acid;
(2S)-2-({(2S)-2-[(Dibenzo[b,d]furan-4-ylcarbonyl)amino]-4-methyl pentanoyl}amino)-3-{4-[(4-morpholinylcarbonyl)oxy]phenyl}propanoic acid;
(2S)-2-({(2S)-2-[(Dibenzo[b,d]furan-4-ylcarbonyl)amino]-4-methyl pentanoyl}amino)-3-{4-[({4-[(2-phenylacetyl)amino]-1-piperidinyl}carbonyl)oxy]phenyl}propanoic acid;
(2S)-2-[((2S)-2-{[2-(2-Iodophenoxy)acetyl]amino}-4-methyl pentanoyl)amino]-3-{4-[({4-[(2-phenylacetyl)amino]-1-piperidinyl}carbonyl)oxy]phenyl}propanoic acid;
(2S)-3-(4-{[(4-Acetyl-1-piperazinyl)carbonyl]oxy}phenyl)-2-[((2S)-2-{[2-(2-iodophenoxy)acetyl]amino}-4-methylpentanoyl)amino]propanoic acid;
(2S)-3-(4-{[(4-Benzoyl-1-piperazinyl)carbonyl]oxy}phenyl)-2-[((2S)-2-{[2-(2-iodophenoxy)acetyl]amino}-4-methylpentanoyl)amino]propanoic acid;
(2S)-3-(4-{[(4-Benzoyl-1-piperazinyl)carbonyl]oxy}phenyl)-2-[((2S)-2-{[2-(2,4-dichlorophenoxy)acetyl]amino}-4-methylpentanoyl)amino]propanoic acid;
(2S)-3-[4-({[4-(Aminocarbonyl)-1-piperidinyl]carbonyl}oxy)phenyl]-2-[((2S)-2-{[2-(2-iodophenoxy)acetyl]amino}-4-methylpentanoyl)amino]propanoic acid;
(2S)-2-{[(2S)-2-({2-[2-(Tert-butyl)phenoxy]acetyl}amino)-4-methyl pentanoyl]amino}-3-[4-({[4-(1-piperidinylcarbonyl)-1-piperidinyl]carbonyl}oxy)phenyl]propanoic acid;
(2S)-2-[((2S)-4-Methyl-2-{[2-(2-methylphenoxy)acetyl]amino}pentanoyl)amino]-3-[4-({[4-(1-piperidinylcarbonyl)-1-piperidinyl]carbonyl}oxy)phenyl]propanoic acid;
(2S)-2-({(2S)-2-[(Dibenzo[b,d]furan-4-ylcarbonyl)amino]-4-methyl pentanoyl}amino)-3-[4-({[4-(1-piperidinylcarbonyl)-1-piperidinyl]carbonyl}oxy)phenyl]propanoic acid;
(2S)-2-{[(2S)-2-({2-[(1-Bromo-2-naphthyl)oxy]acetyl}amino)-4-methylpentanoyl]amino}-3-[4-({[4-(1-piperidinylcarbonyl)-1-piperidinyl]carbonyl}oxy)phenyl]propanoic acid;
(2S)-2-{[(2S)-2-({2-[2-(Tert-butyl)phenoxy]acetyl}amino)-4-methyl pentanoyl]amino}-3-(4-{[(4-{[(4-fluorobenzyl)amino]carbonyl}-1-piperidinyl)carbonyl]oxy}phenyl)propanoic acid;
(2S)-2-[((2S)-2-{[2-(2,4-Dichlorophenoxy)acetyl]amino}-4-methyl pentanoyl)amino]-3-{4-[(4-morpholinylcarbonyl)oxy]phenyl}propanoic acid;
(2S)-2-[((2S)-2-{[2-(2-Benzoylphenoxy)acetyl]amino}-4-methyl pentanoyl)amino]-3-{4-[(4-morpholinylcarbonyl)oxy]phenyl}propanoic acid;
(2S)-2-[((2S)-4-Methyl-2-{[2-(2-propylphenoxy)acetyl]amino}pentanoyl)amino]-3-{4-[(4-morpholinylcarbonyl)oxy]phenyl}propanoic acid;
(2S)-2-{[(2S)-2-({2-[(1-Bromo-2-naphthyl)oxy]acetyl}amino)-4-methylpentanoyl]amino}-3-{4-[(4-morpholinylcarbonyl)oxy]phenyl}propanoic acid;
(2S)-2-[((2S)-2-{[(Benzyloxy)carbonyl]amino}-4-methylpentanoyl)amino]-3-{4-[(4-morpholinylcarbonyl)oxy]phenyl}propanoic acid;
(2S)-3-[4-({[4-(2-Furoyl)-1-piperazinyl]carbonyl}oxy)phenyl]-2-[((2S)-2-{[2-(2-iodophenoxy)acetyl]amino}-4-methylpentanoyl)amino]propanoic acid;
(2S)-2-[((2S)-2-{[2-(2-Cycohexylphenoxy)acetyl]amino}-4-methyl pentanoyl)amino]-3-[4-({[4-(2-furoyl)-1-piperazinyl]carbonyl}oxy)phenyl]propanoic acid;
(2S)-2-{[(2S)-2-({2-[(1-Bromo-2-naphthyl)oxy]acetyl}amino)-4-methylpentanoyl]amino}-3-[4-({[4-(2-furoyl)-1-piperazinyl]carbonyl}oxy)phenyl]propanoic acid;
(2S)-3-(4-{[(4-{[2-(4-Chlorophenyl)acetyl]amino}-1-piperidinyl)carbonyl]oxy}phenyl)-2-[((2S)-2-{[2-(2-cyclohexylphenoxy)acetyl]amino}-4-methylpentanoyl)amino]propanoic acid;
(2S)-2-[((2S)-2-{[2-(2-Benzoylphenoxy)acetyl]amino}-4-methyl pentanoyl)amino]-3-(4-{[(4-{[2-(4-chlorophenyl)acetyl]amino}-1-piperidinyl)carbonyl]oxy}phenyl)propanoic acid;
(2S)-3-(4-{[(4-{[2-(4-Chlorophenyl)acetyl]amino}-1-piperidinyl)carbonyl]oxy}phenyl)-2-[((2S)-2-{[2-(2-iodophenoxy)acetyl]amino}-4-methyl pentanoyl)amino]propanoic acid;
(2S)-2-{[(2S)-2-({2-[2-(Tert-butyl)phenoxy]acetyl}amino)-4-methyl pentanoyl]amino}-3-(4-{[(4-{[2-(4-chlorophenyl)acetyl]amino}-1-piperidinyl)carbonyl]oxy}phenyl)propanoic acid;
(2S)-3-(4-{[(4-{[2-(4-Chlorophenyl)acetyl]amino}-1-piperidinyl)carbonyl]oxy}phenyl)-2-({(2S)-2-

[(dibenzo[b,d]furan-4-ylcarbonyl)amino]-4-methylpentanoyl}amino)propanoic acid;

(2S)-3-(4-{[(4-{[2-(4-Chlorophenyl)acetyl]amino}-1-piperidinyl)carbonyl]oxy}phenyl)-2-({(2S)-4-methyl-2-[(2-{[3-(1-piperidinylcarbonyl)-2-naphthyl]oxy}acetyl)amino]pentanoyl}amino)propanoic acid;

(2S)-2-{[(2S)-2-({2-[2-(Tert-butyl)phenoxy]acetyl}amino)-4-methyl pentanoyl]amino}-3-{4-[({4-[(2-cyclohexylacetyl)amino]-1-piperidinyl}carbonyl)oxy]phenyl}propanoic acid;

(2S)-2-{[(2S)-2-({2-[2-(Tert-butyl)phenoxy]acetyl}amino)-4-methyl pentanoyl]amino}-3-{4-[({4-[(2,2-dicyclohexylacetyl)amino]-1-piperidinyl}carbonyl)oxy]phenyl}propanoic acid;

(2S)-2-[((2S)-4-Methyl-2-{[2-(2-methylphenoxy)acetyl]amino}pentanoyl)amino]-3-{4-[({4-[(2-phenylacetyl)amino]-1-piperidinyl}carbonyl)oxy]phenyl}propanoic acid;

(2S)-2-[((2S)-2-{[2-(2-Cyclohexylphenoxy)acetyl]amino}-4-methyl pentanoyl)amino]-3-{4-[({4-[(2-phenylacetyl)amino]-1-piperidinyl}carbonyl)oxy]phenyl}propanoic acid;

(2S)-3-{4-[({4-[(2-Cyclohexylacetyl)amino]-1-piperidinyl}carbonyl)oxy]phenyl}-2-[((2S)-2-{[2-(2-cyclohexylphenoxy)acetyl]amino}-4-methyl pentanoyl)amino]propanoic acid;

and salts and solvates thereof.

12. A compound selected from the group consisting of:

(2S)-2-[((2S)-2-{[2-(2-Iodophenoxy)acetyl]amino}-4-methyl pentanoyl)amino]-3-{4-[(4-morpholinylcarbonyl)oxy]phenyl}propanoic acid;

(2S)-2-{[(2S)-2-({2-[2-(Tert-butyl)phenoxy]acetyl}amino)-4-methyl pentanoyl]amino}-3-{4-[(4-morpholinylcarbonyl)oxy]phenyl}propanoic acid;

(2S)-3-(4-{[(4-Acetyl-1-piperazinyl)carbonyl]oxy}phenyl)-2-{[(2S)-2-({2-[2-(tert-butyl)phenoxy]acetyl}amino)-4-methylpentanoyl]amino}propanoic acid;

(2S)-2-[((2S)-2-{[2-(2-Cyclohexylphenoxy)acetyl]amino}-4-methyl pentanoyl)amino]-3-{4-[(4-morpholinylcarbonyl)oxy]phenyl}propanoic acid;

(2S)-2-{[(2S)-2-({2-[2-(Tert-butyl)phenoxy]acetyl}amino)-4-methyl pentanoyl]amino}-3-{4-[({4-[(2-phenylacetyl)amino]-1-piperidinyl}carbonyl)oxy]phenyl}propanoic acid;

(2S)-3-(4-{[(4-Benzoyl-1-piperazinyl)carbonyl]oxy}phenyl)-2-{[(2S)-2-({2-[2-(tert-butyl)phenoxy]acetyl}amino)-4-methylpentanoyl]amino}propanoic acid;

(2S)-3-(4-{[(4-Acetyl-1-piperazinyl)carbonyl]oxy}phenyl)-2-({(2S)-2-[(dibenzo[b,d]furan-4-ylcarbonyl)amino]-4-methylpentanoyl}amino)propanoic acid;

(2S)-2-{[(2S)-2-({2-[2-(Tert-butyl)phenoxy]acetyl}amino)-4-methyl pentanoyl]amino}-3-[4-({[4-(2-furoyl)-1-piperazinyl]carbonyl}oxy)phenyl]propanoic acid;

(2S)-2-({(2S)-2-[(Dibenzo[b,d]furan-4-ylcarbonyl)amino]-4-methyl pentanoyl}amino)-3-[4-({[4-(2-furoyl)-1-piperazinyl]carbonyl}oxy)phenyl]propanoic acid;

(2S)-3-(4-{[(4-Benzoyl-1-piperazinyl)carbonyl]oxy}phenyl)-2-[((2S)-4-methyl-2-{[2-(2-methylphenoxy)acetyl]amino}pentanoyl)amino]propanoic acid;

(2S)-3-(4-{[(4-Benzoyl-1-piperazinyl)carbonyl]oxy}phenyl)-2-({(2S)-2-[(dibenzo[b,d]furan-4-ylcarbonyl)amino]-4-methylpentanoyl}amino)propanoic acid;

and salts and solvates thereof.

13. A compound selected from the group consisting of:

(2S)-3-(4-{[(4-Acetyl-1-piperazinyl)carbonyl]oxy}phenyl)-2-[((2S)-4-methyl-2-{[2-(2-methylphenoxy)acetyl]amino}pentanoyl)amino]propanoic acid;

(2S)-3-[4-({[4-(Aminocarbonyl)-1-piperidinyl]carbonyl}oxy)phenyl]-2-({(2S)-2-[(dibenzo[b,d]furan-4-ylcarbonyl)amino]-4-methylpentanoyl}amino)propanoic acid;

(2S)-3-[4-({[4-(Aminocarbonyl)-1-piperidinyl]carbonyl}oxy)phenyl]-2-{[(2S)-2-({2-[2-(tert-butyl)phenoxy]acetyl}amino)-4-methylpentanoyl]amino}propanoic acid;

(2S)-2-[((2S)-4-Methyl-2-{[2-(2-methylphenoxy)acetyl]amino}pentanoyl)amino]-3-{4-[(4-morpholinylcarbonyl)oxy]phenyl}propanoic acid;

(2S)-3-[4-({[4-(Aminocarbonyl)-1-piperidinyl]carbonyl}oxy)phenyl]-2-[((2S)-2-{[2-(2-benzoylphenoxy)acetyl]amino}-4-methylpentanoyl)amino]propanoic acid;

(2S)-2-{[(2S)-2-({2-[4-(Aminocarbonyl)phenoxy]acetyl}amino)-4-methylpentanoyl]amino}-3-[4-({[4-(aminocarbonyl)-1-piperidinyl]carbonyl}oxy)phenyl]propanoic acid;

and salts and solvates thereof.

14. A compound selected from the group consisting of:

(2S)-3-[4-({[4-(Aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid or a salt or solvate thereof.

15. A compound according to claim 14 which is:

(2S)-3-[4-({[4-(Aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid potassium salt or a solvate thereof.

16. A pharmaceutical composition comprising a compound of formula (I) as defined in claim 1 or a pharmaceutically acceptable salt or solvate thereof in admixture with one or more pharmaceutically acceptable diluents or carriers.

17. A pharmaceutical composition comprising a compound of formula (I) according to claim 1 or a physiologically acceptable salt or solvate thereof in combination with a long acting $\beta_2$ adrenergic receptor agonist.

18. A process for preparation of a compound according to claim 1 which comprises:
(a) hydrolyzing a carboxylic acid ester of formula (II)

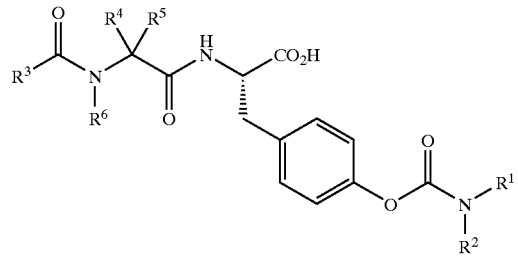

wherein $R^1$, $R^2$, $R^3$, $R^4$, $R^5$ and $R^6$ are as defined in claim 1 and R is a group capable of forming a carboxylic acid ester; or (b) deprotecting a compound according to claim 1 which is protected.

19. A method of inhibiting eosinophil infiltration into the lungs of a patient comprising administering an effective amount of a compound of claim 1 to a patient in need thereof.

20. A method of antagonizing VLA-4 comprising administering an effective amount of a compound of claim 1 to a patient in need thereof.

* * * * *